(12) United States Patent
Tsai et al.

(10) Patent No.: US 11,957,051 B2
(45) Date of Patent: Apr. 9, 2024

(54) ORGANIC SEMICONDUCTOR MIXTURE AND ORGANIC OPTOELECTRONIC DEVICE CONTAINING THE SAME

(71) Applicant: Raynergy Tek Incorporation, Hsinchu (TW)

(72) Inventors: Chia-Hua Tsai, Hsinchu (TW); Chuang-Yi Liao, Hsinchu (TW); Wei-Long Li, Hsinchu (TW); Yu-Tang Hsiao, Hsinchu (TW)

(73) Assignee: RAYNERGY TEK INCORPORATION, Hsinchu (TW)

( * ) Notice: Subject to any disclaimer, the term of this patent is extended or adjusted under 35 U.S.C. 154(b) by 0 days.

(21) Appl. No.: 18/128,590

(22) Filed: Mar. 30, 2023

(65) Prior Publication Data
US 2023/0320212 A1 Oct. 5, 2023

Related U.S. Application Data

(60) Provisional application No. 63/362,140, filed on Mar. 30, 2022.

(51) Int. Cl.
*H10K 85/60* (2023.01)
*C07D 495/04* (2006.01)
(Continued)

(52) U.S. Cl.
CPC ....... *H10K 85/6576* (2023.02); *C07D 495/04* (2013.01); *C07D 495/22* (2013.01);
(Continued)

(58) Field of Classification Search
CPC ...... H10K 30/30; H10K 71/12; H10K 85/113; H10K 85/151; H10K 85/626; H10K 85/655; H10K 85/657; H10K 85/6576
See application file for complete search history.

(56) References Cited

U.S. PATENT DOCUMENTS

2004/0099307 A1* 5/2004 Sun ............ H10K 85/114
136/263
2007/0095391 A1* 5/2007 Sun ............ H10K 85/151
136/263
(Continued)

FOREIGN PATENT DOCUMENTS

TW 201833169 9/2018
TW 201922750 6/2019
WO WO-2010036494 A1 * 4/2010 ........... C08G 61/126

OTHER PUBLICATIONS

Zuo Xiao et al., Carbon-Oxygen-Bridged Ladder-Type Building Blocks for Highly Efficient Nonfullerene Acceptors, 2018, Wiley-VCH Verlag GmbH & Co. KGaA, Weinheim.
Taiwan Intellectual Property Office, Official action dated Oct. 30, 2023.
Wang et al. "Controlling Molecular Mass of Low-Band-Gap Polymer Acceptors for High-Performance All-Polymer Solar Cells", May 2020, Joule.
(Continued)

*Primary Examiner* — Golam Mowla
(74) *Attorney, Agent, or Firm* — WPAT, P.C

(57) ABSTRACT

An organic semiconductor mixture and an organic optoelectronic device containing the same are provided. A n-type organic semiconductor compound in the organic semiconductor mixture has a novel chemical structure so that the mixture has good thermal stability and property difference during batch production is also minimized. The organic semiconductor mixture is applied to organic optoelectronic devices such as organic photovoltaic devices for providing good energy conversion efficiency while in use.

15 Claims, 9 Drawing Sheets

(51) Int. Cl.
*C07D 495/22* (2006.01)
*C07D 513/22* (2006.01)
*C07D 519/00* (2006.01)
*C08G 61/12* (2006.01)
*H10K 30/30* (2023.01)
*H10K 85/10* (2023.01)

(52) U.S. Cl.
CPC ......... *C07D 513/22* (2013.01); *C07D 519/00* (2013.01); *C08G 61/126* (2013.01); *H10K 85/113* (2023.02); *H10K 85/151* (2023.02); *H10K 85/626* (2023.02); *H10K 85/655* (2023.02); *H10K 85/657* (2023.02); *C08G 2261/124* (2013.01); *C08G 2261/1412* (2013.01); *C08G 2261/146* (2013.01); *C08G 2261/18* (2013.01); *C08G 2261/228* (2013.01); *C08G 2261/3223* (2013.01); *C08G 2261/3243* (2013.01); *C08G 2261/3246* (2013.01); *C08G 2261/91* (2013.01); *H10K 30/30* (2023.02)

(56) References Cited

U.S. PATENT DOCUMENTS

2009/0084436 A1* 4/2009 Yang ...................... H10K 30/35
                                                          136/256
2013/0247992 A1* 9/2013 Drees ................... H10K 85/151
                                                          136/263

OTHER PUBLICATIONS

Liu et al. "Narrow-Band-Gap Conjugated Chromophores with Extended Molecular Lengths", Dec. 2012, JACS.

Wang et al. "Series of Multifluorine Substituted Oligomers for Organic Solar Cells with Efficiency over 9% and Fill Factor of 0.77 by Combination Thermal and Solvent Vapor Annealing", May 2016, JACS.

Qin et al. "The performance-stability conundrum of BTPbased organic solar cells", Aug. 2021, JACS.

* cited by examiner

ORGANIC SEMICONDUCTOR MIXTURE AND ORGANIC OPTOELECTRONIC DEVICE CONTAINING THE SAME

BACKGROUND OF THE INVENTION

The present invention relates to an organic semiconductor mixture, especially to an organic semiconductor mixture and an organic optoelectronic device containing the same.

PRIOR ART

In recent years, demands for organic semiconductor compounds are increasing in order to produce more general electronics with lower cost. Compared with conventional semiconductor materials, organic semiconductor compounds have wider absorption range, larger absorption coefficient, and adjustable structure. Its absorption range, energy gap and solubility can also be adjusted according to user's requirements. Moreover, organic materials have advantages in production of components including low cost, flexibility, lower toxicity, and large-area fabrication. Thus, the organic optoelectronic materials have good competitiveness on various fields.

The organic optoelectronic materials have wide applications including organic field-effect transistor (OFET), organic light-emitting diode (OLED), organic photodetector (OPD), organic photovoltaic (OPV) cells, transducers, respective components and assemblies of memory components and logic circuit, etc. In the respective components or assemblies of the above applications, the organic semiconductor materials are in the form of a thin-film with a thickness ranging from 50 nm to 1 μm.

As a kind of photodetector device, the above organic photovoltaic (OPV) cell is a light receiving element. After exposure to light, electrons are excited to a high energy level to form free electrons moving in a circuit and create an electric current. The OPV generally includes a set of electrodes and an active layer (photoactive layer) arranged between the electrodes. Materials for the active layer used in the OPV directly play an important role since they have direct impact on the performance. The materials are divided into two groups, donors and acceptors.

The most common donor materials include organic polymers, oligomers, and small molecule unit, each of which has their own advantages. For example, the low molecule weight property of the materials is beneficial to synthesis and purification, suitable for thin-film deposition, and quite stable compared with other materials. As to the polymers, they have better thermal stability and mechanical properties and suitable for wet process, and thus quite favored now. Conjugated polymers have alternate single bond-double bond conjugation on the main chain so as to have intrinsically conductive property. Now development of D-A type conjugate polymers is the main stream. The energy levels and energy gaps of the polymer can be adjusted by push-pull electronic effects caused by interaction between electron-rich units and electron-deficient units of the polymer.

The acceptor materials used in combination with the donor materials include fullerene derivatives with high conductivity and absorption range between 400-600 nm, graphene, metal oxides, quantum dots, and non-fullerene organic compounds and the derivatives just emerged in recent years. The Non-Fullerene Acceptors (NFAs) have replaced the fullerene due to tunability of the absorption spectrum and high absorption efficiency, and thus become an important milestone in the development of OPV. The use of NFAs in combination with polymers can provide an efficiency of over 18% in the OPV field.

However, development of NFAs is quite difficult at early stage due to lower power conversion efficiency caused by difficulty in control of its compound morphology Moreover, restricted absorption bands and range of energy levels lead to limits on combinations of donor and acceptor materials. However, a lot of research related to NFAs since 2015 have attributed to significant improvement on its power conversion efficiency (PCE). Thus, NFAs have become a competitive material and the improvement mainly comes from progress in synthesis methods, changes in material design strategy, etc. Various donor materials developed for pairing with fullerene acceptors before also have contributed to the research and development of NFAs in an indirect way. While in use, fullerene acceptors may not be able to combine with donor materials for higher efficiency. Therefore, the development of NFAs for replacement of conventional fullerene acceptors is an is an important breakthrough in the materials for the active layer.

In the development of NFA materials, most of them have molecules with a structure of A-D-A, an electron-rich unit as a center with electron-deficient units on two sides. Generally, D is usually a molecule composed of benzene ring and thiophene while A is usually an indanone-cyano (IC) derivative. Another type of form is A'-D-A-D-A'. An electron-deficient unit used as a center is often with a chemical structure containing sulfur atom in order to enhance its performance.

In practical applications, NFAs still have certain limitations. For example, materials used for commercialization of organic solar cells need to have good thermal stability, however, most of NFAs have lower thermal stability. As to nonfullerene small molecule acceptors (NF-SMAs) with high efficiency, phase change, even serious phase separation occurs after heating due to nonfullerene stacking resulted from high crystallinity Thus, the efficiency is reduced. In previous literature, efficiency drop of such kind of compounds along with heating has also been mentioned.

In order to improve thermal stability of nonfullerene, one of the research directions is the use of nonfullerene copolymerized with thiophene to form nonfullerene polymer (also called P(nonfullerene)). The use of nonfullerene polymer provides absorption efficiency of nonfullerene, better thermal stability and mechanical properties. Yet issues including stability and reproducibility in synthesis also occur. The compatibility problem between donor and acceptor may also happen and further lead to lower efficiency.

In certain literature, it has mentioned that the increase in molecular weight and chain length not only increase thermal transition temperature of the polymer but also reduced changes in absorption spectrum after heating.

A number of issues need to be addressed while using the nonfullerene polymers. One of the issues is that a difference is generated between different production batches during polymerization of nonfullerene polymers. Another one is the problem of poor compatibility between polymer donors and polymer acceptors in all-polymer organic photovoltaic (OPV) system, which also causes reduction in efficiency. In previous research, it was mentioned that more serious phase separation may occur and further lead to lower efficiency while P(NFAs) are used. P(NFAs) material with higher molecular weight was found to have lower compatibility with donor material which resulted in lower efficiency of the device. The difference between production batches during synthesis of NFAs may cause lower efficiency of the device and there is no reproducibility.

Thus there is room for improvement and there is a need to provide a novel organic semiconductor mixture which addresses problems of stability and reproducibility in synthesis, reduction of performance gaps caused by variance in different production batches, and most important of all, reduction of component efficiency caused by poor film stability of nonfullerene after heating.

SUMMARY OF THE INVENTION

Therefore, it is a primary object of the present invention to provide an organic semiconductor mixture which overcomes shortcomings of conventional organic semiconductor compounds and provide at least one of the advantages mentioned above, especially good processability and easiness in mass production by solution processing method.

It is another object of the present invention to provide an organic optoelectronic device containing the present organic semiconductor mixture with excellent thermal stability and good energy conversion efficiency.

In order to achieve the above objects, an organic semiconductor mixture includes a p-type organic semiconductor compound and a n-type organic semiconductor compound. The p-type organic semiconductor compound is a conjugated polymer which includes at least one acceptor unit and at least one donor unit while the n-type organic semiconductor compound is represented by formula I:

group consisting of a vinyl group, a phenyl ring, an electron donating group, a substituted or unsubstituted monocyclic heteroaryl group containing 5 to 20 ring atoms, and a substituted or unsubstituted polycyclic heteroaryl group containing 5 to 20 ring atoms. $E^0$-$E^3$ are monocyclic or polycyclic heteroaryl groups containing 5-20 ring atoms and at least one electron-withdrawing group, defined as different from the $SP^1$ group. a, b, c, and d are 0 or 1 and a+b+c+d≥2 while m, n, o, p, q, r, s, and t are 0, 1, or 2.

In order to achieve the above object, an organic optoelectronic device containing the above organic semiconductor mixture according to the present invention includes a substrate, an electrode module arranged at the substrate and provided with a first electrode and a second electrode, and an active layer disposed between the first electrode and the second electrode. Materials for the active layer include at least one of the organic semiconductor mixtures mentioned above. At least one of the first electrode and the second electrode is transparent or semi-transparent.

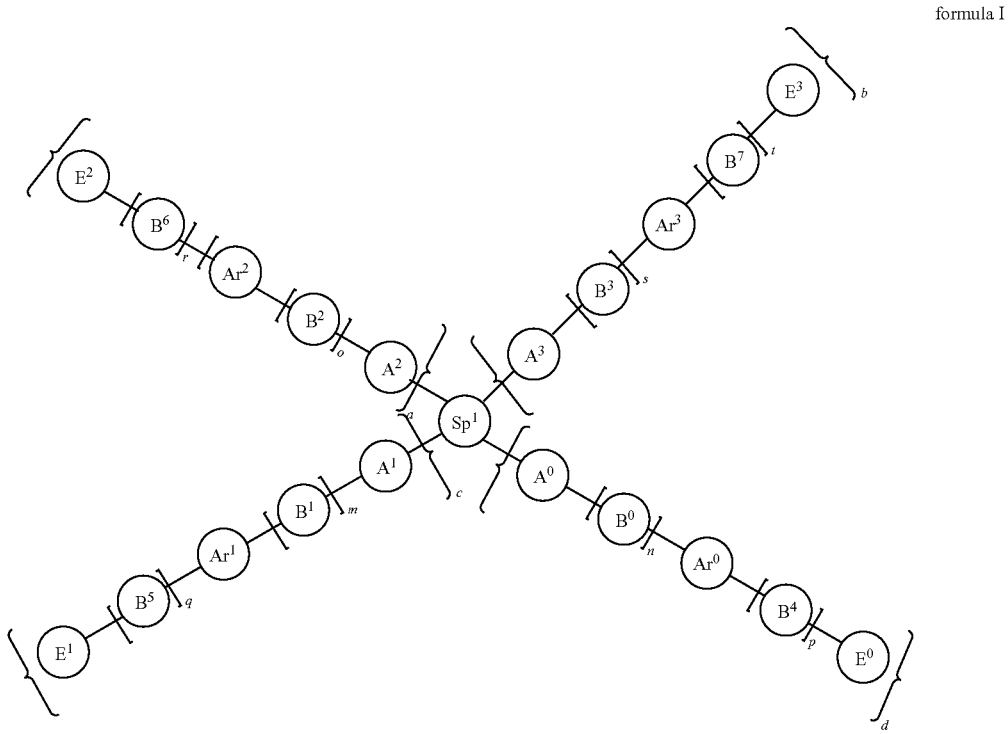

Figure 3A:
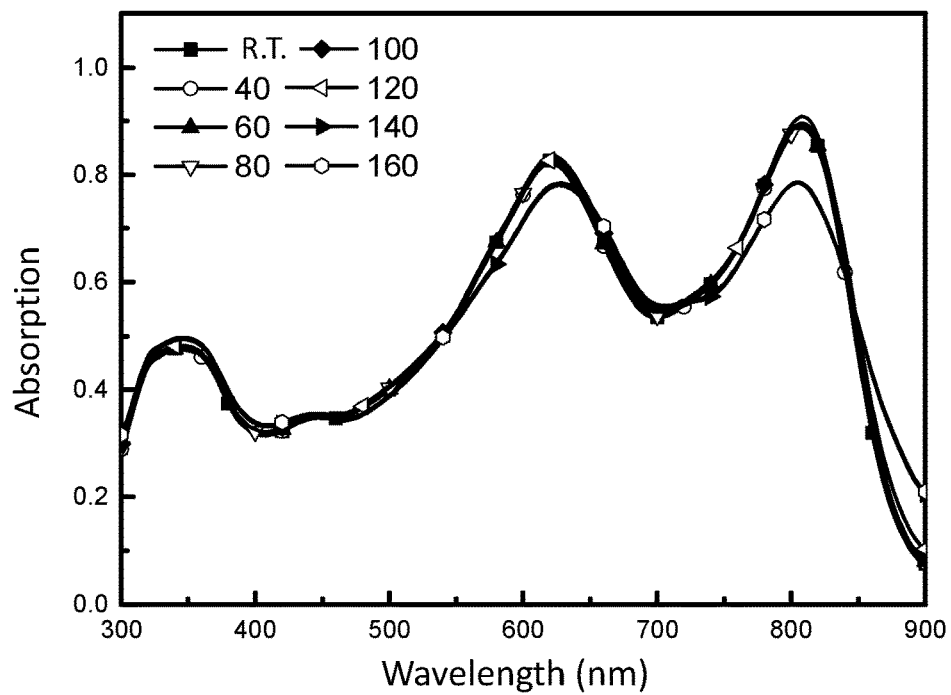
Figure 3B:
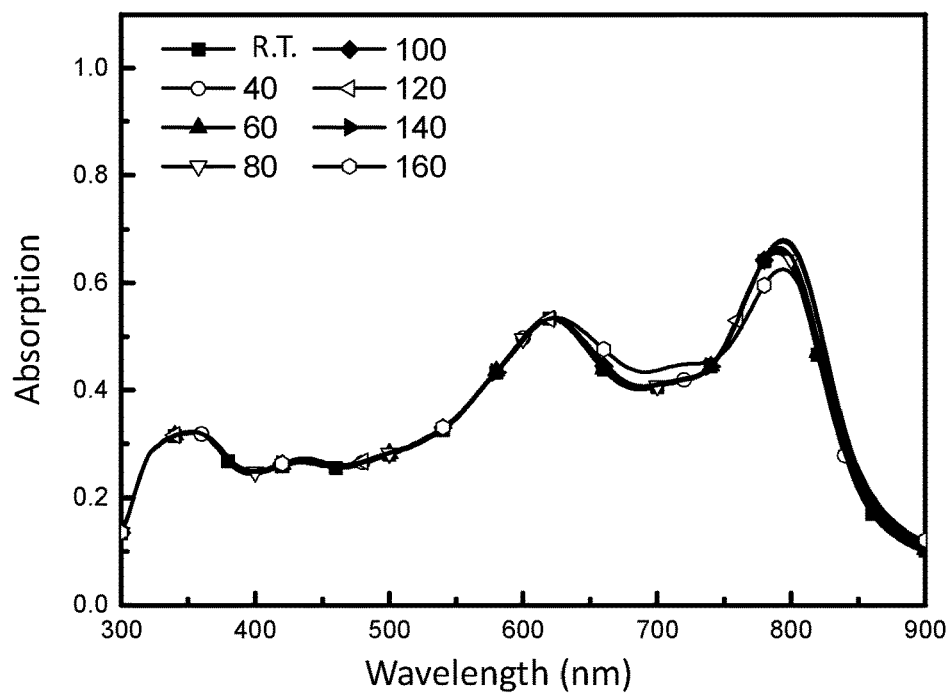
Figure 4A:
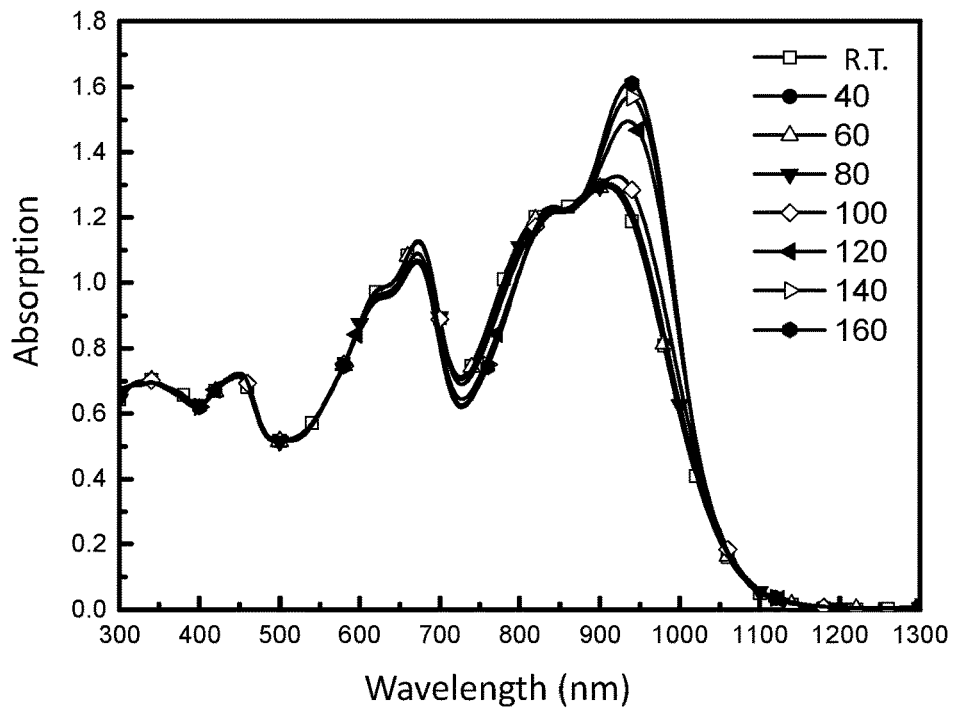
Figure 4B:
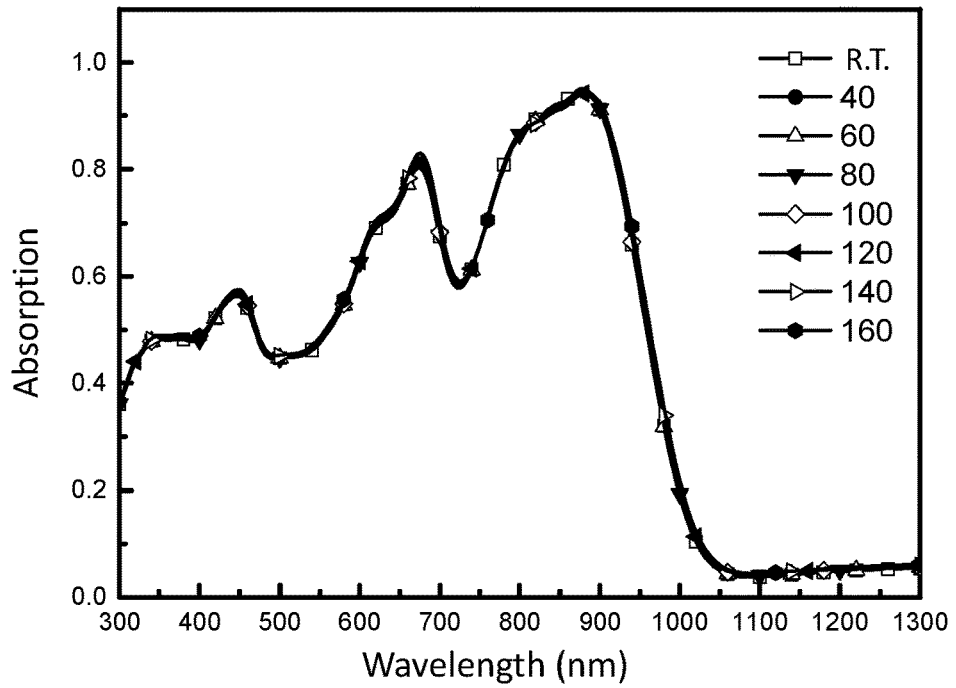
Figure 5A:
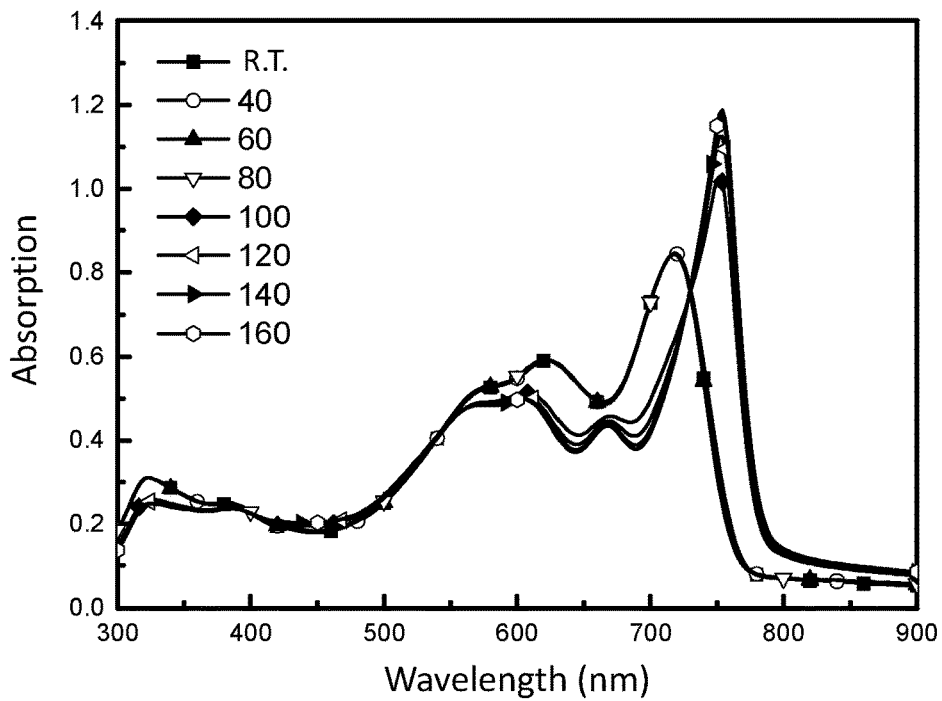
Figure 5B:
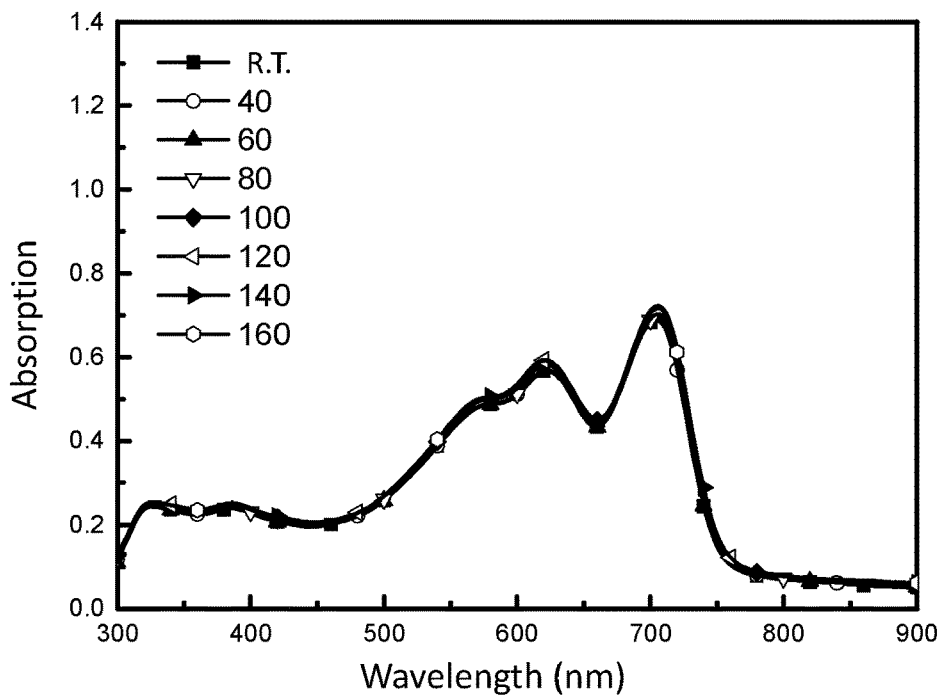
Figure 5C:
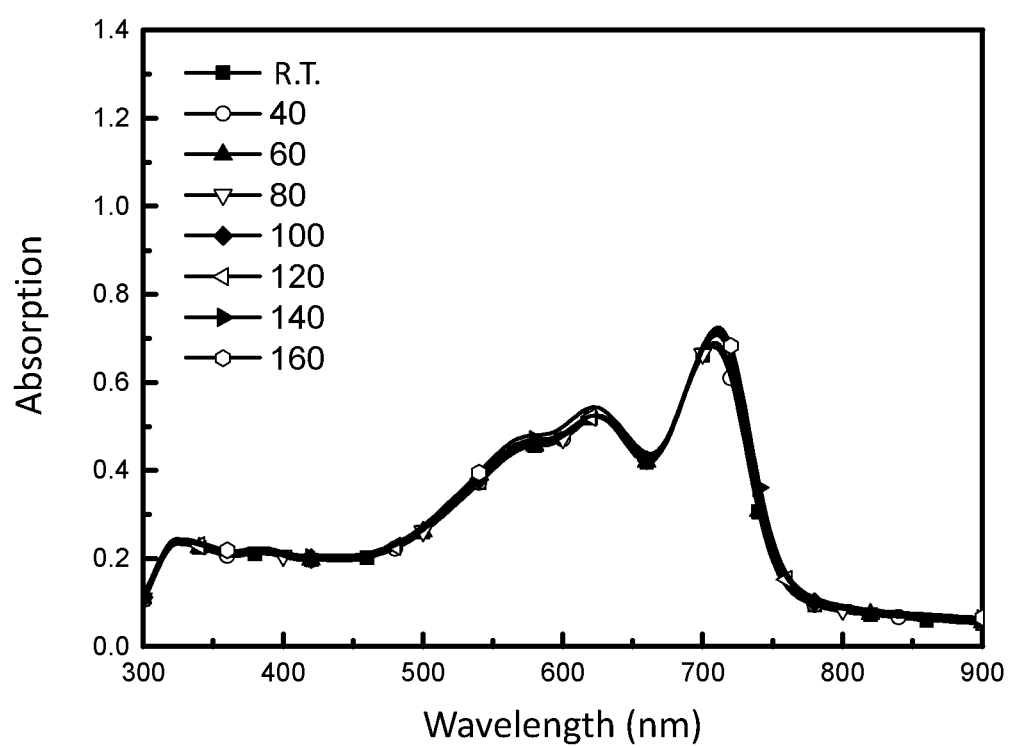

formula I $SP^1$ is selected from the group consisting of a vinyl group, a phenyl ring, an electron donating group, a substituted or unsubstituted monocyclic heteroaryl group containing 5 to 20 ring atoms, and a substituted or unsubstituted polycyclic heteroaryl group containing 5 to 20 ring atoms. $Ar^0$-$Ar^3$ are substituted fused polycyclic heteroaryl groups containing 5-35 ring atoms. $A^0$-$A^3$ are monocyclic or polycyclic heteroaryl groups containing 5-20 ring atoms and at least one electron-withdrawing group. $B^0$-$B^7$ are selected from the FIG. 3A-3B are spectra showing test results of different embodiments of an organic optoelectronic device according to the present invention;

FIG. 4A-4B are spectra showing test results of different embodiments of an organic optoelectronic device according to the present invention; and FIG. 5A-5C are spectra showing test results of different embodiments of an organic optoelectronic device according to the present invention.

DETAILED DESCRIPTION OF THE INVENTION

In order to learn features and functions of the present invention more clearly, please refer to the following embodiments and related descriptions.

An organic semiconductor mixture according to the present invention includes a n-type organic semiconductor compound and a p-type organic semiconductor compound. The n-type organic semiconductor compound includes a center unit $SP^1$ connected with at least two non-fullerene monomers to form a structure with a plurality of non-fullerene monomers which provides not only similar light absorption of non-fullerene, better thermal stability as well as mechanical properties but also solves problems such as phase separation or compatibility with other polymers during use of polymer acceptors.

Preparation of the present organic semiconductor mixture can be achieved by a method described in the literature or well known by people skilled in the art. The method is further described in the following embodiments.

In the above organic semiconductor mixture, the n-type organic semiconductor compound is represented by formula I:

cyclic heteroaryl groups containing 5-20 ring atoms and at least one electron-withdrawing group; $B^0$-$B^7$ are selected from the group consisting of a vinyl group, a phenyl ring, an electron donating group, a substituted or unsubstituted monocyclic heteroaryl group containing 5 to 20 ring atoms, and a substituted or unsubstituted polycyclic heteroaryl group containing 5 to 20 ring atoms; $E^0$-$E^3$ are monocyclic or polycyclic heteroaryl groups containing 5-20 ring atoms and at least one electron-withdrawing group, defined as different from the $SP^1$ group; a, b, c, and d are 0 or 1 and a+b+c+d>2; and m, n, o, p, q, r, s, and t are 0, 1, or 2.

The term "electron donating group" should be understood as an atom or group that delivers electron to another group in the same compound or in another compound. The term "electron withdrawing group" should be understood as an atom or group that draws electron from another group in the same compound or in another compound. The above definitions can also refer to International Union of Pure and Applied Chemistry, Compendium of Chemical Technology, Gold Book, Version 3.0.1., page 477, and 480. The electron withdrawing group used in the present invention is selected from the group consisting of halogen group, carbonyl group, cyano group, carboxyl group, nitro group, and ester group well known by people skilled in the art.

The group $SP^1$ in the n-type semiconductor compound represented by formula I is preferably selected from the following group.

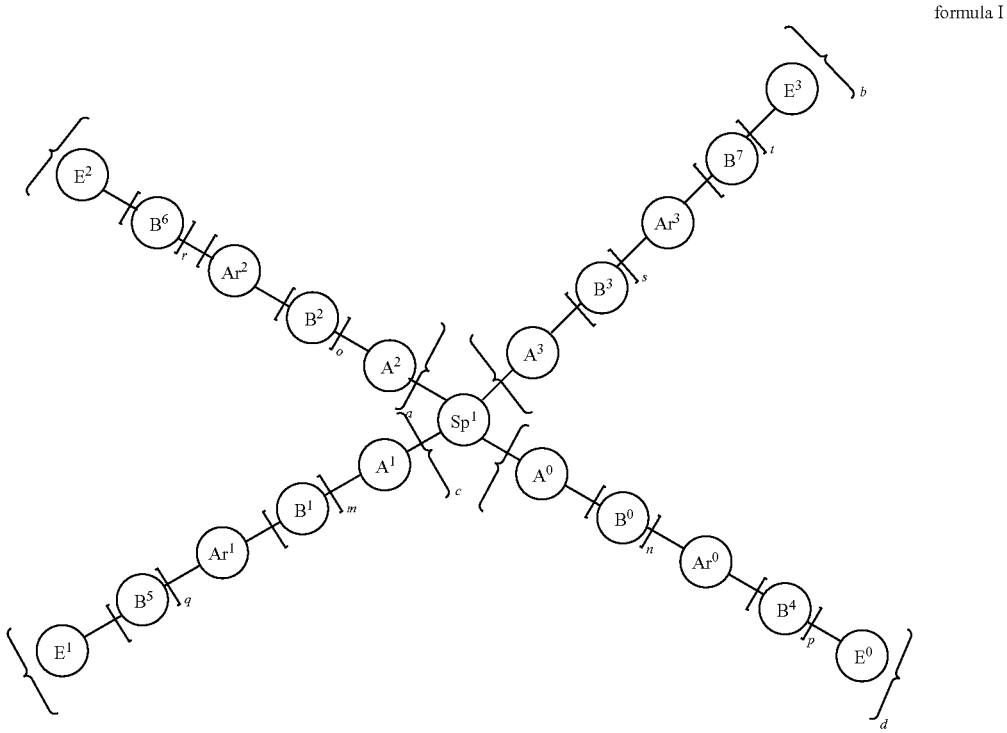

formula I wherein $SP^1$ is selected from the group consisting of a vinyl group, a phenyl ring, an electron donating group, a substituted or unsubstituted monocyclic heteroaryl group containing 5 to 20 ring atoms, and a substituted or unsubstituted polycyclic heteroaryl group containing 5 to 20 ring atoms; $Ar^0$-$Ar^3$ are substituted fused polycyclic heteroaryl groups containing 5-35 ring atoms; $A^0$-$A^3$ are monocyclic or poly-

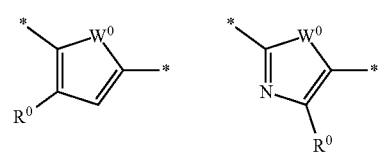

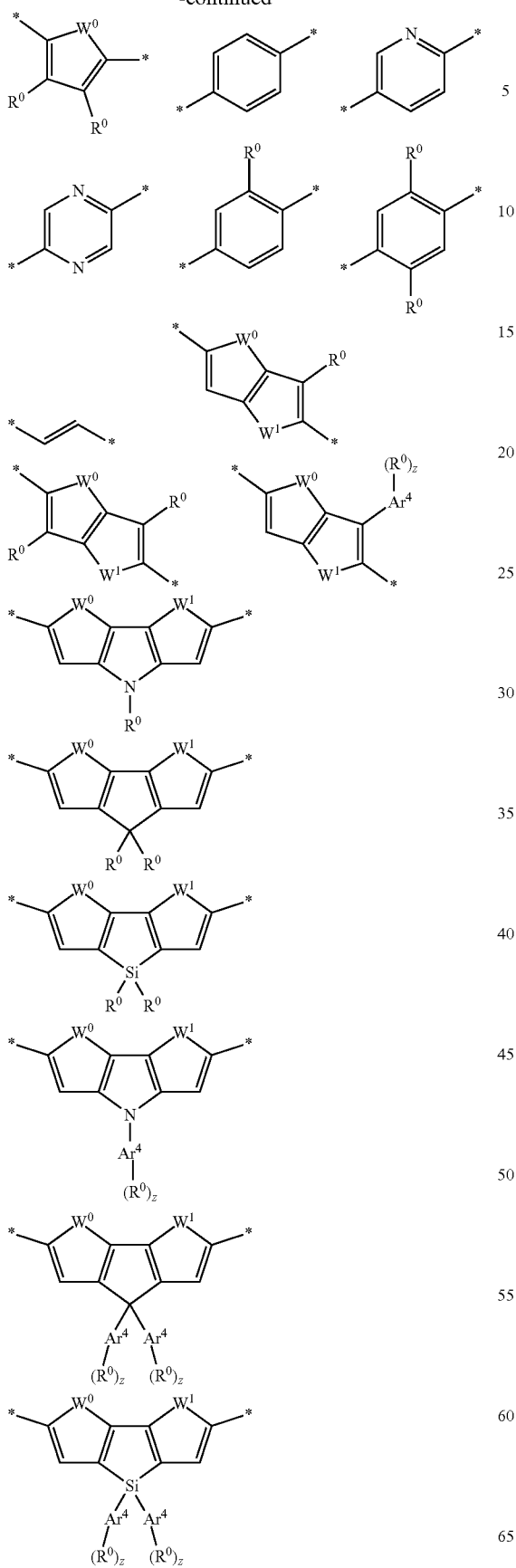
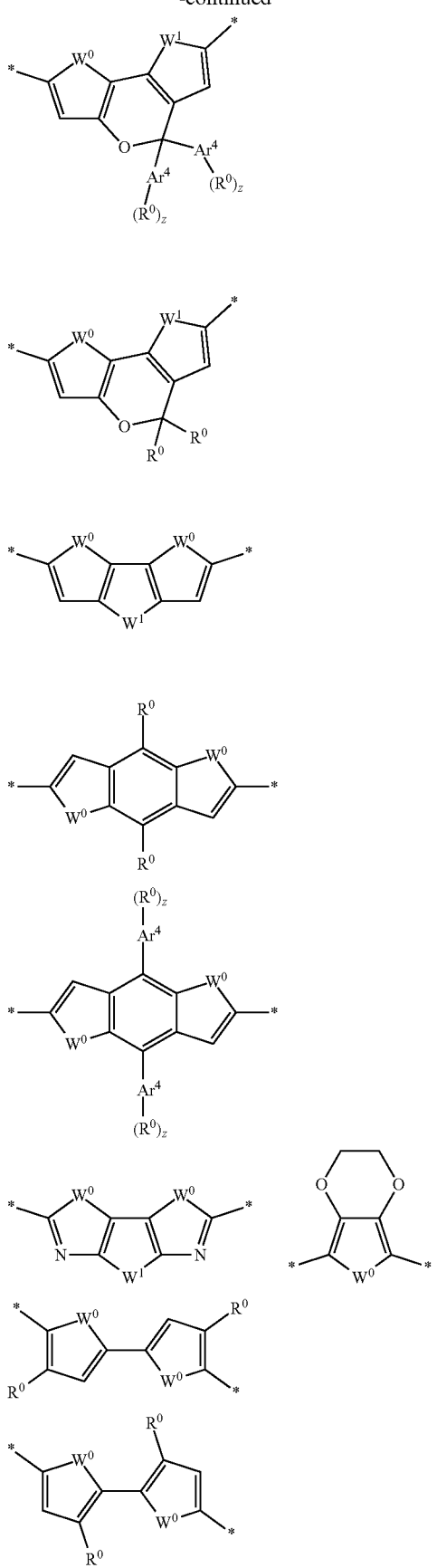

-continued

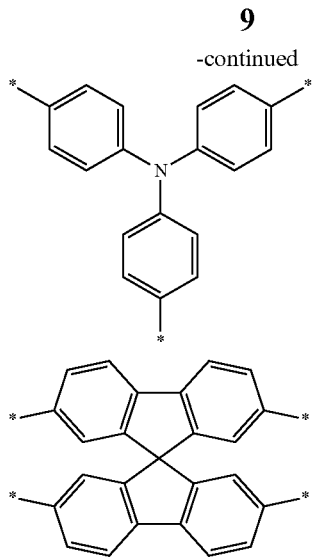

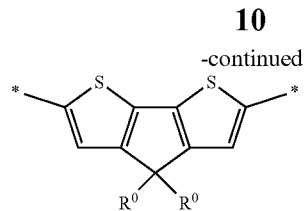

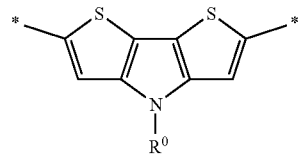

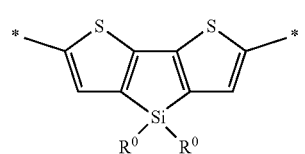

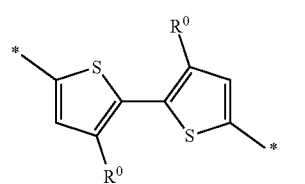

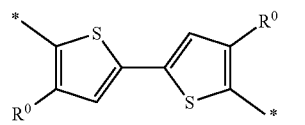

wherein $W^0$ and $W^1$ is oxygen (O), sulfur (S), selenium (Se), or tellurium (Te); z is an integer selected from 0 to 5.

$Ar^4$ is aromatic group or heteroaryl group containing 5 to 20 ring atoms, monocyclic or polycyclic, randomly containing a fused ring, unsubstituted or substituted with at least one halogen atom; and $R^0$ is selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group.

The group $SP^1$ of the compound represented by formula I is preferably selected from the following group:

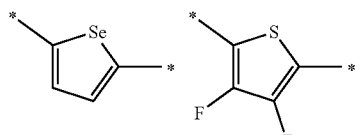

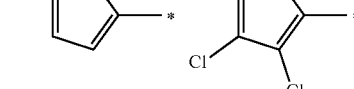

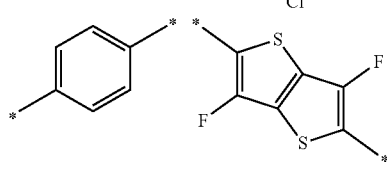

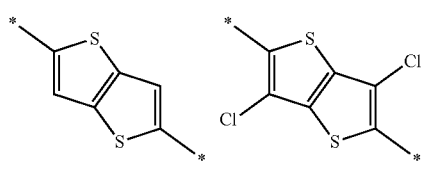

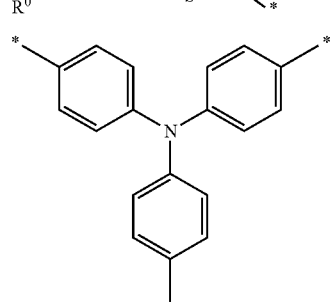

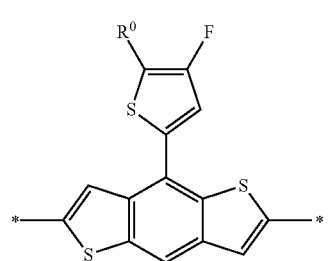

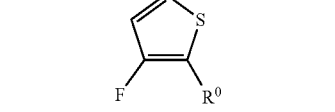

-continued

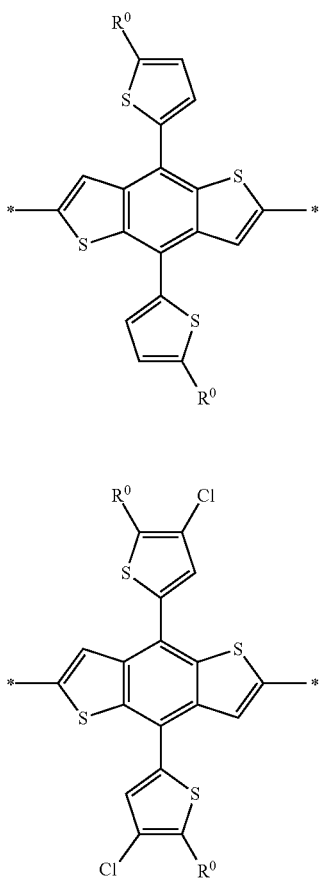

Each of the groups Ar⁰, Ar¹, Ar² and Ar³ of the compound represented by formula I is preferably selected from the following group:

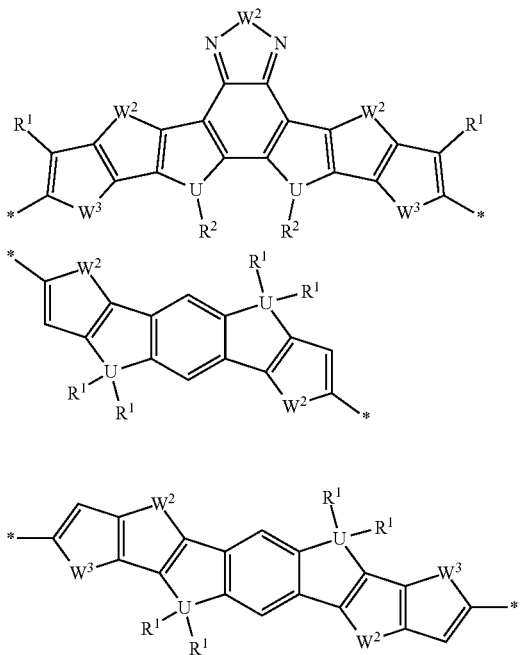

-continued

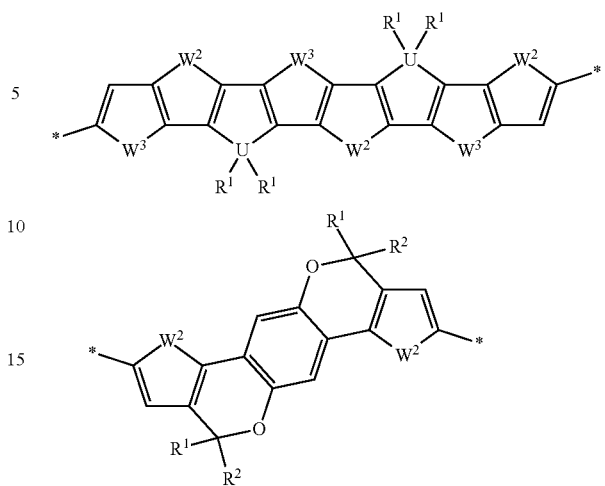

wherein $W^2$ and $W^3$ are selected from O, S, Se, or Te;

U is selected from nitrogen (N), carbon (C) or silicon (Si); and $R^1$ and $R^2$ are selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, C3-C30 keto-substituted alky, C1-C30 phenyl-ring-substituted alkyl, and C1-C30 heteroaryl-substituted alkyl group.

The groups Ar⁰, Ar¹, Ar² and Ar³ of the compound represented by formula I are preferably selected from the followings.

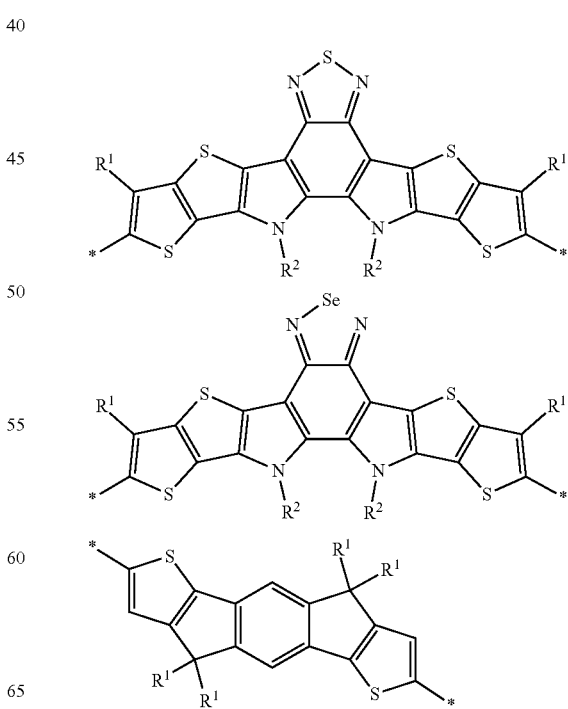

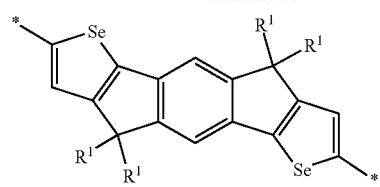
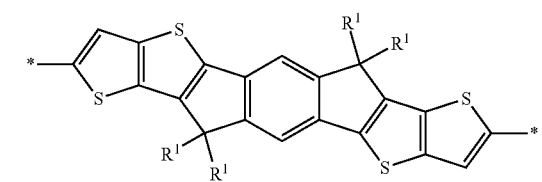
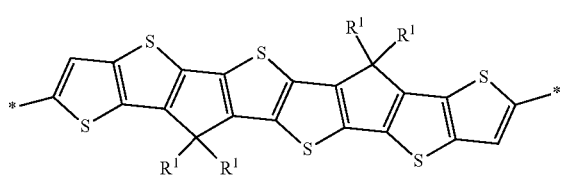
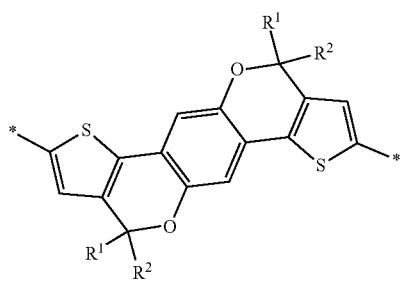
The groups $A^0$, $A^1$, $A^2$ and $A^3$ of the compound represented by formula I are preferably selected from the followings.
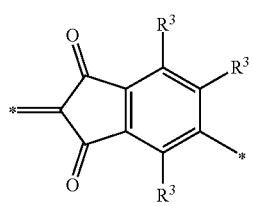
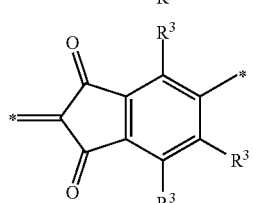
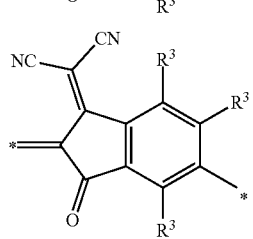
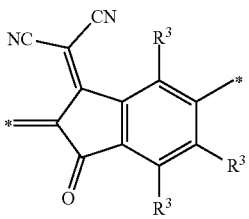
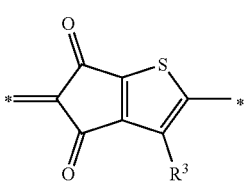
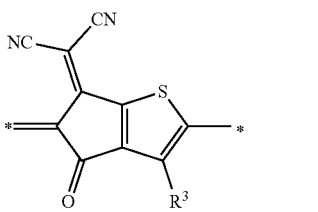
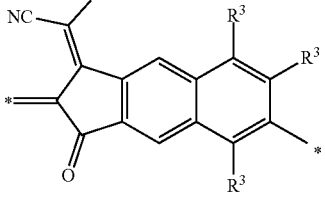
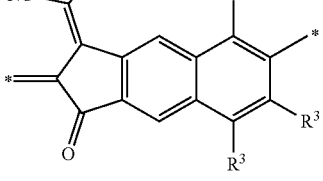
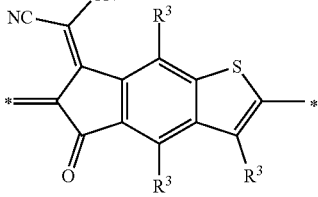
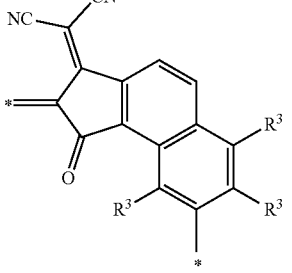

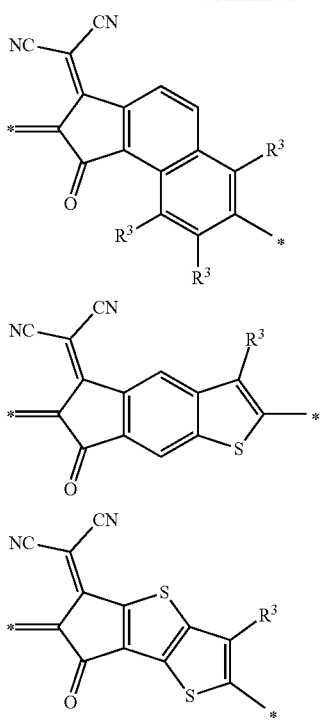

wherein R³ is selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group.

The groups B⁰-B⁷ of the compound represented by formula I are preferably selected from the followings.

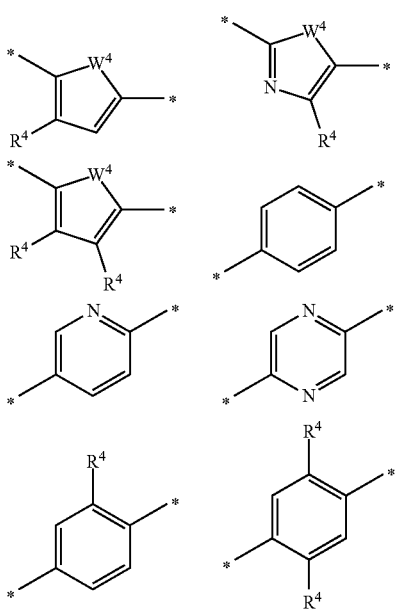

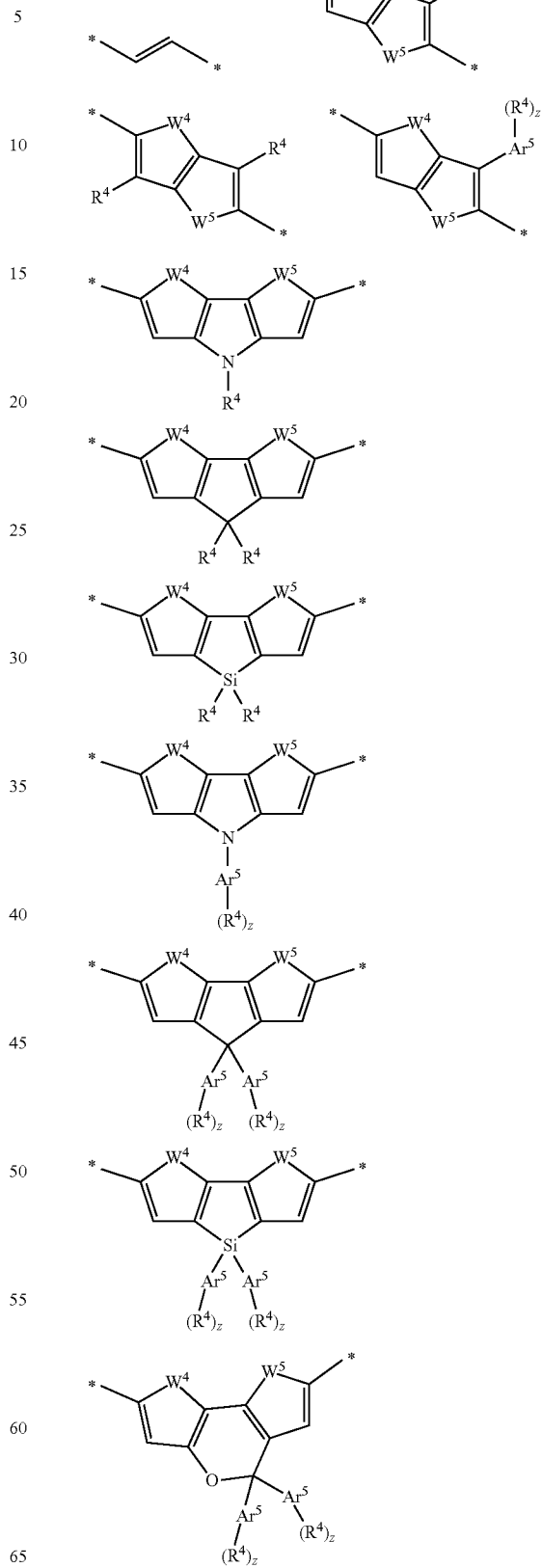

-continued

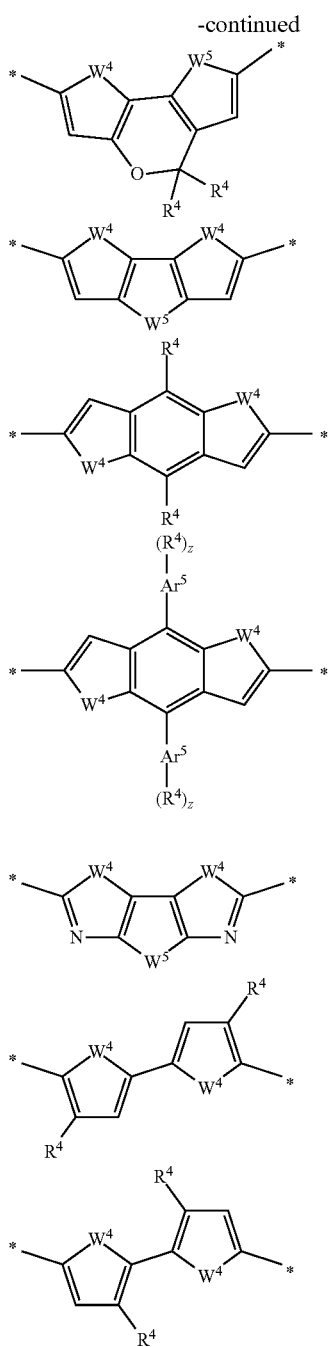

wherein $W^4$ and $W^5$ are selected from O, S, Se, or Te;
z is an integer selected from 0 to 5;
Ar$^5$ is aromatic group or heteroaryl group containing 5 to 20 ring atoms, monocyclic or polycyclic, randomly containing a fused ring, unsubstituted or substituted with at least one halogen atom; and
R$^4$ is selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group.

The groups $B^0$-$B^7$ of the compound represented by formula I are preferably selected from the followings.

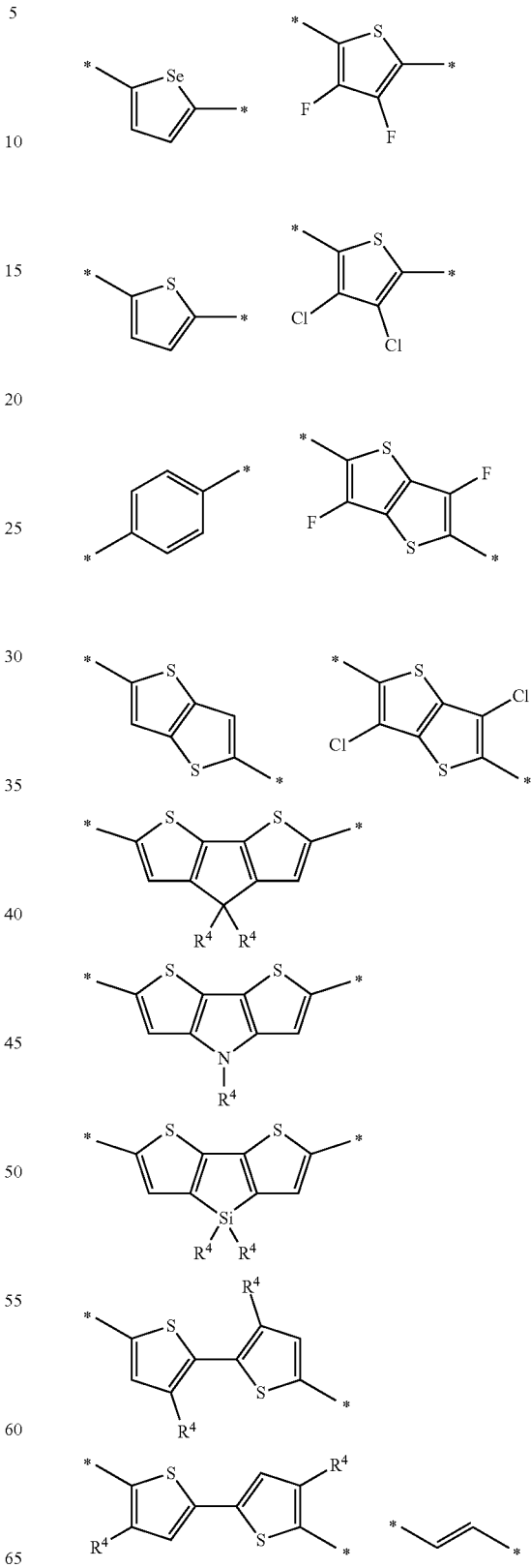

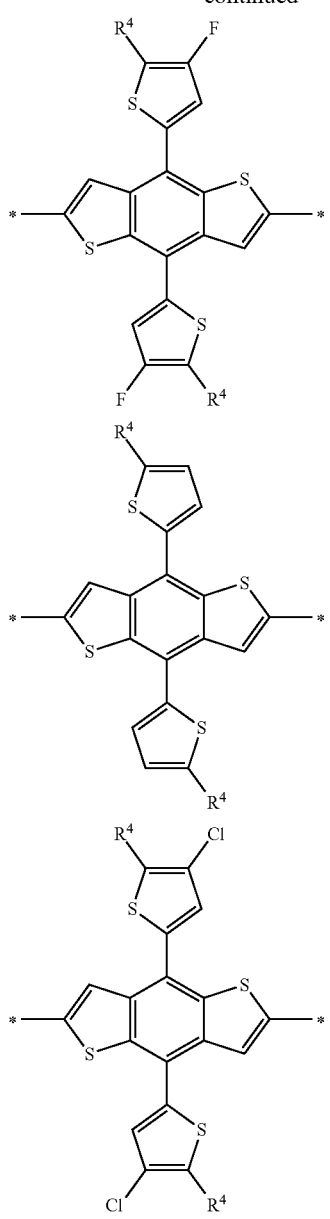
The groups $E^0$-$E^3$ of the compound represented by formula I are preferably selected from the followings.
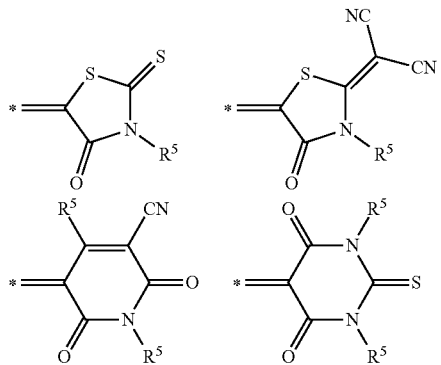
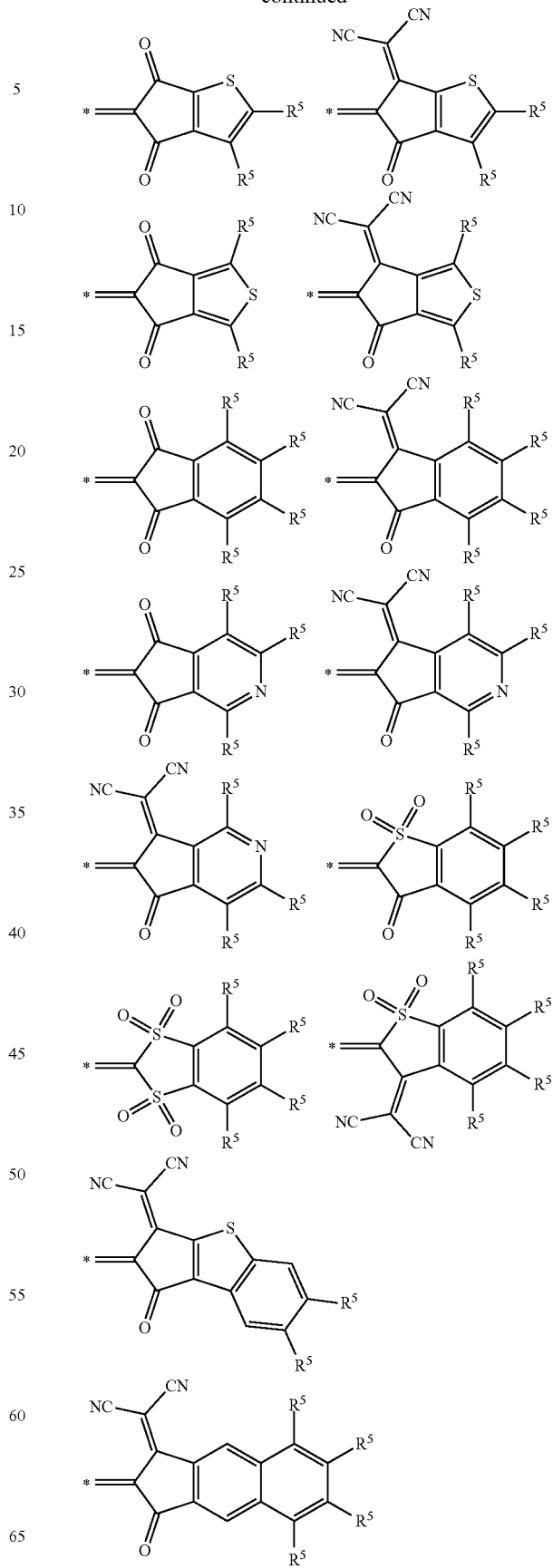

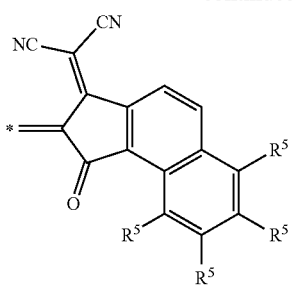
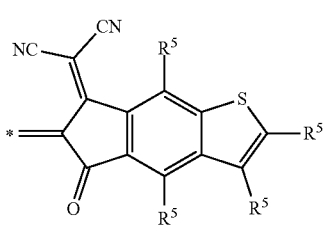
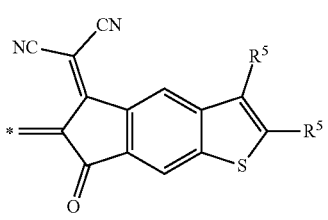
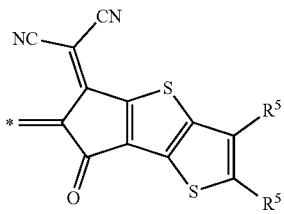

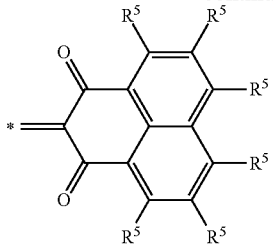
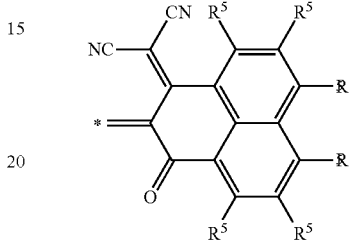
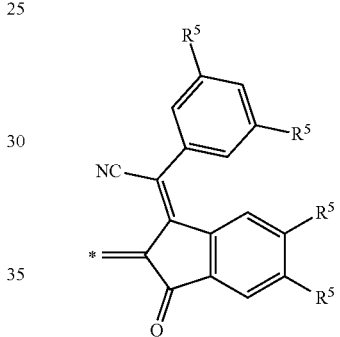

wherein $R^5$ is selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group.

In the organic semiconductor mixture, the p-type organic semiconductor compound is a conjugated polymer which includes at least one acceptor unit and at least one donor unit. The p-type organic semiconductor compound is represented by formula II:

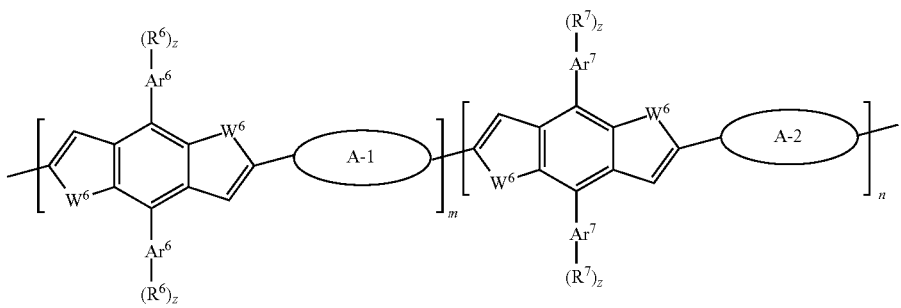

formula II wherein A-1 and A-2 are substituted or unsubstituted polycyclic heteroaryl groups containing 5 to 35 ring atoms and also electron withdrawing groups;

$W^6$ is selected from O, S, and Se;

z is an integer selected from 0 to 5;

$Ar^6$ and $Ar^7$ are aromatic groups or heteroaryl groups containing 5 to 20 ring atoms, monocyclic or polycyclic, randomly containing a fused ring, unsubstituted or substituted with at least one halogen atom; and $R^6$ and $R^7$ are selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group; and m+n=1, $0 < m \leq 1$, $0 \leq n < 1$.

The group A-1 of the compound represented by formula II is preferably selected from the followings.

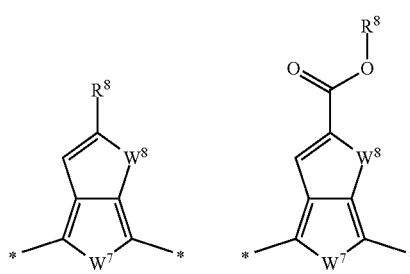

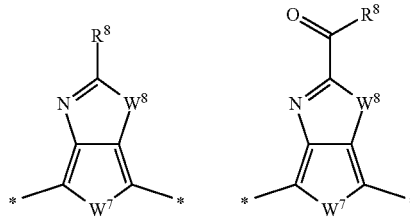

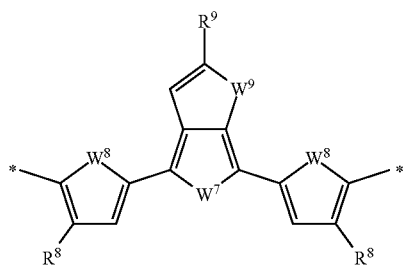

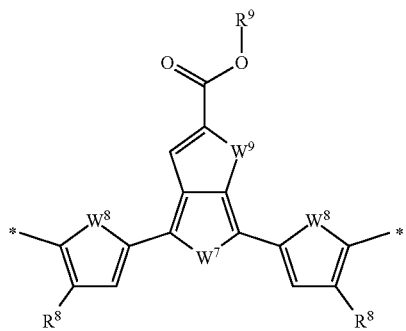

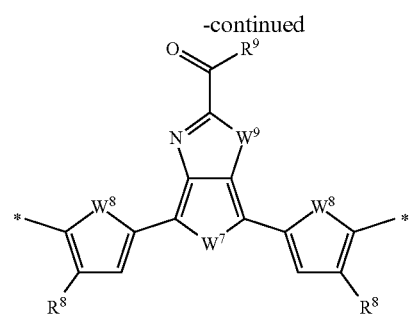

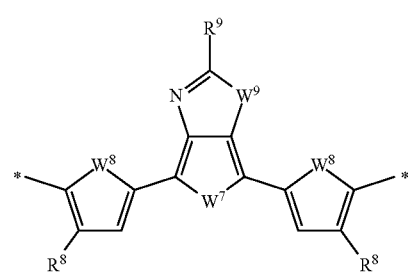

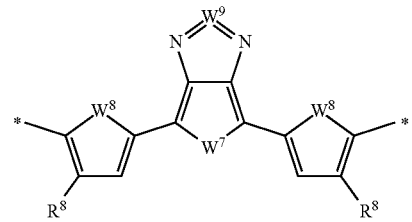

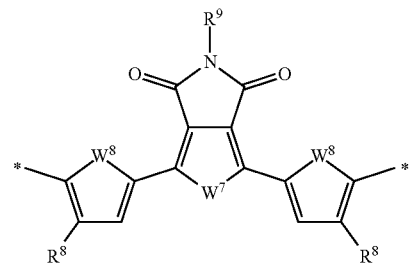

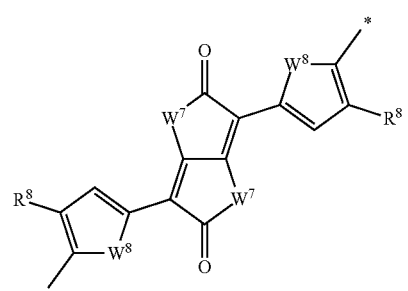

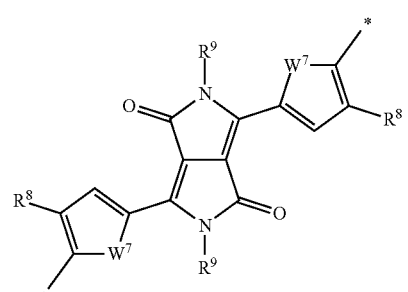

-continued
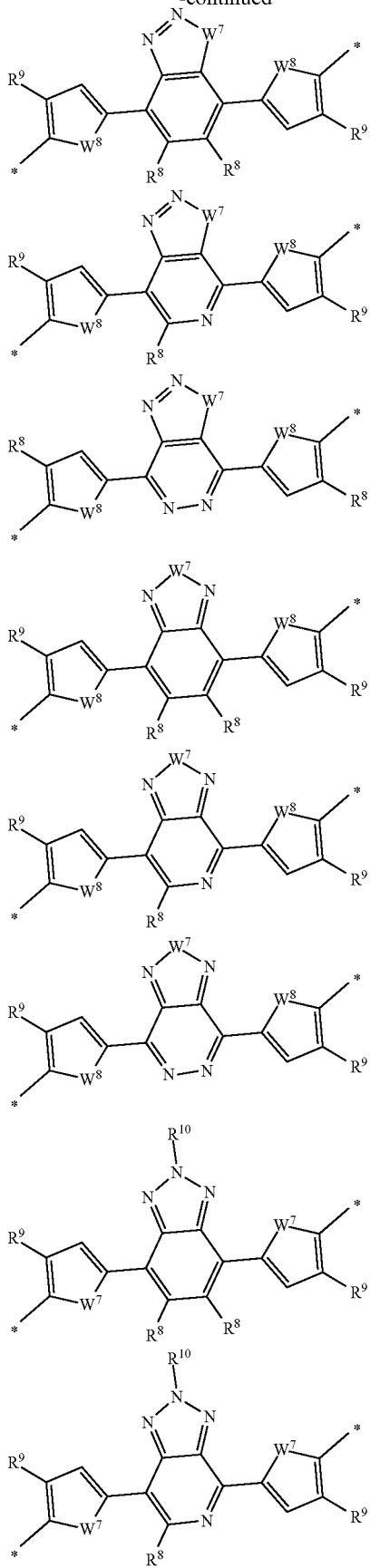
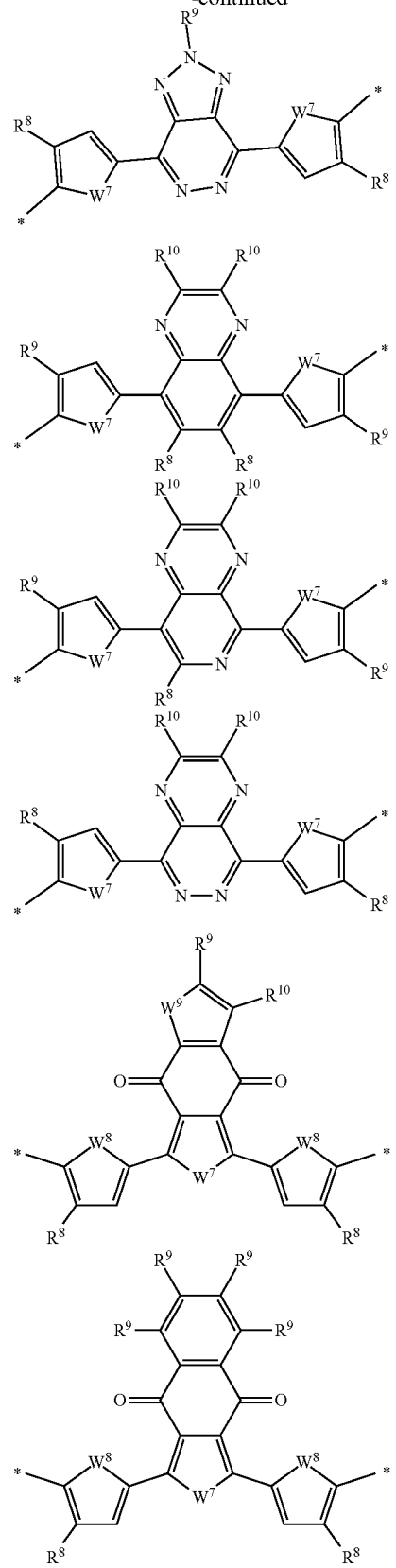
wherein $W^7$, $W^8$, and $W^9$ are selected from O, S, Se, and Te; and R[8], R[9], and R[10] are respectively selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group.

The group A-2 of the compound represented by formula II is preferably selected from the followings.

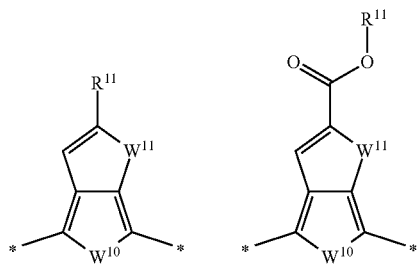

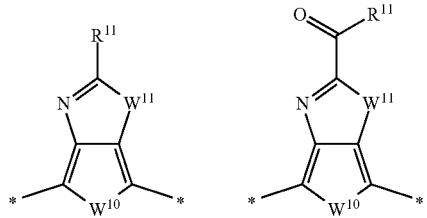

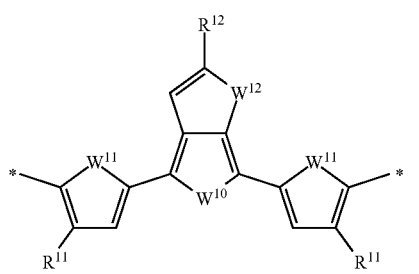

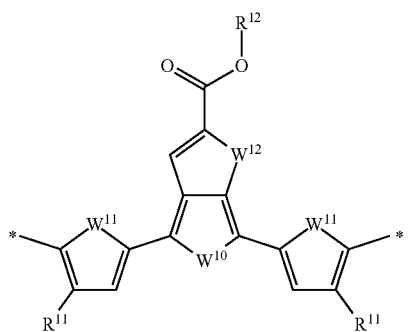

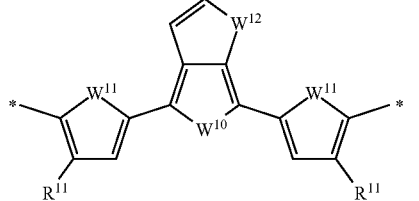

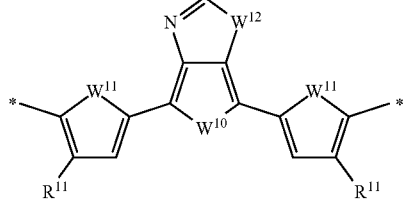

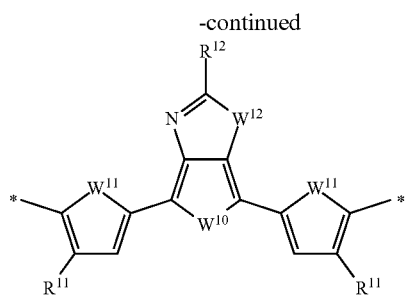

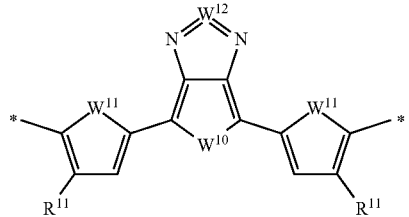

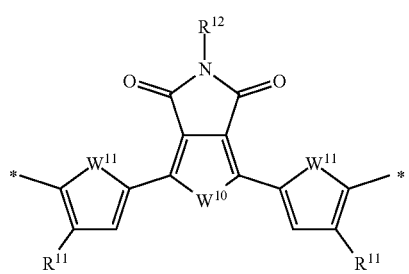

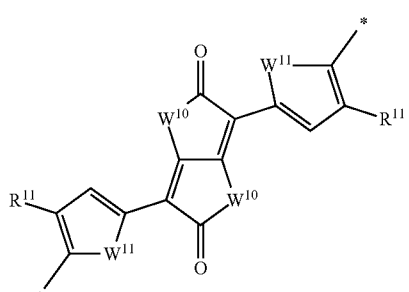

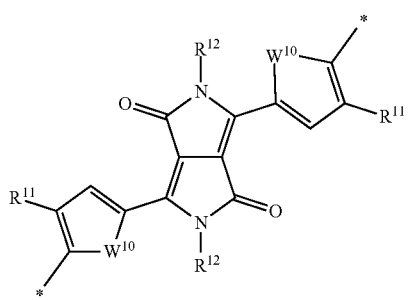

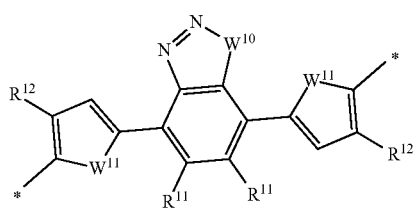

-continued
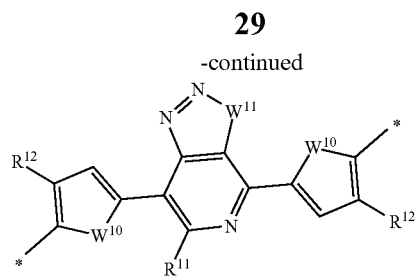
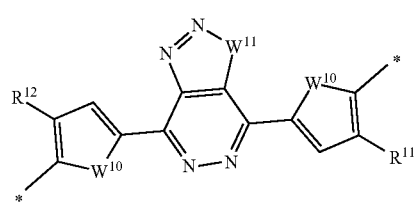
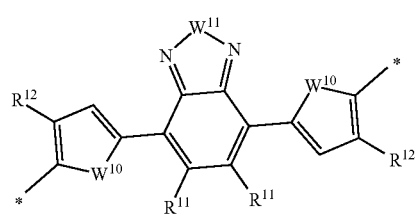
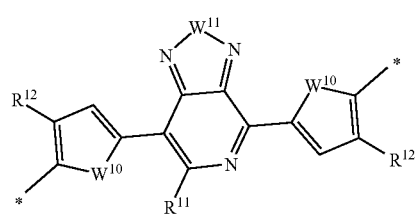
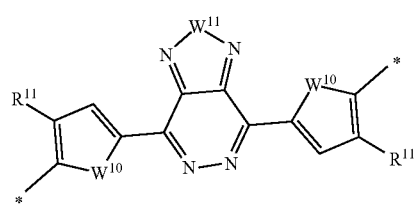
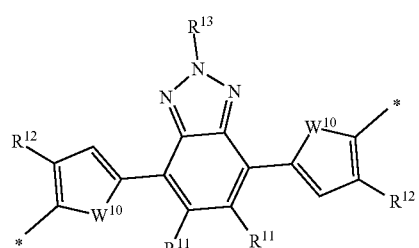
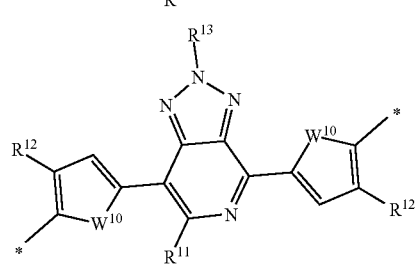
-continued
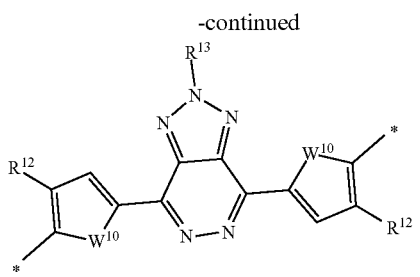
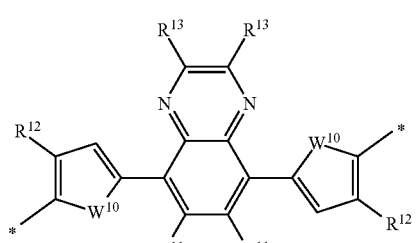
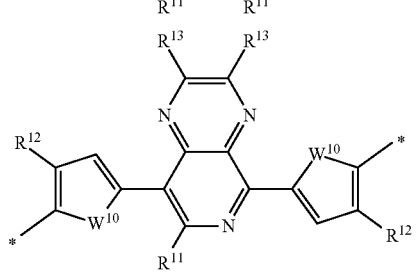
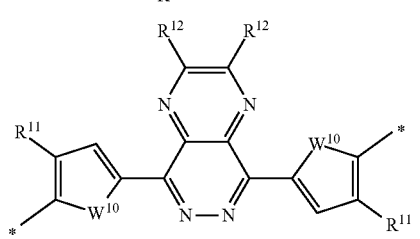
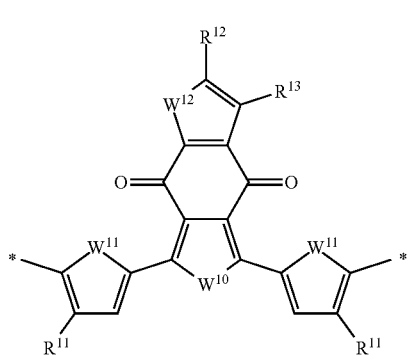
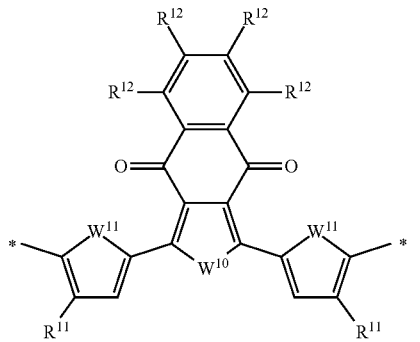

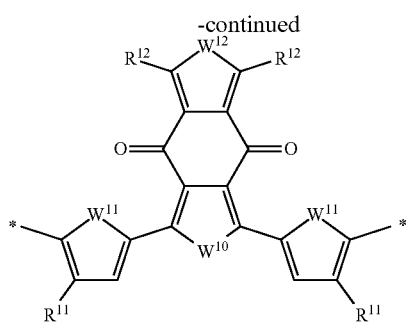

wherein $W^{10}$, $W^{11}$, and $W^{12}$ are selected from O, S, Se, and Te; and $R^{11}$, $R^{12}$, and $R^3$ are respectively selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group.

The p-type organic semiconductor compound is preferably selected from the following repeating units.

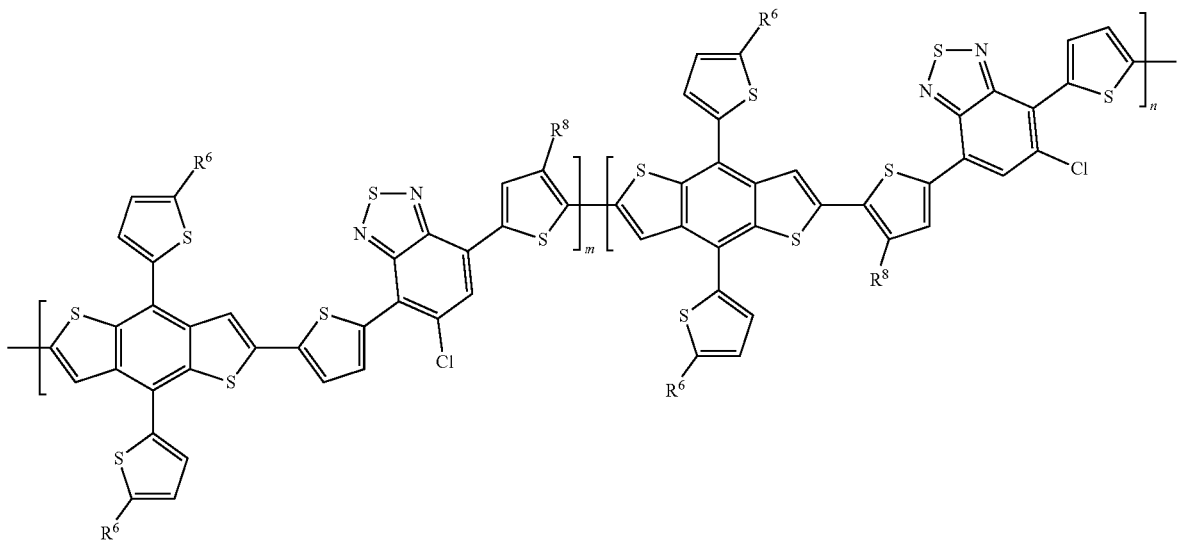

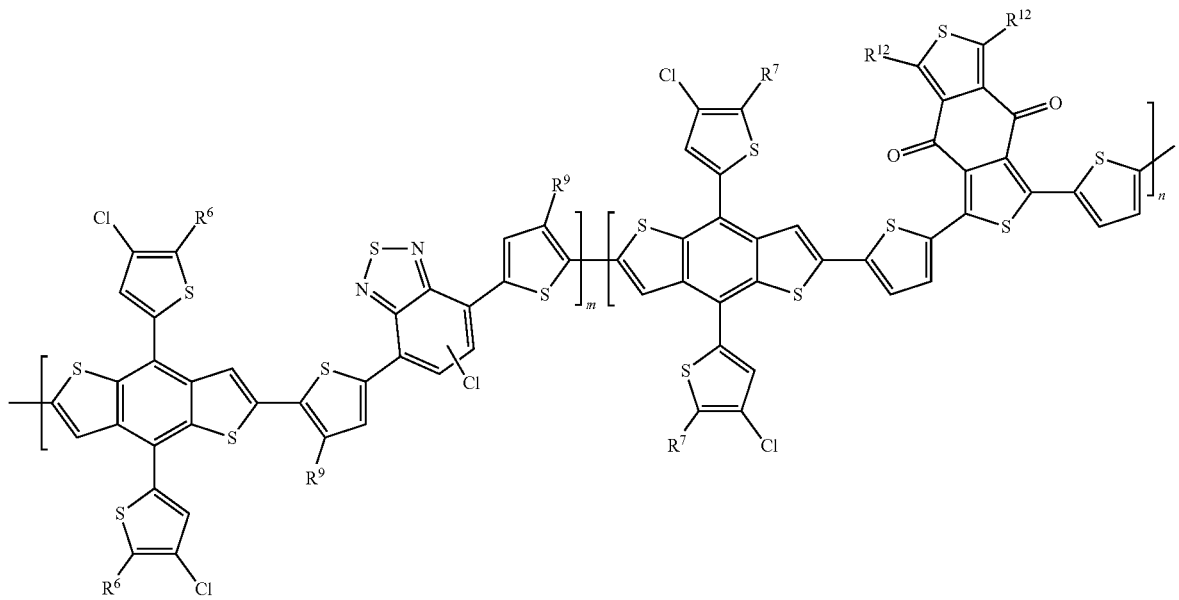

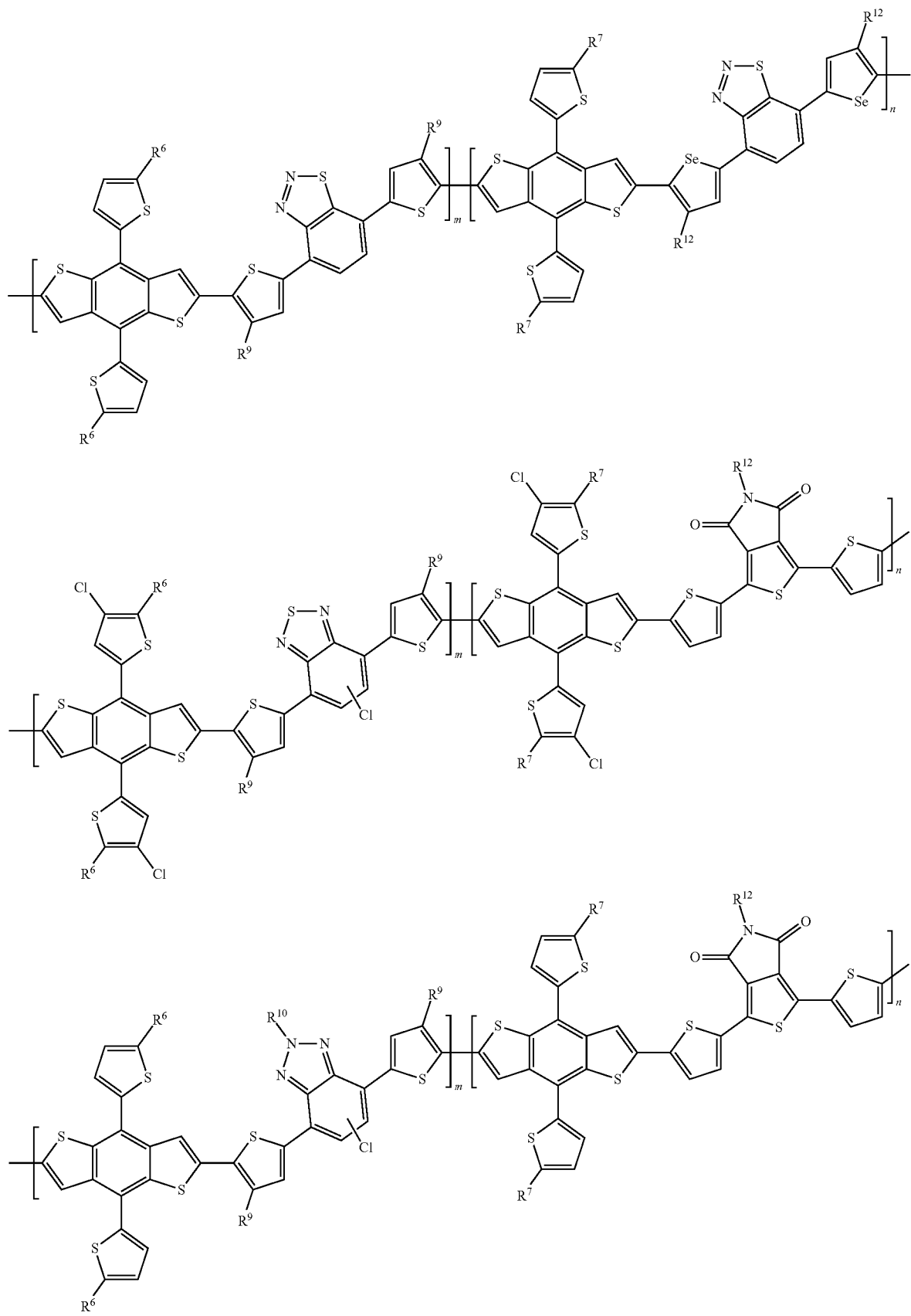

-continued
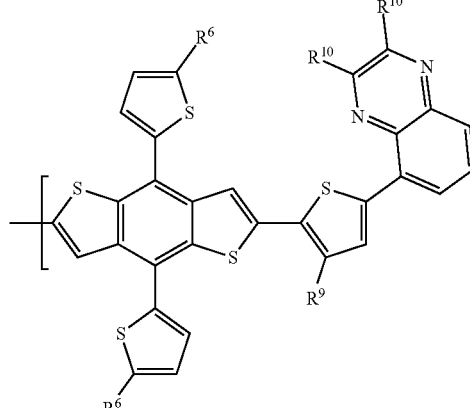
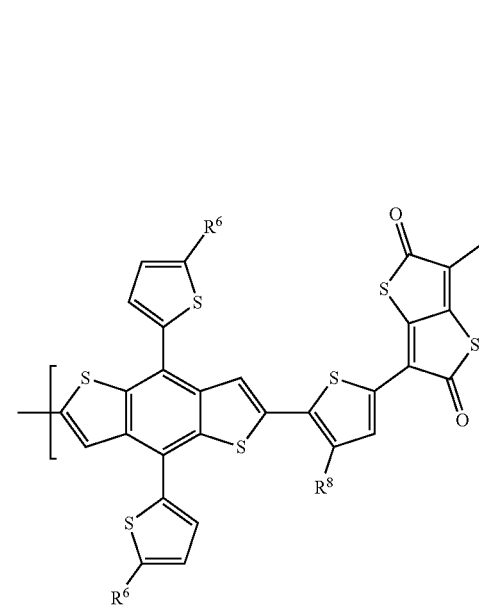

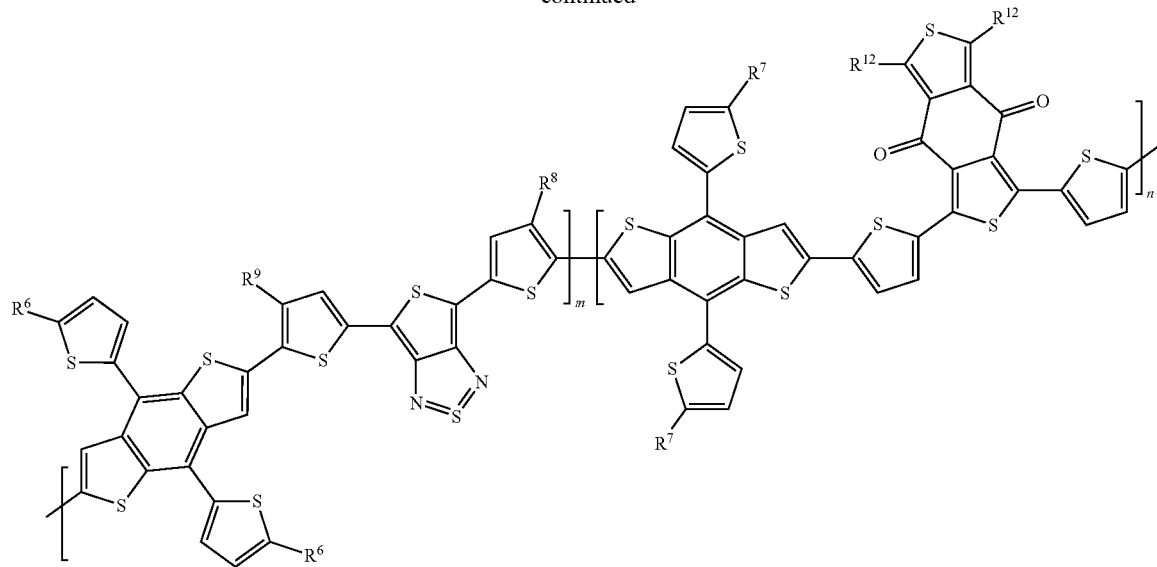

wherein $R^6$-$R^{12}$ are respectively selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group; and m+n=1, 0<m≤1, and 0≤n<1.

In the following embodiments, ingredients and synthesis methods of the organic semiconductor mixture according to the present invention are described.

Synthesis of Intermediate I-1

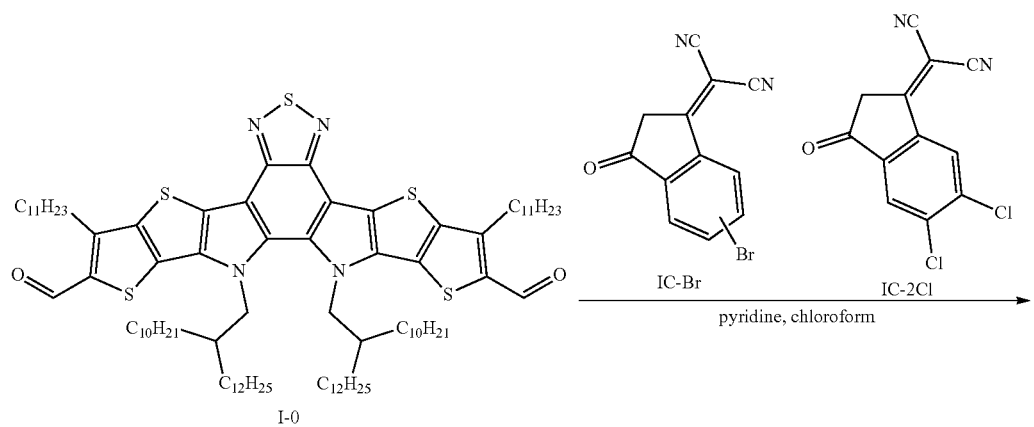

-continued

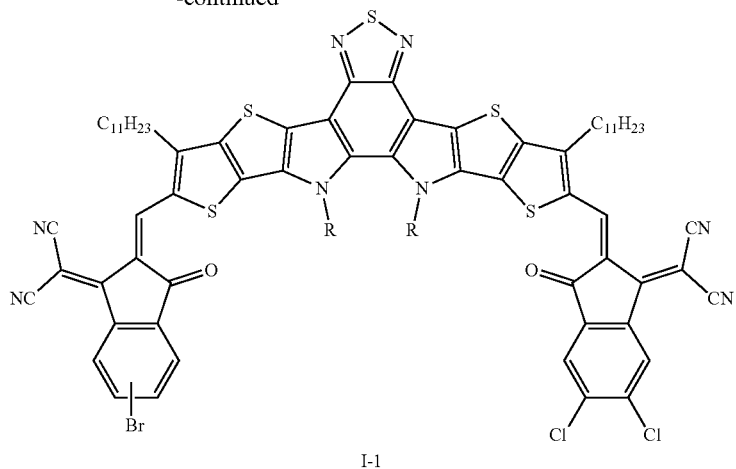

I-1

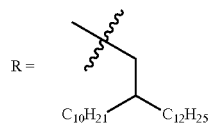

Place a 100 mL two-necked flask into an oven, bake at 100° C. for 30 minutes and degas chloroform 30 minutes for later use. Put 1.00 g (0.678 mmol) I-0, 0.370 g (1.354 mmol, 2 equiv.) IC-Br (2-[5(6)-Bromo-3-oxo-2,3-dihydro-1H-inden-1-ylidene]malononitrile), 0.356 g (1.354 mmol, 2 equiv.) IC-2C1 (2-(5,6-Dichloro-3-oxo-2,3-dihydro-1H-inden-1-ylidene)malononitrile), and degassed 30 mL chloroform into a 100 mL two-necked flask and then introduce argon gas into the two-necked flask. Add 1 mL pyridine into the two-necked flask and immerse the two-necked flask in a 60° C. oil bath to react for an hour. After completion of the reaction, precipitate product in 100 mL MeOH and filter to get solid. Wash the solid with acetone and ethyl acetate and purify with column chromatography with toluene/heptane=½ as eluent. Collect product, remove the organic solvents by rotary evaporation, and vacuum dry for 16 hours to get 0.558 g bright bluish black solid product with a yield rate of 41.7%. $^1$H NMR spectrum (600 MHz, CDCl$_3$) of the product: δ 9.17 (d, 2H), 8.85 (s, 1H), 8.79-8.80 (m, 1H), 7.95 (s, 1H), 7.85-7.88 (m, 1H), 7.78-7.80 (m, 1H), 4.75-4.77 (m, 4H), 3.21-3.24 (m, 4H), 2.10-2.11 (m, 2H), 1.88 (s, 4H), 1.57 (s, 4H), 0.83-1.26 (m, 126H).

Synthesis of Intermediate I-2

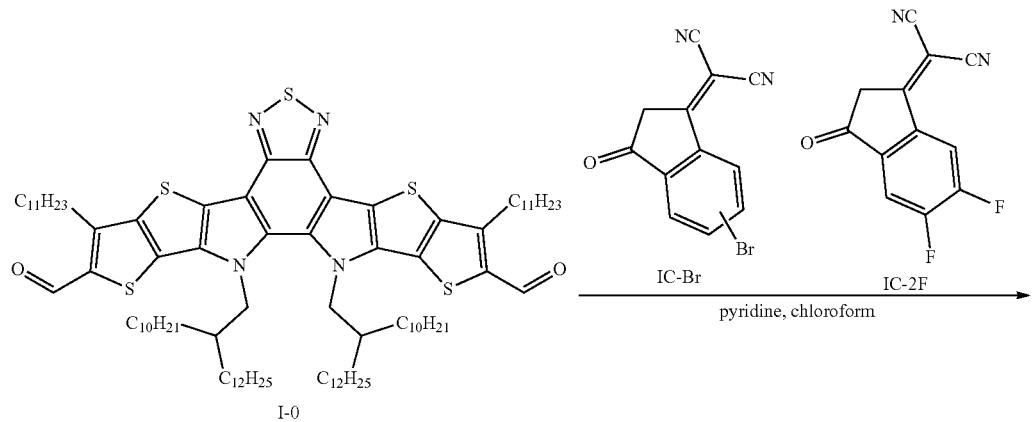

-continued

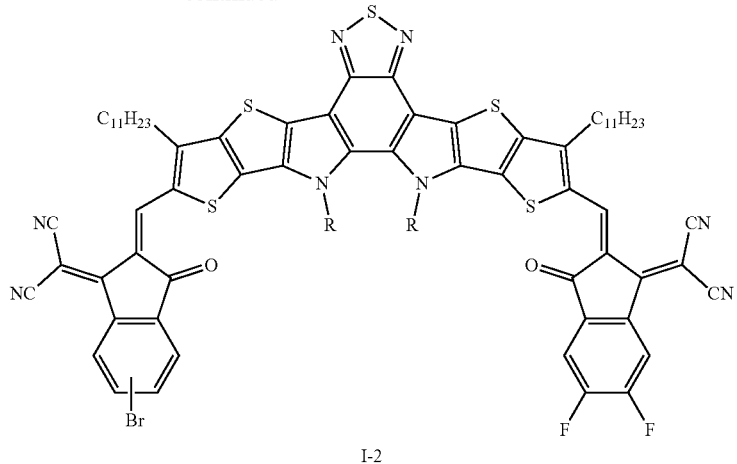

I-2

R = 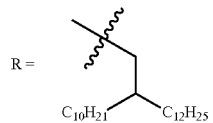

Place a 100 mL two-necked flask into an oven, bake at 100° C. for 30 minutes and degas chloroform 30 minutes for later use. Put 0.402 g (0.272 mmol) I-0, 0.148 g (0.543 mmol, 2 equiv.) IC-Br, 0.125 g (0.543 mmol, 2 equiv.) IC-2F, and degassed 12 mL chloroform into a 100 mL two-necked flask and then introduce argon gas into the two-necked flask. Add 0.41 mL pyridine into the two-necked flask and immerse the two-necked flask in a 60° C. oil bath to react for an hour. After completion of the reaction, precipitate product in 100 mL MeOH and filter to get solid. Wash the solid with acetone and ethyl acetate and purify with column chromatography with toluene/heptane=½ as eluent. Collect product, remove the organic solvents by rotary evaporation, and vacuum dry for 16 hours to get 0.245 g bright bluish black solid product with a yield rate of 39.1%. $^1$H NMR spectrum (600 MHz, CDCl$_3$) of the product: δ 9.13 (s, 2H), 8.80 (s, 1H), 8.51-8.54 (m, 1H), 7.87 (d, 1H), 7.79 (d, 1H), 7.68-7.71 (m, 1H), 4.77-4.78 (m, 4H), 3.19-3.21 (m, 4H), 2.15 (s, 2H), 1.87 (s, 4H), 0.82-1.60 (m, 130H).

Synthesis of Intermediate I-4

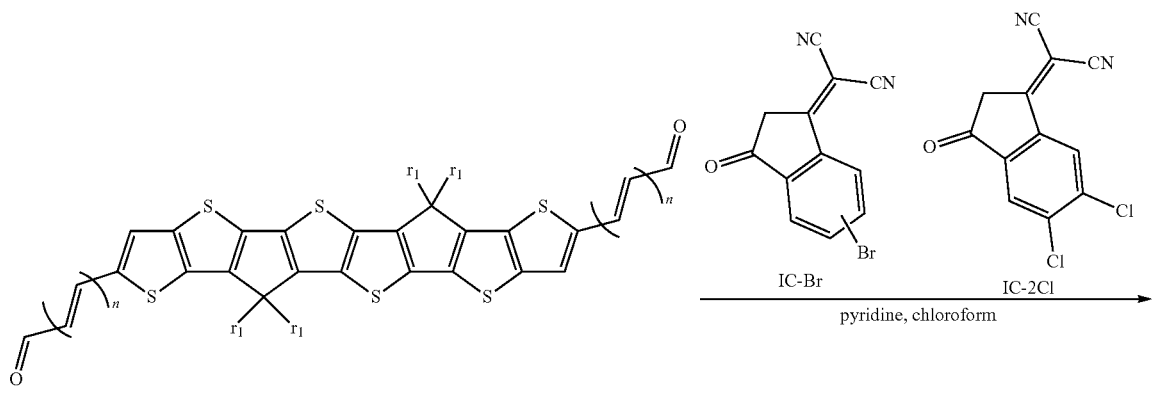

I-3

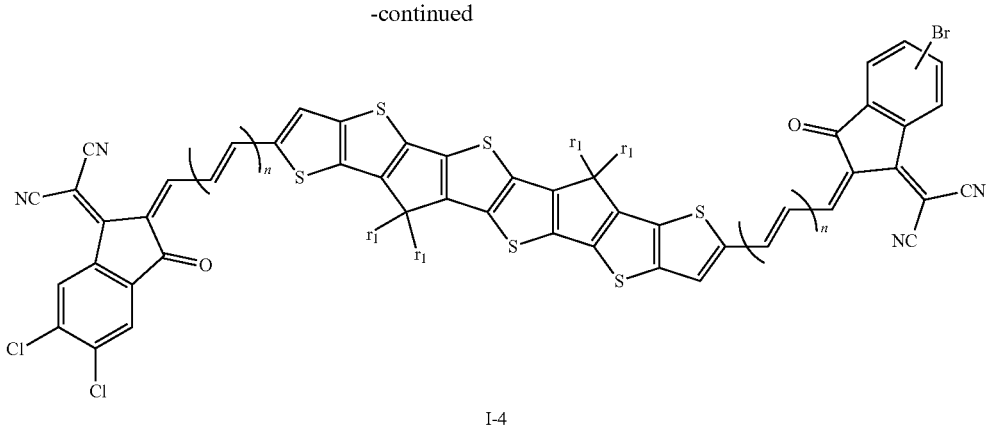

I-4

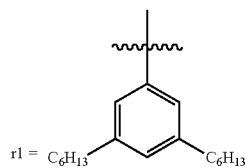

Place a 100 mL two-necked flask into an oven, bake at 100° C. for 30 minutes and degas chloroform 30 minutes for later use. Put 1.042 g (0.683 mmol) I-3, 0.372 g (1.366 mmol, 2 equiv.) IC-Br, 0.360 g (1.366 mmol, 2 equiv.) IC-2Cl, and 16 mL degassed chloroform into a 100 mL two-necked flask and then introduce argon gas into the two-necked flask. Add 0.52 mL pyridine into the two-necked flask and react at room temperature for 0.5 hour. After completion of the reaction, precipitate product in 50 mL MeOH and filter to get solid. Wash the solid with acetone and ethyl acetate and purify with column chromatography with toluene/heptane=2/1 as eluent. Collect product, remove the organic solvents by rotary evaporation, and vacuum dry for 16 hours to get 0.231 g grey black solid product with a yield rate of 16.7%. $^1$H NMR spectrum (600 MHz, CDCl$_3$) of the product: δ 8.79 (s, 1H), 9.74 (s, 1H), 8.48-8.54 (m, 2H), 8.41-8.44 (m, 2H), 7.88 (s, 1H), 7.82-7.85 (m, 1H), 7.70-7.72 (m, 1H), 7.62-7.63 (m, 2H), 7.47-7.55 (m, 2H), 6.94 (s, 8H), 6.81 (s, 16H), 2.52 (t, 32H), 1.52-1.60 (m, 32H), 1.21-1.28 (m, 96H), 0.78-0.82 (m, 48H).

Synthesis of Intermediate I-6

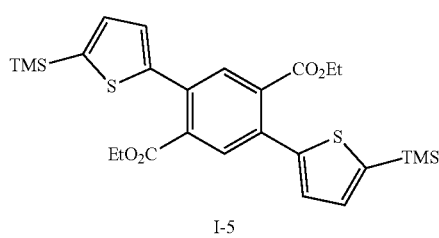

I-5

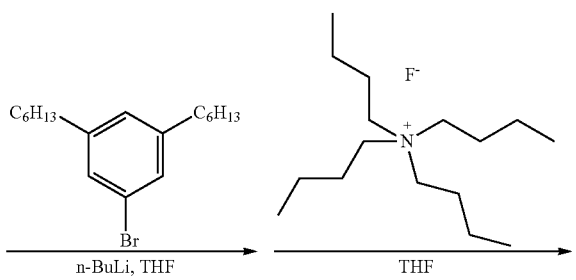

-continued

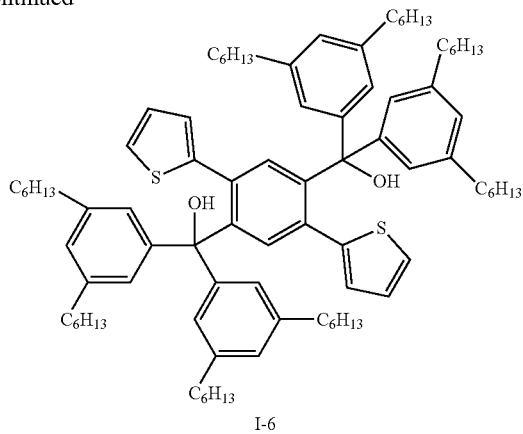

I-6

Place a 250 mL three-necked flask, a 100 mL two-necked flask and an addition funnel into an oven, bake at 100° C. for 2 hours and then take out and cool down to room temperature under vacuum. Add 10.41 g (32.0 mmol) 1-bromo-3,5-dihexylbenzene into the 250 mL three-necked flask, add 63 mL anhydrous tetrahydrofuran (THF), and stir with a magnetic stirrer. Add 14.4 mL (36.0 mmol) 2.5M n-Butyllithium into the addition funnel and slowly drop to the three-necked flask at −30° C. after the reaction bottle being cooled down to −30° C. Maintain reaction temperature between −30° C. and −40° C. to react for 40 minutes. Add 2.123 g (4.00 mmol) I-5 into the 100 mL two-necked flask with 53 mL dry THF, and stir with a magnetic stirrer until complete dissolution. After the three-necked flask being cooled down to −30° C., reagent in the two-necked flask is slowly pumped and added into the three-necked flask completely. Then the three-necked flask is warmed to room temperature to react for one hour, and the temperature of the three-necked flask is increased up to 60° C. to react for 18 hours. After completion of the reaction, alcohols and water are slowly added in order to quench the reaction until there is no more bubble generated. Remove the solvents by rotary evaporation and perform extraction three times with ethyl acetate/$H_2O$. Collect organic layer, add $MgSO_4$ for dehydration, and remove the solvent by rotary evaporation. A crude product obtained after the extraction is added with 65 mL THF and stirred with the magnetic stirrer until complete dissolving. Add 6.4 mL tetrabutylammonium fluoride (TBAF) and react for 30 minutes. After completion of the reaction, alcohols and water are slowly added to quench the reaction until there is no more bubble generated. Remove solvent by rotary evaporation and perform extraction three times with ethyl acetate/$H_2O$. Collect organic layer, add $MgSO_4$ for dehydration, and remove the solvent by rotary evaporation. Next perform column chromatography with an eluent of dichloromethane/Heptane=¼. Collect product, remove the organic solvents by rotary evaporation, and vacuum dry for 16 hours to get 1.83 g yellow sticky liquid (the product) with a yield rate of 35.8%. $^1$H NMR spectrum (600 MHz, $CDCl_3$) of the product: δ 7.11 (dd, 2H), 6.87 (s, 4H), 6.80 (s, 8H), 6.75 (s, 2H), 6.66 (dd, 2H), 6.08 (dd, 2H), 3.39 (s, 2H), 2.49 (t, 16H), 1.49-1.51 (m, 16H), 1.23-1.27 (m, 48H), 0.83-0.85 (m, 24H).

Synthesis of Intermediate I-7

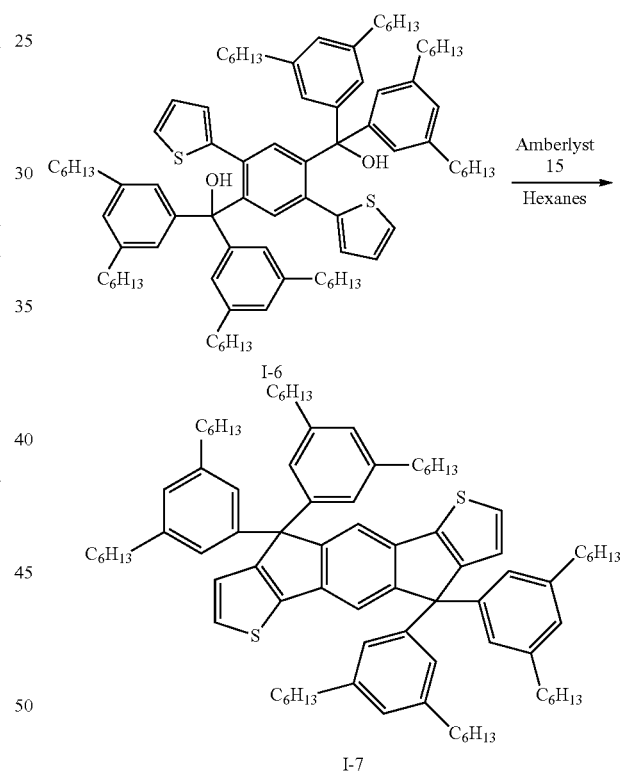

Add 6.216 g Amberlyst 15 and a magnet into a 250 mL two-necked flask A, heat at 100° C. and vacuum for 18 hours for later use. Place a 250 mL two-necked flask B into an oven, bake at 100° C. for 2 hours and then take out and cool down to room temperature under vacuum. Add 31 mL dry hexane into the two-necked flask A and purge with argon for 30 minutes. Add 1.554 g (1.214 mmol) I-6 into the 250 mL two-necked flask B. Then add 70 mL anhydrous hexane for complete dissolution and purge with argon for 30 minutes. At 0° C. pump solution in the two-necked flask B into the two-necked flask A and react at room temperature for 3 hours. After completion of the reaction, remove Amberlyst 15 from crude product by suction filtration. Collect filtrate and remove the solvents by rotary evaporation to get oily substance. Next use column chromatography for purification with an eluent of dichloromethane/heptane=½. Collect product, remove the organic solvent by rotary evaporation, and vacuum dry for 16 hours to get 1.35 g orange solid product with yield rate of 89.4%. ¹H NMR spectrum (600 MHz, CDCl₃) of the product: δ 7.37 (s, 2H), 7.20 (d, 2H), 6.93 (d, 2H), 6.87 (s, 4H), 6.83-8.85 (m, 8H), 2.46 (t, 16H), 1.49-1.50 (m, 16H), 1.25-1.28 (m, 48H), 0.71-0.89 (m, 24H).

Synthesis of Intermediate I-8

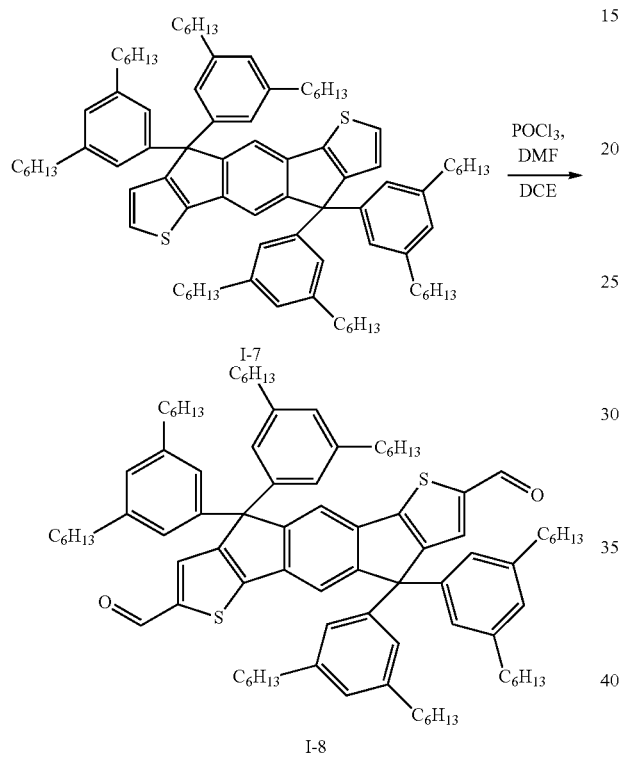

Place a 250 mL three-necked flask and a 100 mL two-necked flask into bake at 100° C. for 2 hours and then take out and cool down to room temperature under vacuum. Add 1.341 g, (1.08 mmol) I-7 into the 250 mL three-necked flask, then add 40 mL dichloroethane (DCE), stir with a magnetic stirrer, and purge with nitrogen for 30 minutes. Add 4.2 mL (54.0 mmol, 50 equiv.) anhydrous dimethylformamide (DMF) into the 100 mL two-necked flask, slowly add 0.6 mL (6.48 mmol, 6 equiv.) POCl₃ under ice bath, and stir with a magnetic stirrer for 30 min to form Vilsmeier-Haack reagent and color is changed into transparent-light yellow. Next pump the Vilsmeier-Haack reagent into the three-necked flask, heat to 60° C. and reflux to react for 18 hours. After completing reaction, cool down to room temperature and slowly add water to quench the reaction. Extract 3 times with dichloromethane/H₂O, collect organic layer, add magnesium sulfate for dehydration, and remove the solvent by rotary evaporation. Next use column chromatography for purification with an eluent of dichloromethane/heptane=1/1. Collect product, remove the organic solvents by rotary evaporation, and vacuum dry for 16 hours to get 1.32 g bright yellow solid product with yield rate of 94.2%. ¹H NMR spectrum (600 MHz, CDCl₃) of the product: δ 9.81 (s, 2H), 7.59 (s, 2H), 7.54 (s, 2H), 6.92 (s, 4H), 6.81 (s, 8H), 2.48 (t, 16H), 1.49-1.52 (m, 16H), 1.25-1.28 (m, 48H), 0.83-0.85 (m, 24H).

Synthesis of Intermediate I-9 and Compound 11

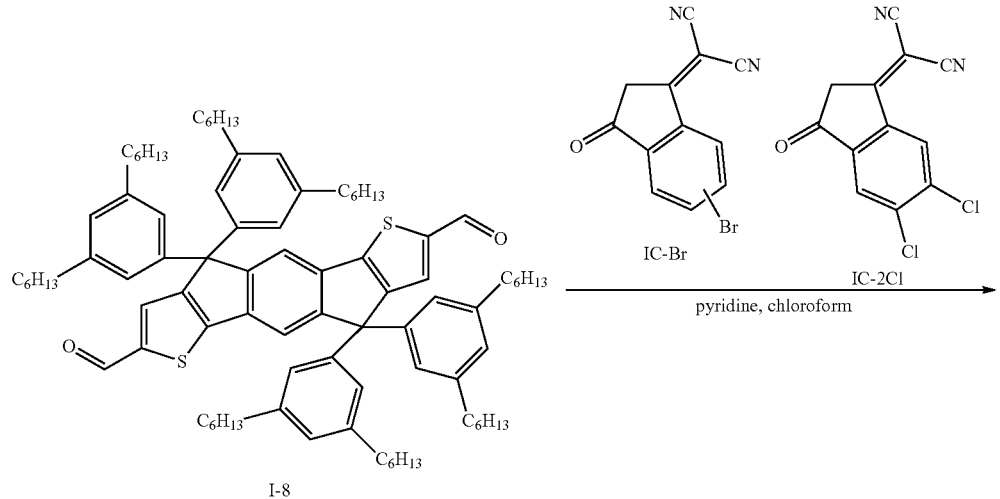

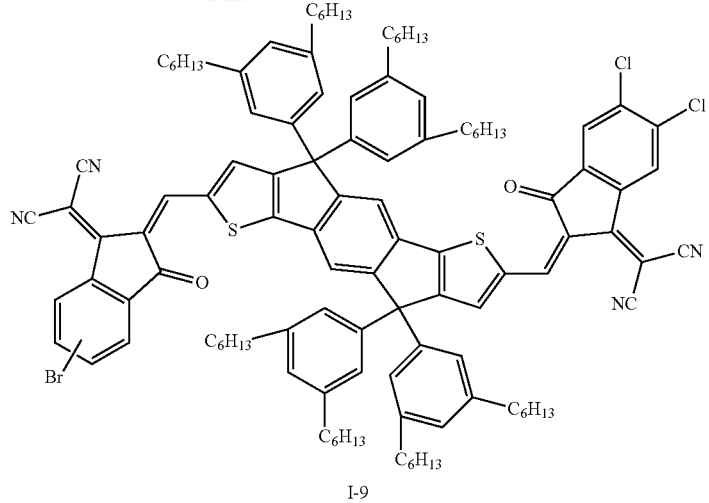

I-9

Put a 100 mL two-necked flask into an oven, bake at 100° C. for 30 min and degas chloroform 30 minutes for use later. Add 1.295 g (0.996 mmol) I-8, 0.543 g (1.992 mmol, 2 equiv.) IC-Br, 0.523 g (1.992 mmol, 2 equiv.) IC-2Cl, and degassed 40 mL chloroform into a 100 mL two-necked flask and then purge argon gas into the two-necked flask. Add 1.3 mL pyridine into the two-necked flask and immerse in a 60° C. oil bath to react for an hour. After completion of the reaction, precipitate product in 130 mL MeOH and filter to get solid. Wash the solid with acetone and ethyl acetate and purify with column chromatography toluene/heptane=⅔ as eluent. Collect product, remove the organic solvents by rotary evaporation, and vacuum dry for 16 hours to get 0.482 g dark red solid product with a yield rate of 26.9%. $^1$H NMR spectrum (600 MHz, CDCl$_3$) of the product I-9: δ 8.88 (s, 2H), 8.82 (s, 1H), 8.53-8.54 (m, 1H), 7.92 (s, 1H), 7.86 (d, 1H), 7.75-7.71 (m, 3H), 7.68-7.69 (m, 2H), 6.94 (s, 4H), 6.82 (s, 8H), 2.51 (t, 16H), 1.50-1.54 (m, 16H), 1.26-1.30 (m, 48H), 0.82-0.84 (m, 24H).

Compound 11 (dark red solid product) can also be obtained: 0.285 g, 16.0%. $^1$H NMR spectrum (600 MHz, CDCl$_3$) of the Compound 11: δ 8.88 (s, 2H), 8.77 (s, 2H), 7.92 (s, 2H), 7.70-7.73 (m, 4H), 6.94 (s, 4H), 6.82 (s, 8H), 2.49-2.55 (m, 16H), 1.50-1.55 (m, 16H), 1.22-1.32 (m, 48H), 0.82-0.85 (m, 24H).

Synthesis of Compound 1

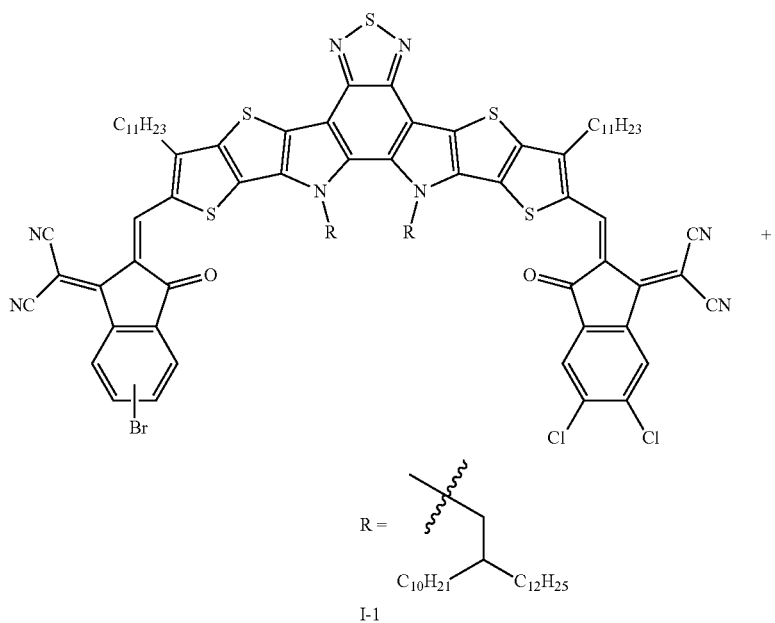

I-1

-continued

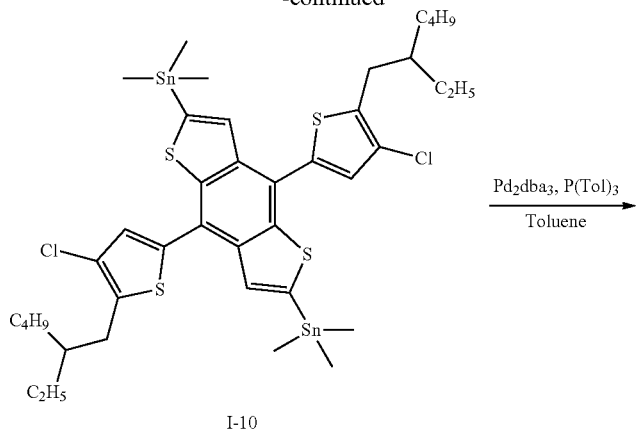

I-10

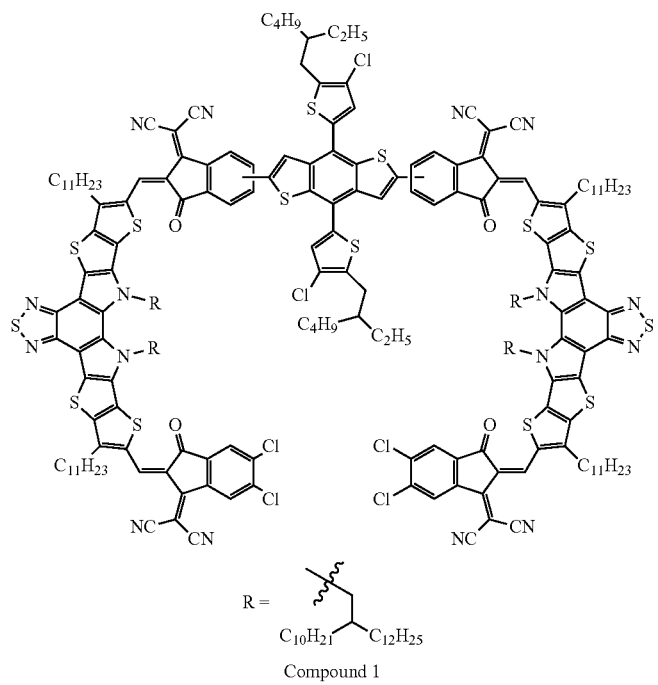

Compound 1

Add 0.198 g (0.100 mmol, 2.5 equiv.) I-1, 47.90 mg (0.040 mmol) I-10, 1.47 mg (0.0016 mmol, 0.04 equiv.) Pd$_2$dba$_3$, and 1.95 mg (0.0064 mmol, 0.16 equiv.) P(Tol)$_3$ into a 50 mL two-necked flask. Add 14.0 mL degassed toluene into the two-necked flask and immerse in a 115° C. oil bath to react for 18 hours. After completion of the reaction, precipitate product in 28 mL MeOH and filter to get solid. Purify with column chromatography with chloroform/heptane=½ as eluent. Collect product, remove the organic solvents by rotary evaporation, and vacuum dry for 16 hours to get 0.141 g bright bluish black solid product with a yield rate of 79.4%. $^1$H NMR spectrum (500 MHz, d$^4$-1,1,2,2-tetrachloroethane) of the compound 1: δ 9.17-9.22 (m, 6H), 8.78-8.83 (m, 2H), 7.98-8.25 (m, 8H), 7.39-7.45 (m, 2H), 4.82 (s, 8H), 3.29 (s, 8H), 2.96-3.03 (m, 4H), 2.12-2.15 (m, 4H), 0.87-1.98 (m, 298H).

Synthesis of Compound 2

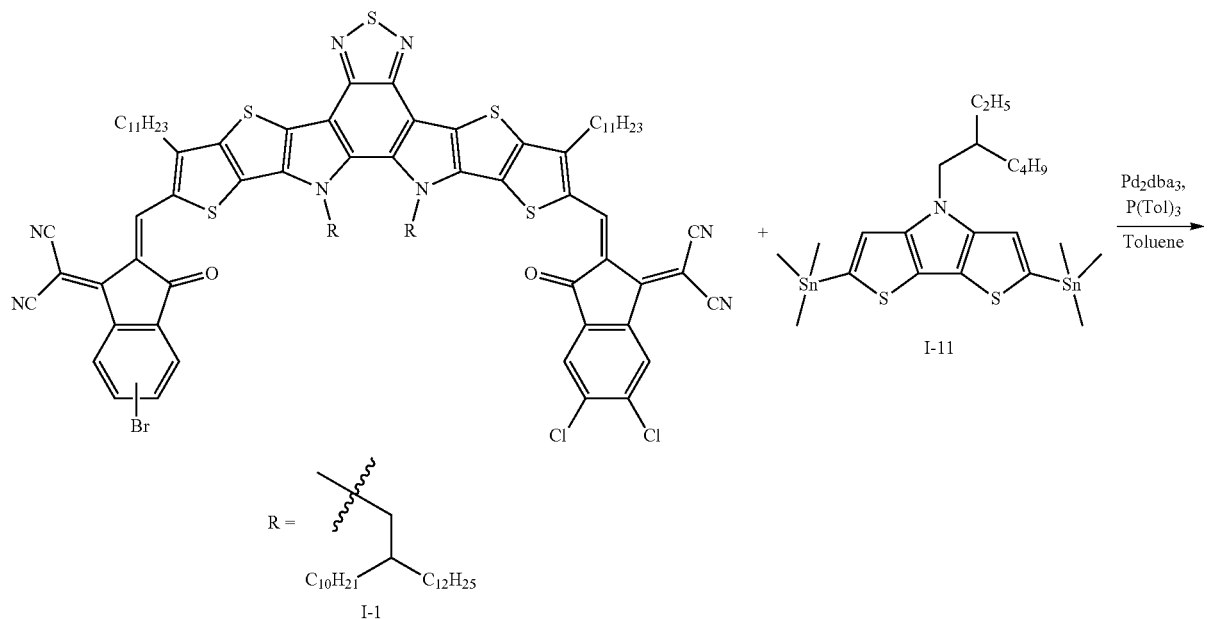

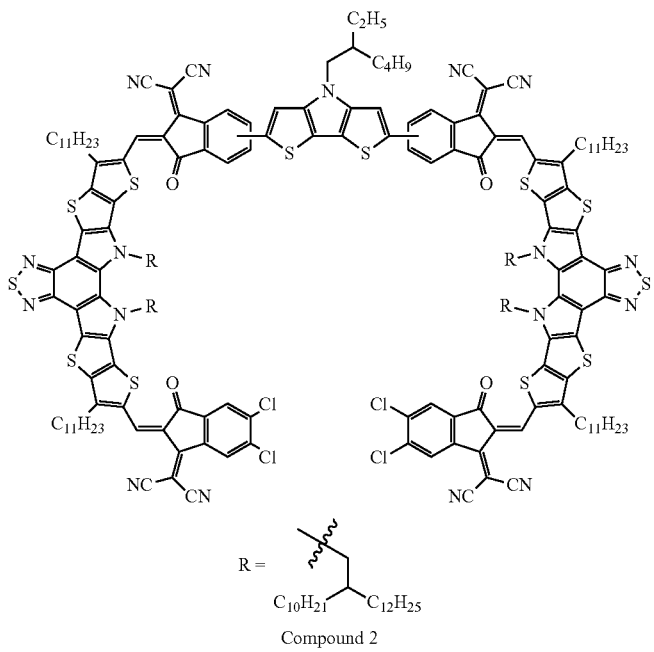

Compound 2

Weight and add 0.198 g (0.100 mmol, 2.5 equiv.) I-1, 24.70 mg (0.040 mmol) I-11, 1.47 mg (0.0016 mmol, 0.04 equiv.) $Pd_2dba_3$, and 1.95 mg (0.0064 mmol, 0.16 equiv.) $P(Tol)_3$ into a 50 mL two-necked flask. Add 14.0 mL degassed toluene into the two-necked flask and immerse in a 115° C. oil bath to react for 18 hours. After completion of the reaction, precipitate product in 28 mL MeOH and filter to get solid. Purify with column chromatography with chloroform/heptane=1/1 as eluent. Collect product, remove the organic solvents by rotary evaporation, and vacuum dry for 16 hours to get 0.127 g bright bluish black solid product with a yield rate of 77.9%. $^1H$ NMR spectrum (500 MHz, $d^4$-1,1,2,2-tetrachloroethane) of the compound 2: δ 9.12-9.20 (m, 4H), 9.00-9.03 (m, 2H), 8.82 (s, 2H), 7.95-8.01 (m, 6H), 7.47-7.51 (m, 2H), 4.79-4.84 (m, 8H), 4.20-4.23 (m, 2H), 3.26-3.29 (m, 8H), 2.15-2.18 (m, 5H), 1.97 (s, 8H), 0.87-1.46 (m, 274H).

Synthesis of Compound 3
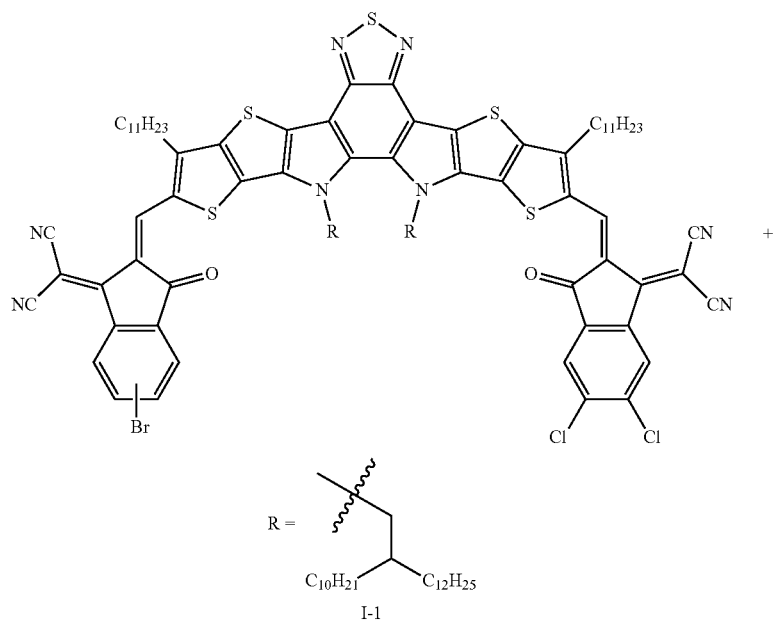
I-1
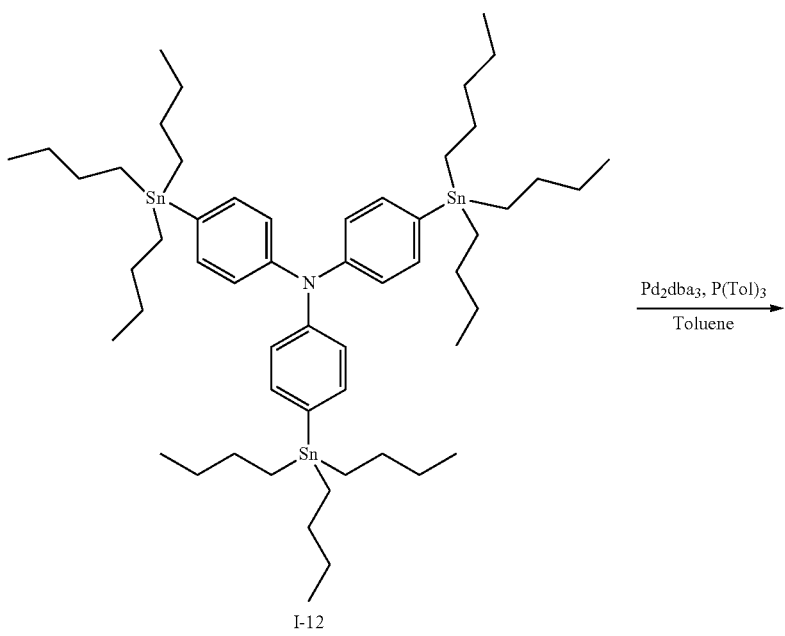
I-12

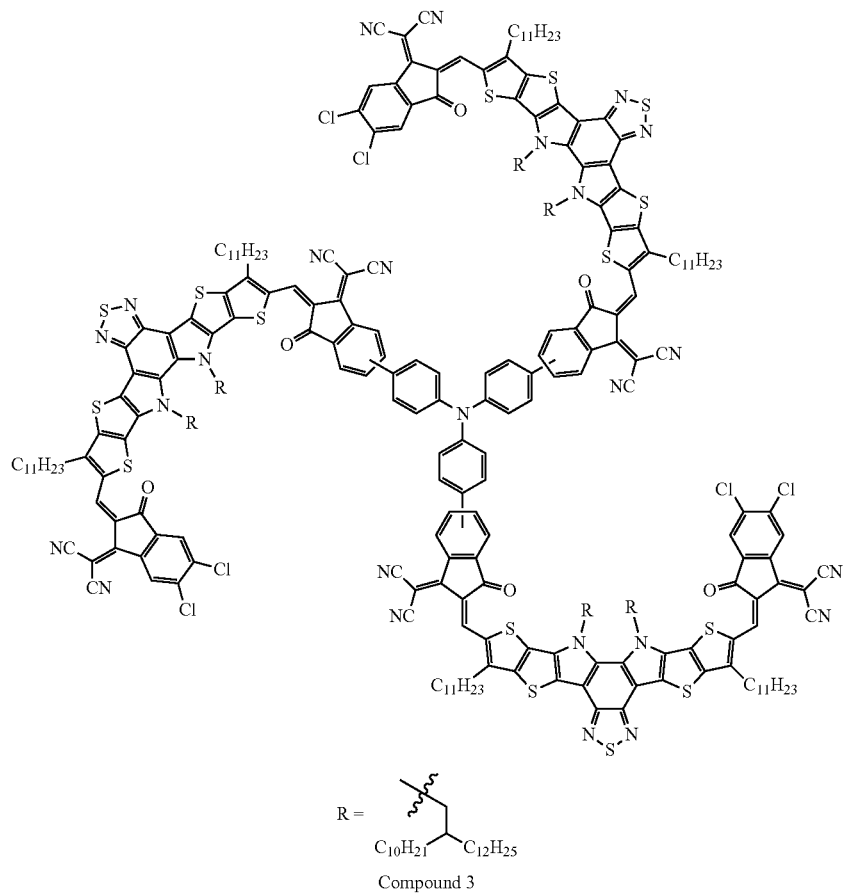

Compound 3

Weight and add 0.198 g (0.100 mmol, 2.5 equiv.) I-1, 37.00 mg (0.033 mmol) 1-12, 1.23 mg (0.0013 mmol, 0.04 equiv.) $Pd_2dba_3$, and 1.627 mg (0.0053 mmol, 0.16 equiv.) $P(Tol)_3$ into a 50 mL two-necked flask. Add 16.0 mL degassed toluene into the two-necked flask and immerse in a 115° C. oil bath to react for 18 hours. After completion of the reaction, precipitate product in 32 mL MeOH and filter to get solid. Purify with column chromatography with chloroform/heptane=3/2 as eluent. Collect product, remove the organic solvents by rotary evaporation, and vacuum dry for 16 hours to get 0.053 g bright bluish black solid product with a yield rate of 26.7%. $^1H$ NMR spectrum (500 MHz, $d^4$-1,1,2,2-tetrachloroethane) of the compound 3: δ 9.20-9.23 (m, 6H), 8.78-8.82 (m, 6H), 7.99-8.04 (m, 9H), 7.69-7.78 (m, 6H), 7.27-7.41 (m, 6H), 4.82 (s, 12H), 2.16 (s, 6H), 1.95-1.98 (m, 12H), 0.87-1.47 (m, 402H).

Synthesis of Compound 4

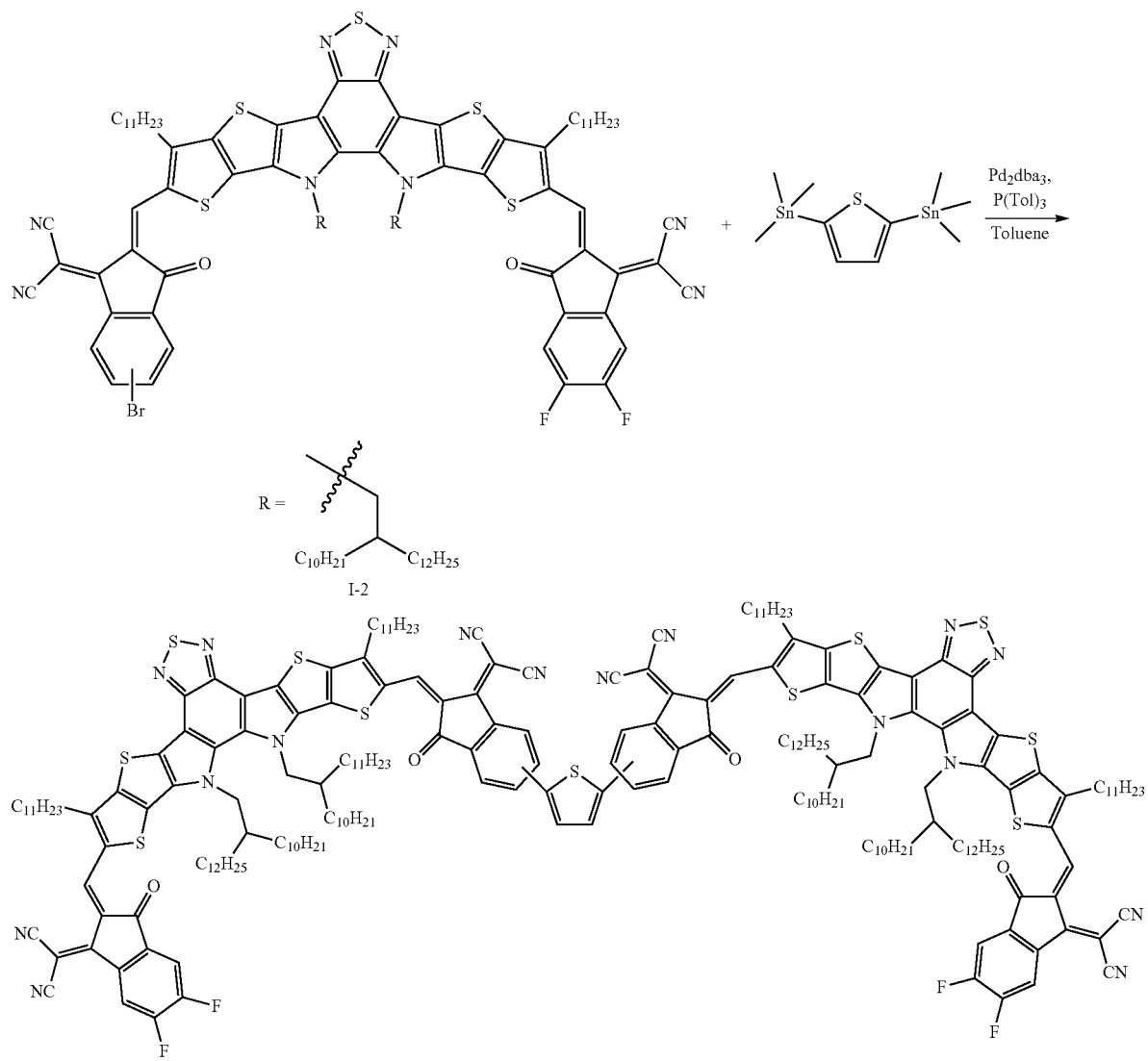

Compound 4

Weight and add 0.1944 g (0.10 mmol, 2.5 equiv.) I-2, 16.4 mg (0.04 mmol) 2,5-bis(trimethylstannyl)thiophene, 1.47 mg (0.0016 mmol, 0.04 equiv.) $Pd_2dba_3$, and 1.95 mg (0.0064 mmol, 0.16 equiv.) $P(Tol)_3$ into a 50 mL three-necked flask. Add 14.0 mL degassed toluene into the two-necked flask and immerse in a 115° C. oil bath to react for 18 hours. After completion of the reaction, precipitate product in 28.0 mL MeOH and filter to get solid. Purify with column chromatography with chloroform/heptane=2/1 as eluent. Collect product, remove the organic solvents by rotary evaporation, and vacuum dry for 16 hours to get 0.062 g bright bluish black solid product with a yield rate of 40.7%.

$^1$H NMR spectrum (500 MHz, $d^4$-1,1,2,2-tetrachloroethane) of the compound 4: δ 9.22 (s, 4H), 9.08 (s, 2H), 8.57-8.60 (m, 2H), 7.99-8.08 (m, 4H), 7.71-7.74 (m, 2H), 7.66=7.67 (m, 2H), 4.81-4.85 (m, 8H), 3.30-3.32 (m, 8H), 2.15-2.17 (m, 4H), 1.95-2.00 (m, 8H), 0.88-1.63 (m, 268H).

Synthesis of Compound 5

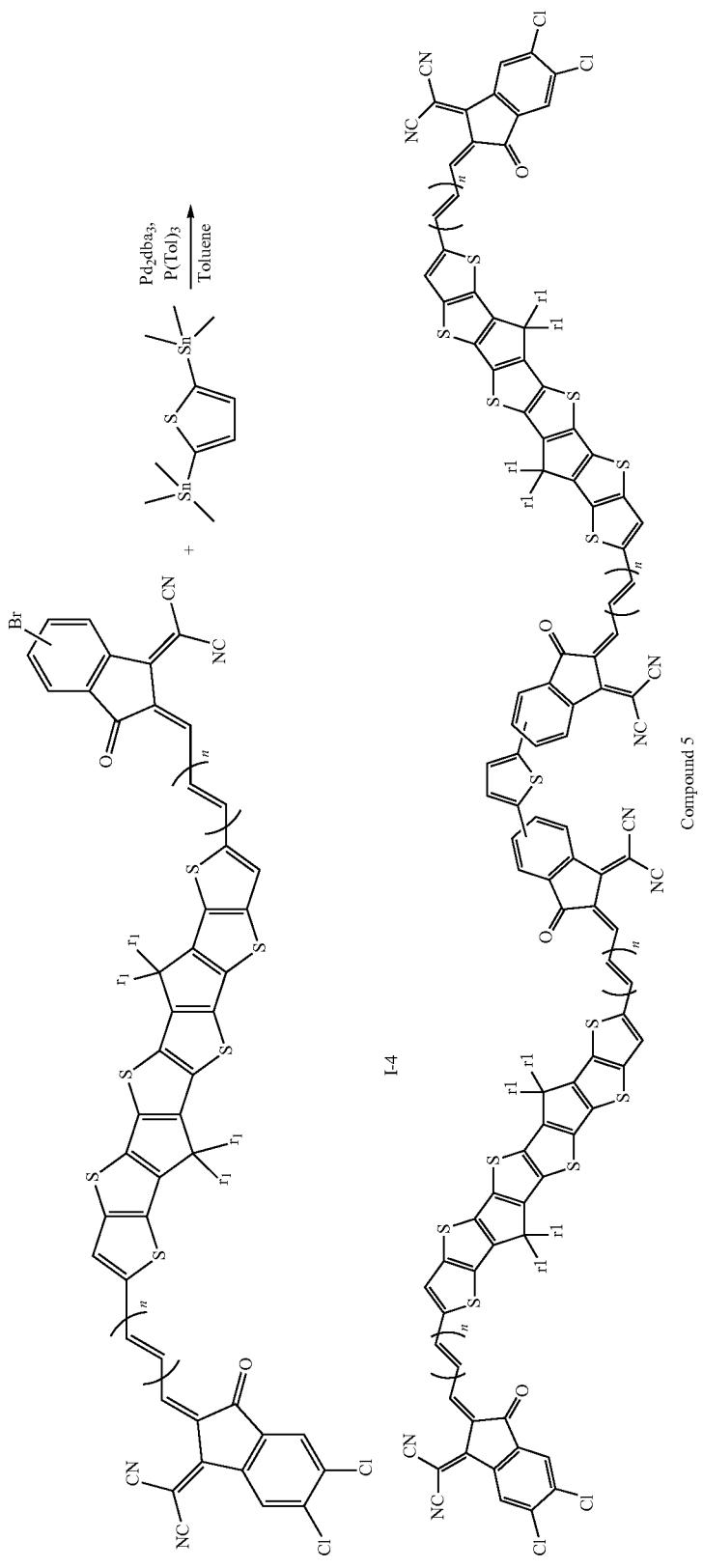

Weight and add 0.182 g (0.09 mmol, 3.0 equiv) I-4, 12.3 mg (0.030 mmol) 2,5-bis(trimethylstannyl)thiophene, 1.10 mg (0.0012 mmol, 0.04 equiv.) Pd$_2$dba$_3$, and 1.46 mg (0.0048 mmol, 0.16 equiv.) P(Tol)$_3$ into a 50 mL two-necked flask. Add 12.8 mL degassed toluene into the two-necked flask and immerse in a 115° C. oil bath to react for 18 hours. After completion of the reaction, precipitate product in 25.6 mL MeOH and filter to get solid. Purify with column chromatography with chloroform/heptane=4/1 as eluent. Collect product, remove the organic solvents by rotary evaporation, and vacuum dry for 16 hours to get 0.085 g black solid product with a yield rate of 71.2%. $^1$H NMR spectrum (500 MHz, d$^4$-1,1,2,2-tetrachloroethane) of the compound 5: δ 9.00 (s, 2H), 8.74 (s, 4H), 8.11 (s, 4H), 7.97-8.00 (m, 6H), 7.91-7.93 (m, 8H), 7.61 (s, 4H), 6.95 (s, 8H), 6.85 (s, 16H), 2.56 (t, 32H), 1.57-1.60 (m, 32H), 1.47 (s, 32H), 1.27-1.31 (m, 64H), 0.83-0.88 (m, 48H).

Synthesis of Compound 6

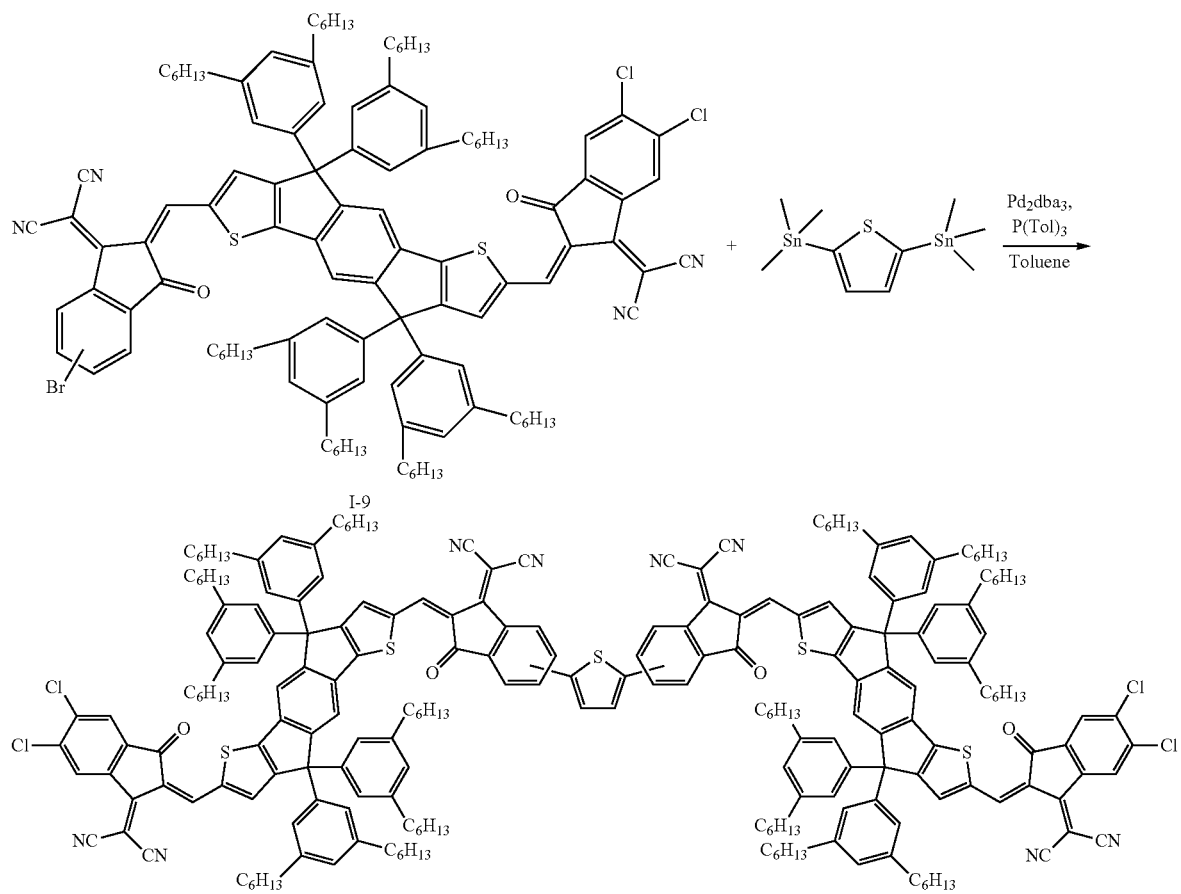

Compound 6

Weight and add 0.180 g (0.10 mmol, 2.5 equiv.) I-9, 16.4 mg (0.040 mmol) 2,5-bis(trimethylstannyl)thiophene, 1.47 mg (0.0016 mmol, 0.04 equiv.) Pd$_2$dba$_3$, and 1.95 mg (0.0064 mmol, 0.16 equiv.) P(Tol)$_3$ into a 50 mL two-necked flask. Add 12.6 mL degassed toluene into the two-necked flask and immerse in a 115° C. oil bath to react for 18 hours. After completion of the reaction, precipitate product in 25.2 mL MeOH and filter to get solid. Purify with column chromatography with chloroform/heptane=1/1 as eluent. Collect product, remove the organic solvents by rotary evaporation, and vacuum dry for 16 hours to get 0.090 g dark red solid product with a yield rate of 63.8%. $^1$H NMR spectrum (500 MHz, d$^4$-1,1,2,2-tetrachloroethane) of the compound 6: δ 9.01 (s, 2H), 8.87 (s, 4H), 8.77 (s, 2H), 7.98-8.04 (m, 2H), 7.95 (s, 4H), 7.82-7.85 (m, 4H), 7.74 (s, 4H), 7.61 (s, 2H), 6.95 (s, 8H), 6.87 (s, 16H), 2.56 (t, 32H), 1.58-1.65 (m, 32H), 1.46 (s, 32H), 1.23-1.30 (m, 64H), 0.80-0.83 (m, 48H).

Synthesis of Compound 7

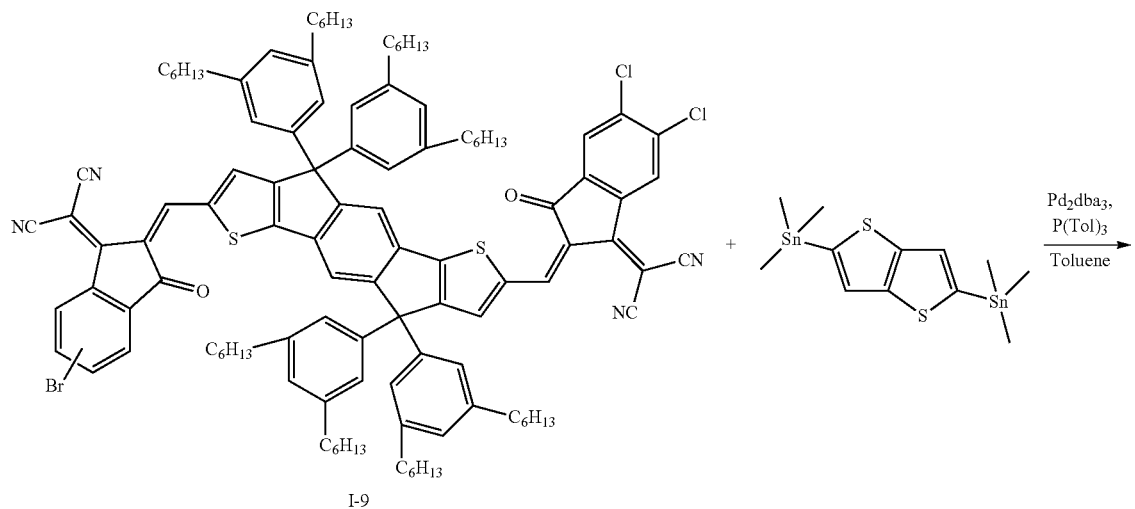

I-9

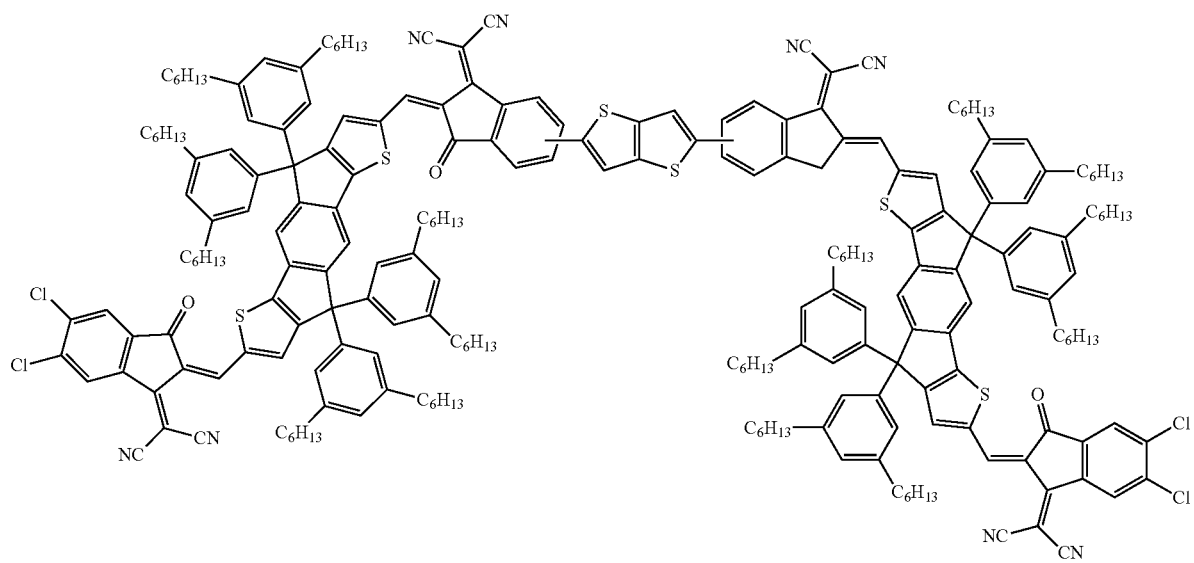

Compound 7

Weight and add 0.180 g (0.10 mmol, 2.5 equiv.) I-9, 18.6 mg (0.040 mmol) 2,5-bis(trimethylstannyl)thiophene, 1.47 mg (0.0016 mmol, 0.04 equiv.) $Pd_2dba_3$, and 1.95 mg (0.0064 mmol, 0.16 equiv.) $P(Tol)_3$ into a 50 mL two-necked flask. Add 12.6 mL degassed toluene into the reaction and immerse in a 115° C. oil bath to react for 18 hours. After completion of the reaction, precipitate product in 25.2 mL MeOH and filter to get solid. Purify with column chromatography with chloroform/heptane=1/1 as eluent. Collect product, remove the organic solvents by rotary evaporation, and vacuum dry for 16 hours to get 0.114 g dark red solid product with a yield rate of 79.7%. $^1$H NMR spectrum (500 MHz, $d^4$-1,1,2,2-tetrachloroethane) of the compound 7: δ 9.01 (s, 2H), 8.87 (s, 4H), 8.77 (s, 2H), 7.94-8.00 (m, 4H), 7.82-7.85 (m, 4H), 7.73-7.78 (m, 8H), 6.95 (s, 8H), 6.84-6.87 (m, 16H), 2.56 (t, 32H), 1.56-1.62 (m, 32H), 1.31-1.37 (m, 96H), 0.84-0.99 (m, 48H).

Synthesis of Compound 8

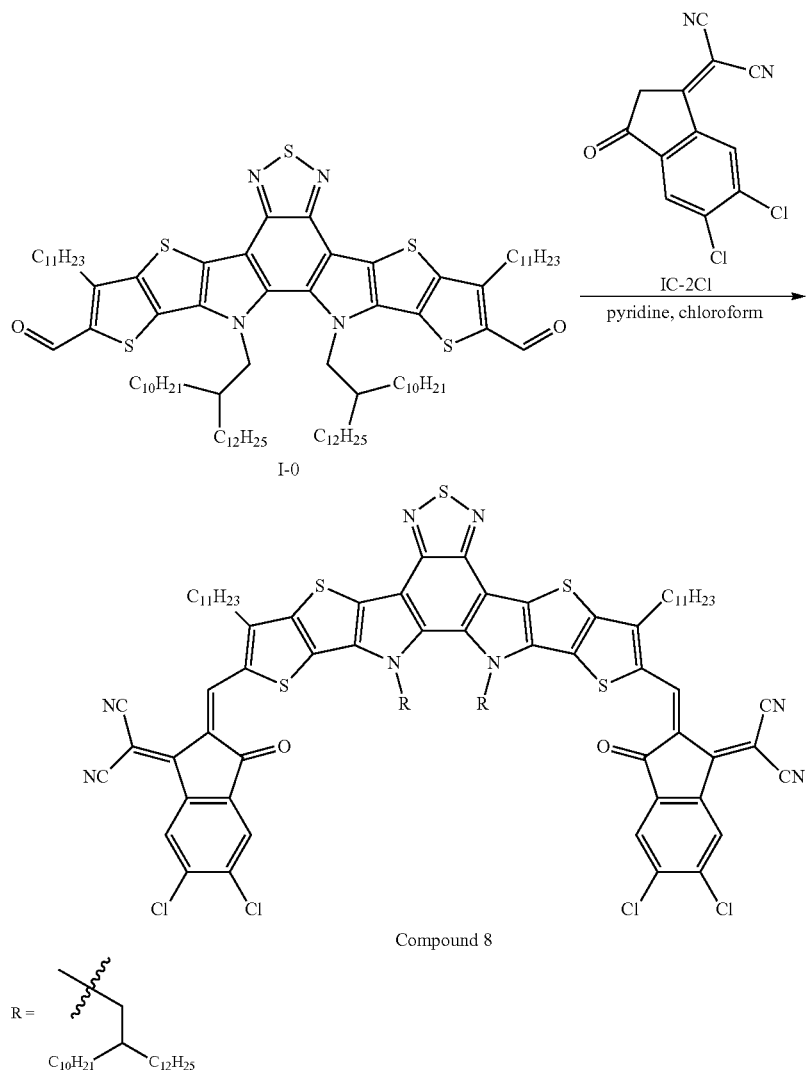

Compound 8

Put a 100 mL two-necked flask into an oven, bake at 100° C. for 30 min and degas chloroform 30 min for later use. Weight and add 0.300 g (0.203 mmol) I-0, 0.267 g (1.016 mmol, 5 equiv.) IC-2Cl, and degassed 9.0 mL chloroform into a 100 mL two-necked flask and then purge argon gas into the two-necked flask. Add 0.3 mL pyridine into the two-necked flask and immerse in a 60° C. oil bath to react for an hour. After completion of the reaction, precipitate product in 30 mL MeOH and filter to get solid. Wash the solid with acetone and ethyl acetate and purify with column chromatography with toluene/heptane=3/1 as eluent. Collect product, remove the organic solvents by rotary evaporation, and vacuum dry for 16 hours to get 0.392 g bright bluish black solid product with a yield rate of 98.2%. $^1$H NMR spectrum (600 MHz, CDCl$_3$) of the compound 8: δ 9.19 (s, 2H), 8.81 (s, 2H), 7.96 (s, 2H), 4.75-4.76 (m, 4H), 3.24 (t, 4H), 2.09-2.11 (m, 2H), 1.88 (s, 4H), 0.81-1.26 (m, 172H).

The n-type organic semiconductor compounds used in the present invention are shown in table 1.

TABLE 1
n-type organic semiconductor compounds
compound1
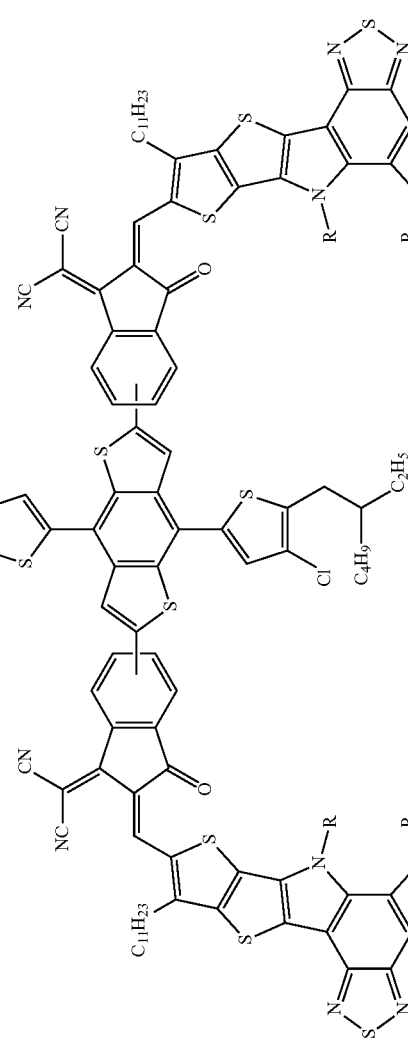
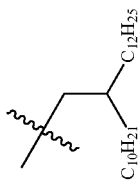

TABLE 1-continued
n-type organic semiconductor compounds
compound 2
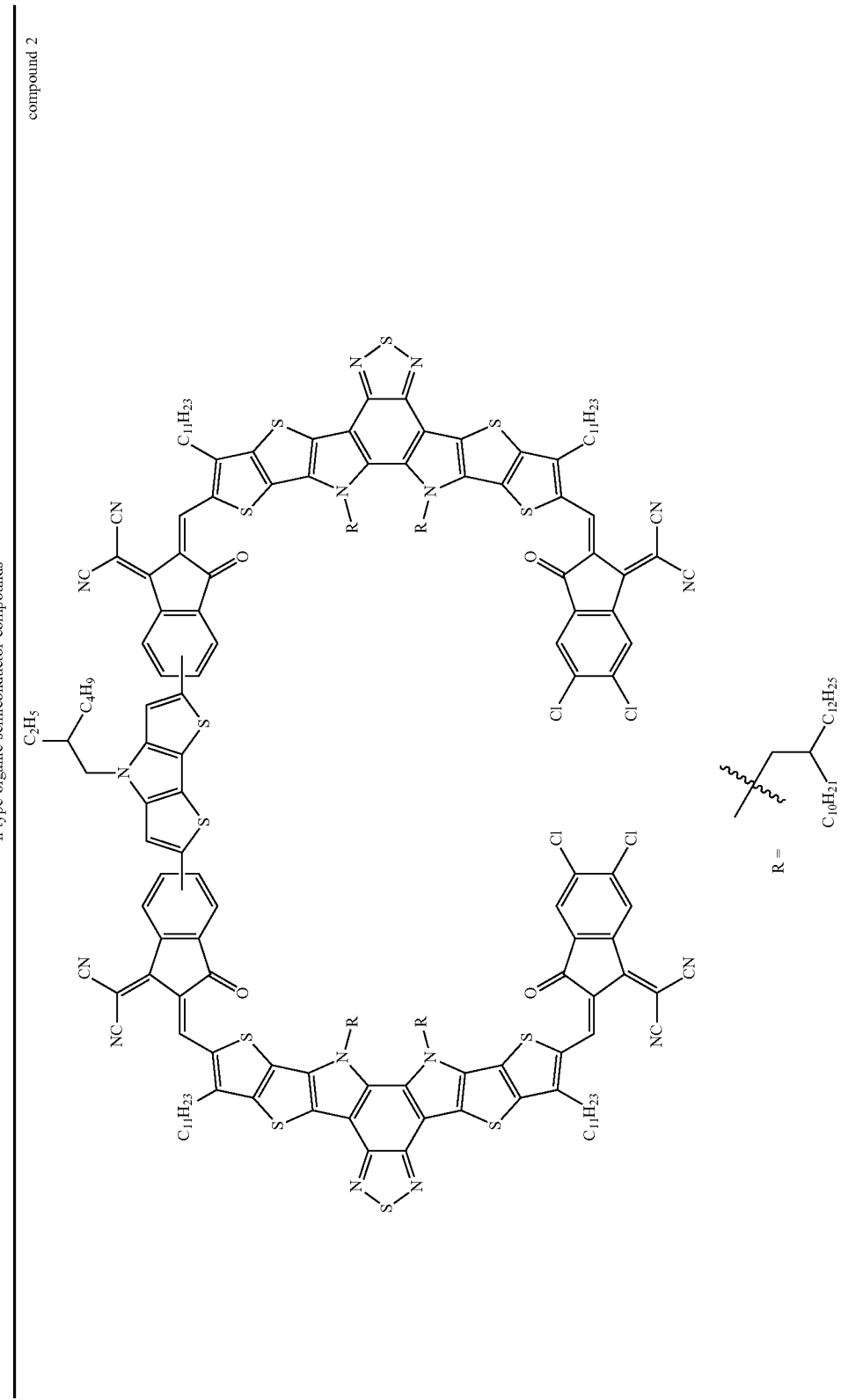

TABLE 1-continued
n-type organic semiconductor compounds
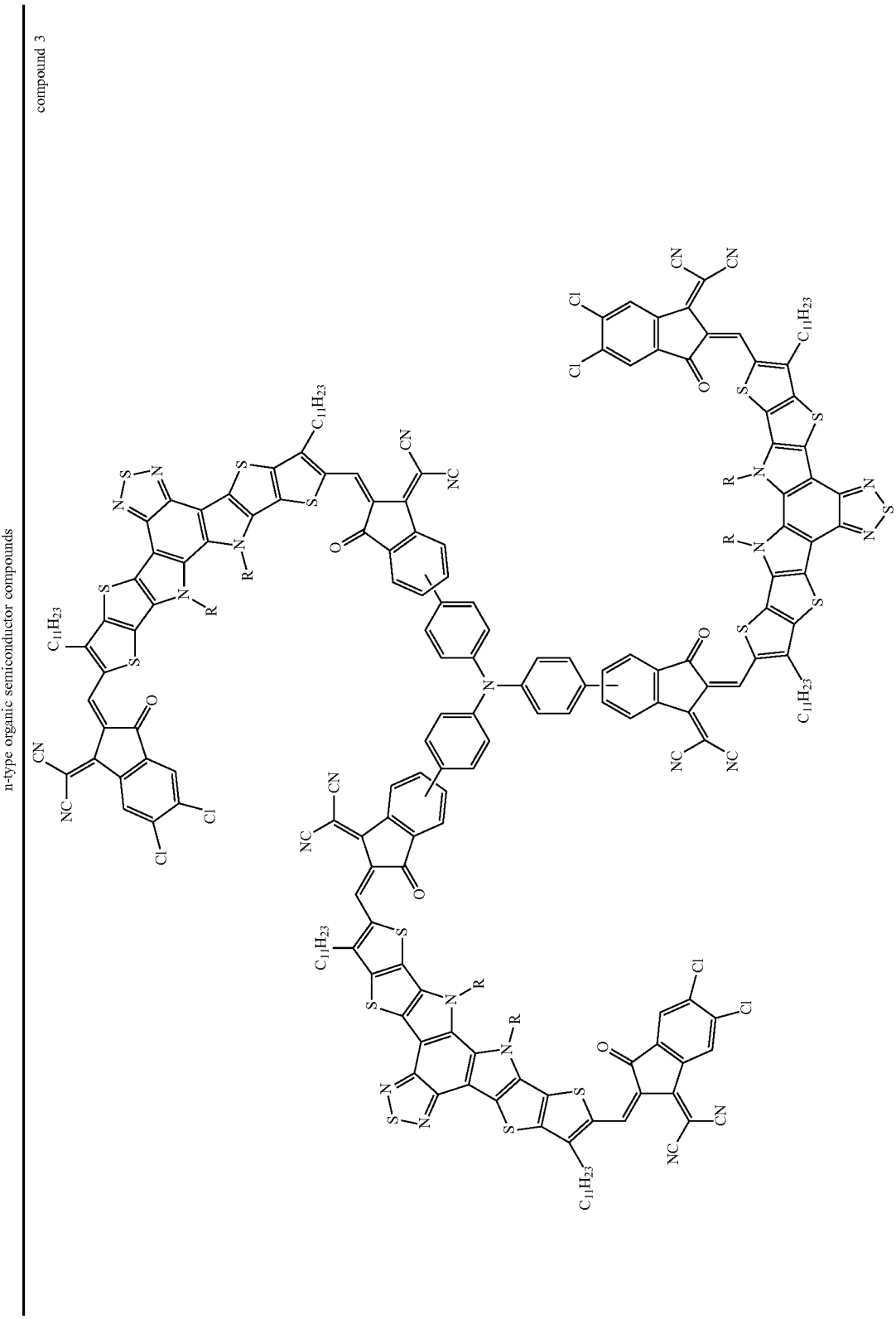
compound 3

TABLE 1-continued
n-type organic semiconductor compounds
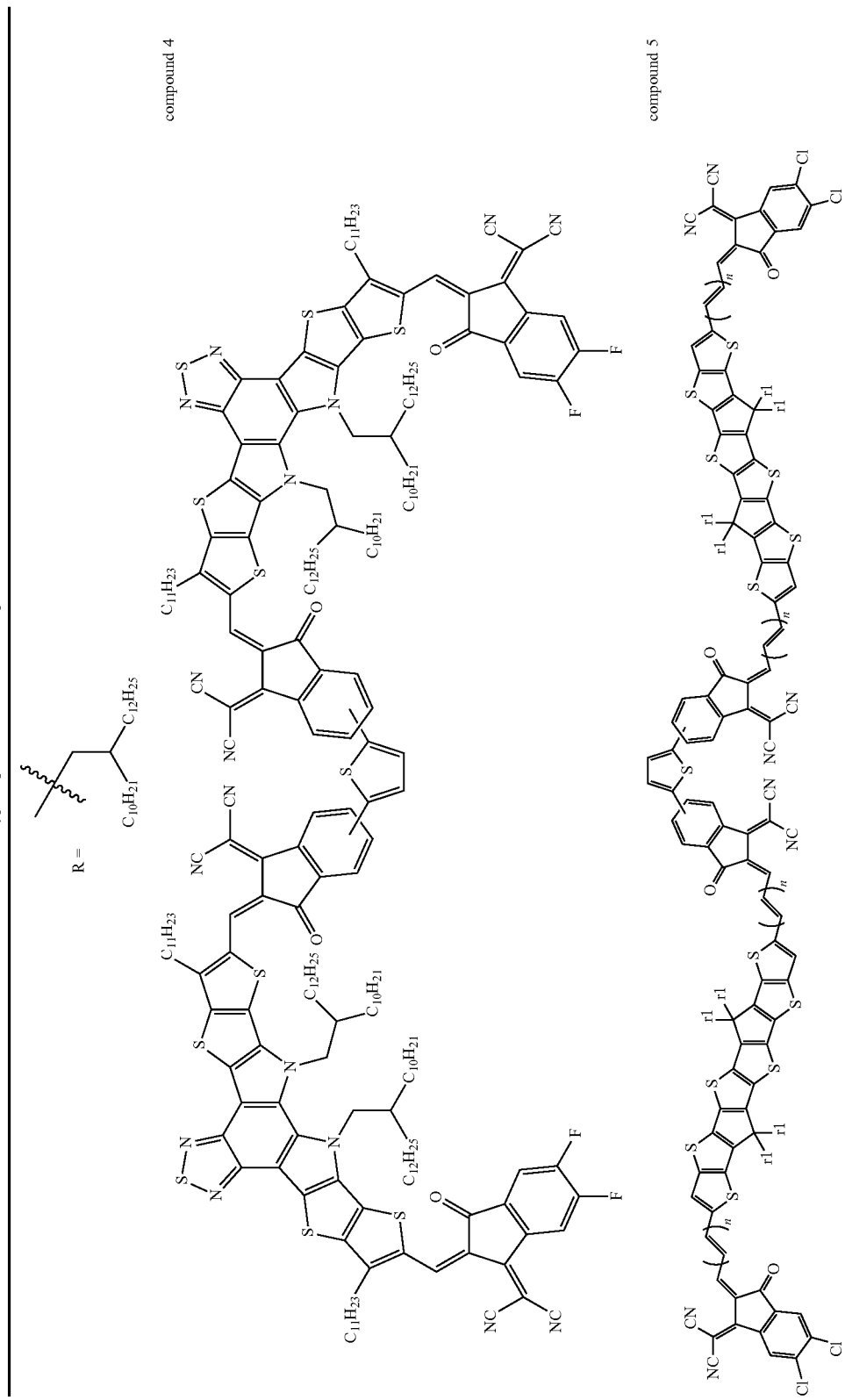
compound 4
compound 5

TABLE 1-continued
n-type organic semiconductor compounds
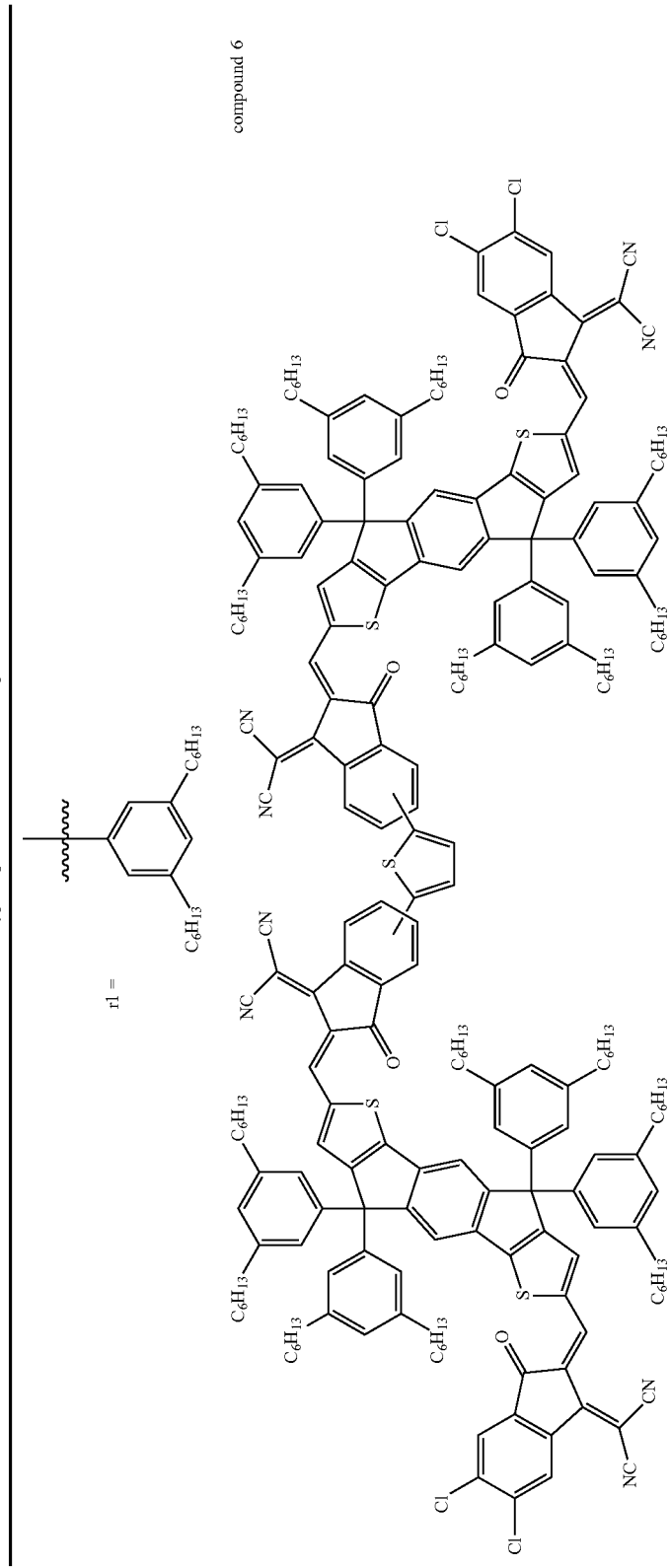
compound 6

TABLE 1-continued
n-type organic semiconductor compounds
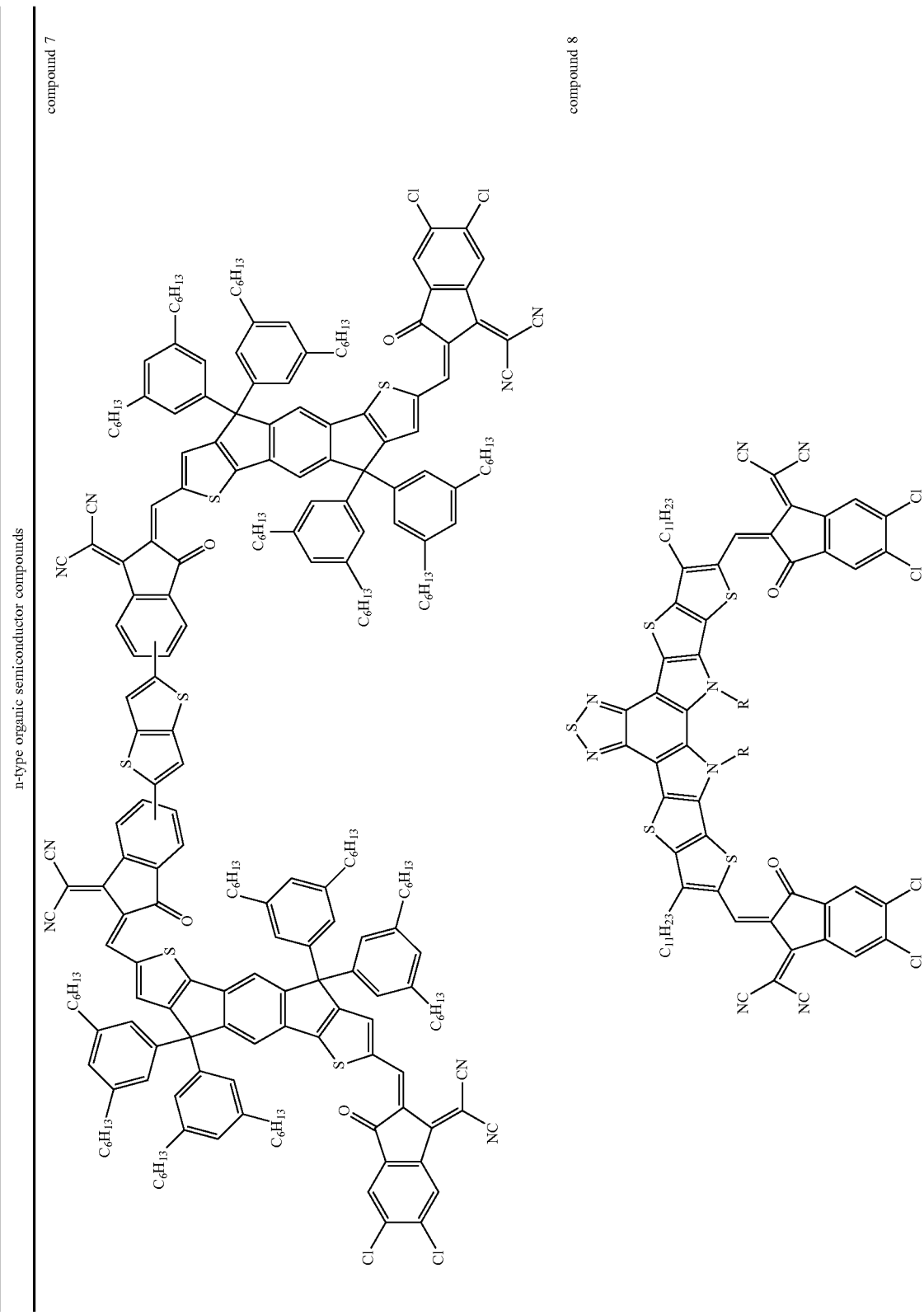
compound 7
compound 8

TABLE 1-continued
n-type organic semiconductor compounds
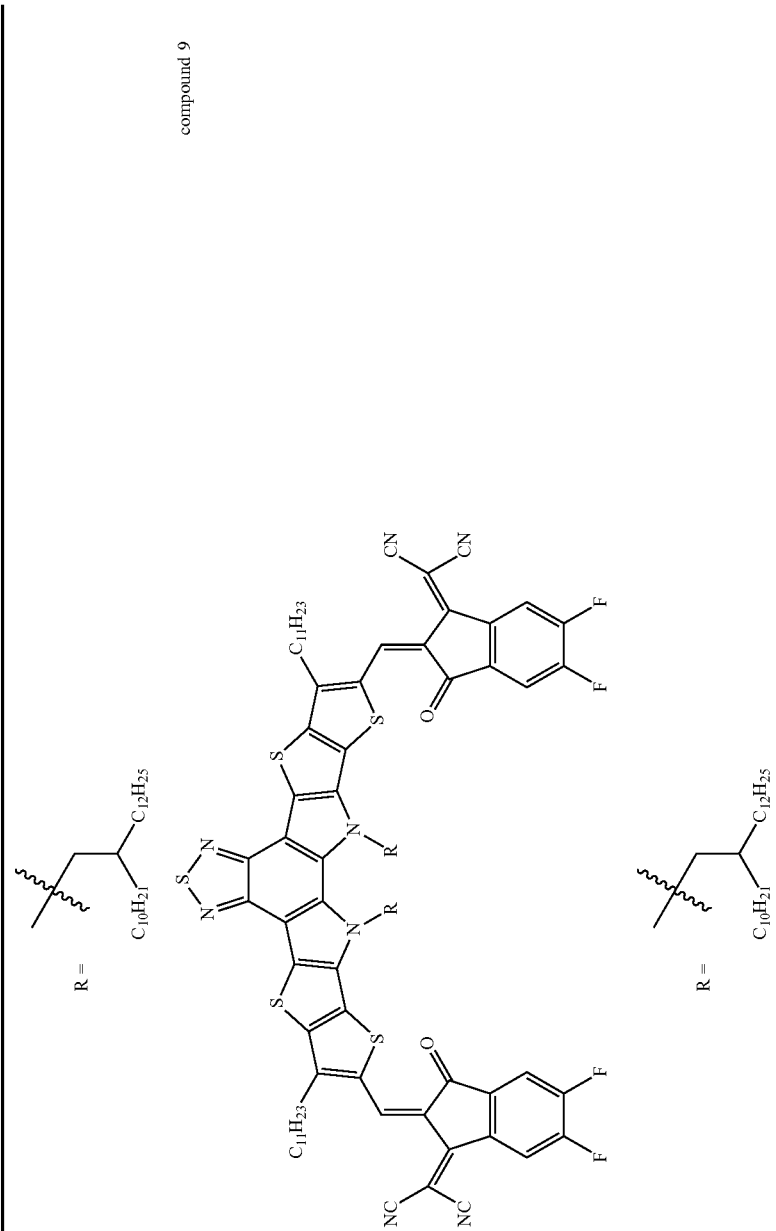
compound 9

TABLE 1-continued
n-type organic semiconductor compounds
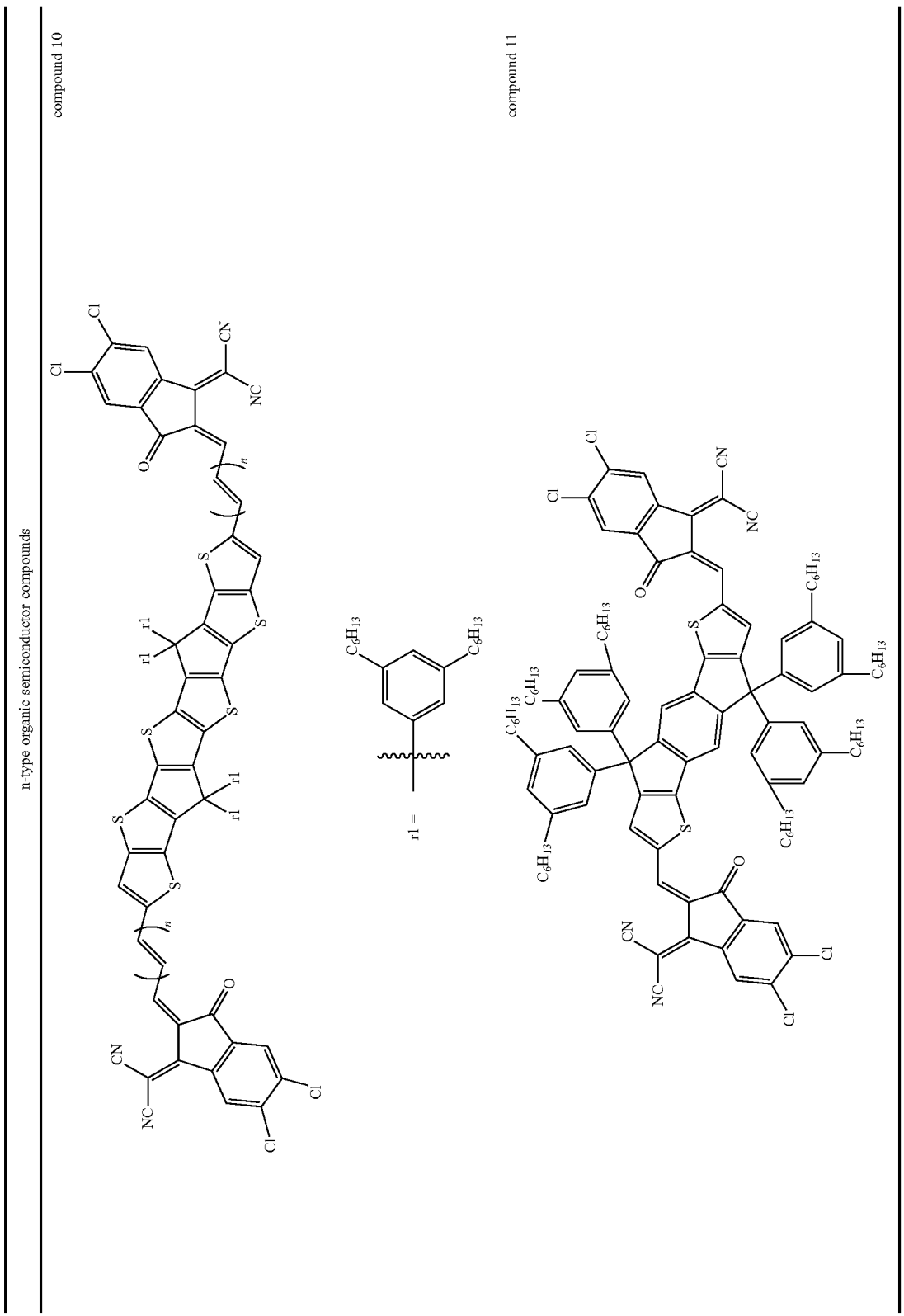
compound 10
compound 11

The p-type organic semiconductor compounds used in the present invention are shown in table 2.
TABLE 2
p-type organic semiconductor compounds
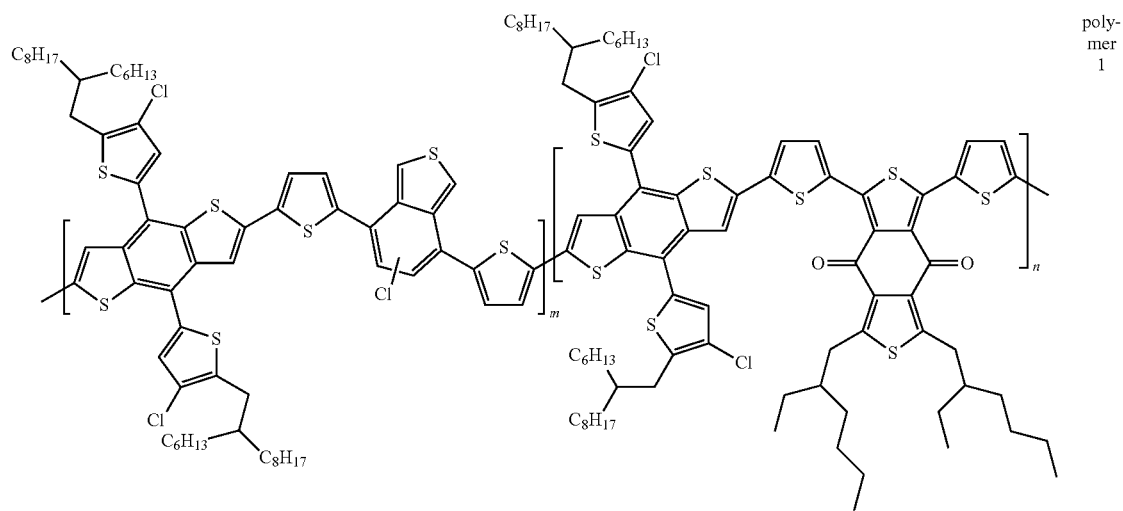
polymer 1
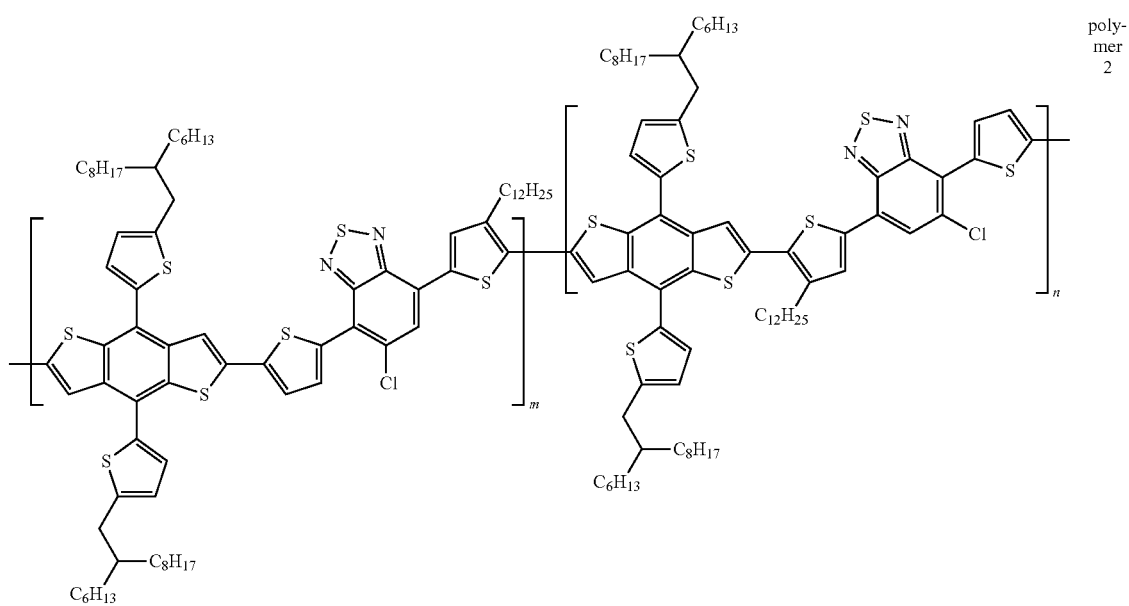
polymer 2

TABLE 2-continued p-type organic semiconductor compounds

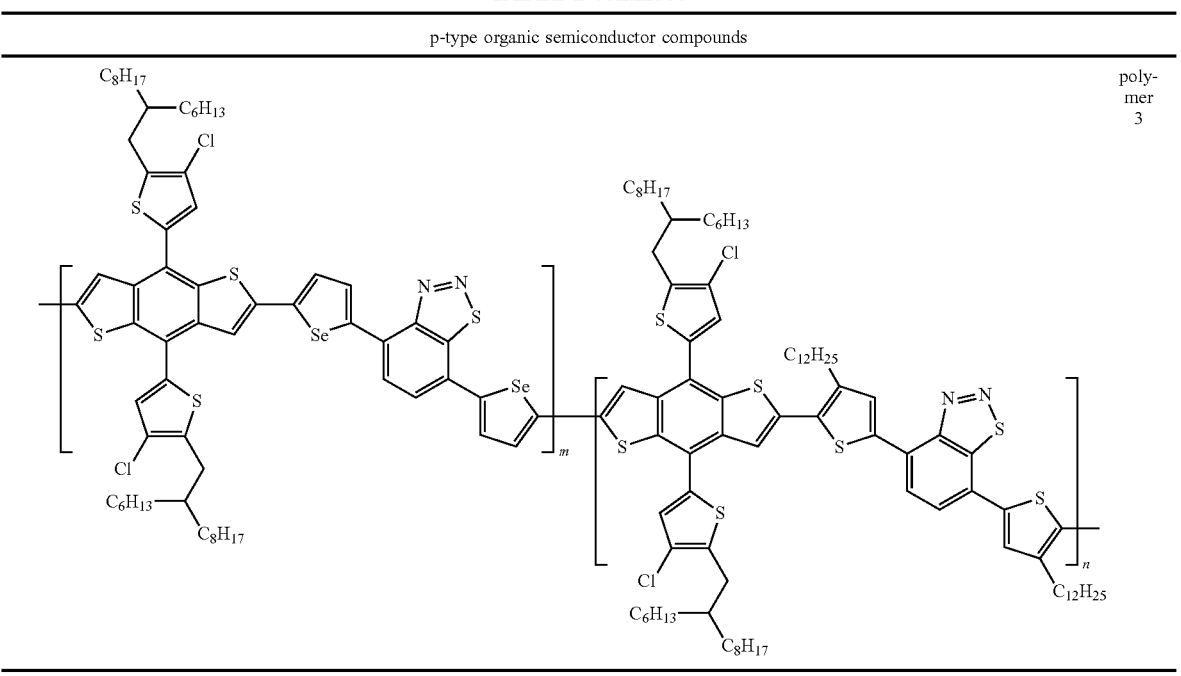

polymer 3

Figure 1A:
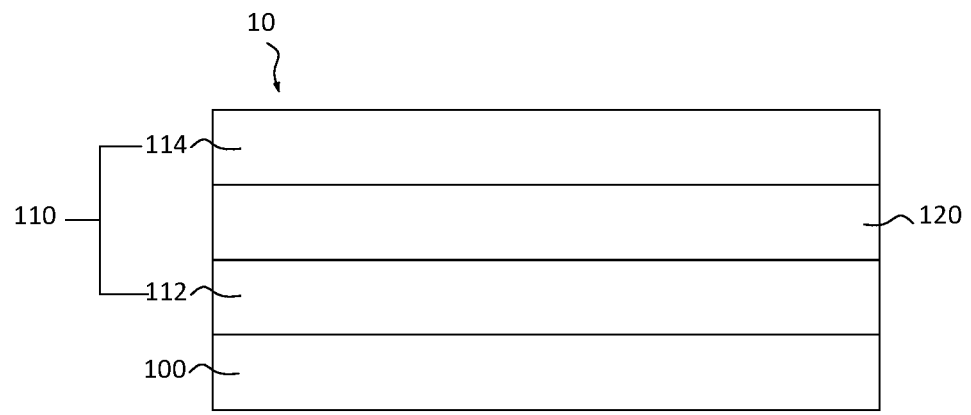
FIG. 1A-1F are schematic drawings showing structure of an embodiment of an organic optoelectronic device according to the present invention.

Refer to FIG. 1A, an organic optoelectronic device 10 according to the present invention includes a substrate 100, an electrode module 110, and an active layer 120. The electrode module 110 which consists of a first electrode 112 and a second electrode 114 is disposed over the substrate 100 while the active layer 120 is arranged between the first electrode 112 and the second electrode 114. The first electrode 112 is disposed between the substrate 100 and the active layer 120 while the second electrode 114 is located above the active layer 120.

In this embodiment, the active layer 120 includes the present organic semiconductor mixture. At least one of the two electrodes, the first electrode 112 and the second electrode 114, is transparent or semi-transparent.

In order to process the organic semiconductor mixture of the present invention, firstly at least one small molecule compound and/or polymer with at least one of the following features including charge transfer, semiconductivity, electrical conductivity, photoconductivity, hole blocking, and electron blocking is added and blended for preparation of a first component.

Moreover, the present organic semiconductor mixture can be mixed with at least one of the following organic solvents including aliphatic hydrocarbons, chlorinated hydrocarbon, aromatic hydrocarbons, ketones, ethers, and combinations thereof such as toluene, o-xylene, p-xylene, 1,3,5- or 1,2,4-trimethylbenzene, tetrahydrofuran, and 2-methyltetrahydrofuran for preparing a second component.

The organic semiconductor mixture can be used in a patterned organic semiconductor layer in the device described above. As to modern microcomputer applications, patterning of the thin organic semiconductor layer for production of small structure or patterns with lower cost (more devices per unit area) and power consumption can be achieved by photolithography, electron-beam lithography, or laser patterning.

In order to form thin layers in electronics or optoelectronic devices, the organic semiconductor mixture of the present invention can be deposited by suitable ways. In the device, liquid coating is better than vacuum deposition. The organic semiconductor mixture of the present invention can make a plurality of liquid coating techniques become feasible.

Preferred deposition techniques include but not limited to dip coating, spin coating, ink-jet printing, nozzle-printing, relief printing, screen printing, gravure printing, blade coating, roller printing, reverse roll coating, planographic printing, dry offset printing, flexographic printing, web printing, spray coating, curtain coating, brush coating, slot-dye coating, and pad printing.

An organic optoelectronic device containing the present organic semiconductor mixture, the first component formed by the organic semiconductor mixture, or the second component formed by the organic semiconductor mixture is also provided. The organic optoelectronic device includes a substrate, an electrode module disposed on the substrate and provided with a first electrode and a second electrode, and an active layer arranged between the first electrode and the second electrode and made from material containing at least one present organic semiconductor mixture. At least one of the two electrodes, the first electrode and the second electrode, is transparent or semi-transparent.

Figure 1B:
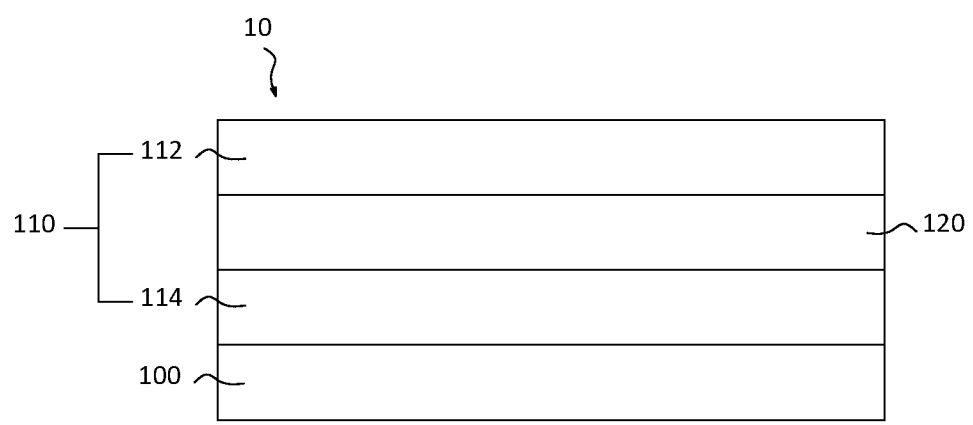

In another embodiment, refer to FIG. 1B, an organic optoelectronic device 10 includes a substrate 100, an electrode module 110, and an active layer 120. The electrode module 110 is disposed over the substrate 100 and provided with a first electrode 112 and a second electrode 114 while the active layer 120 is arranged between the first electrode 112 and the second electrode 114. The second electrode 114 is located between the substrate 100 and the active layer 120 while the first electrode 112 is located above the active layer 120.

The substrate 100 is preferred to be a glass substrate or a transparent soft substrate with mechanical strength, hot strength, and transparency. Materials for the transparent soft substrate include polyethylene, ethylene vinyl acetate copolymer, ethylene-vinyl alcohol copolymer, polypropylene, polystyrene, poly (methyl methacrylate), polyvinyl chloride, polyvinyl alcohol, polyvinyl butyral, nylon, polyetheretherketone, polysulfone, polyethersulfone, tetrafluoroethylene perfluoroalkyl vinyl ether copolymer, polyvinyl fluoride, ethylene-tetrafluoroethylene copolymer, tetrafluoroethylene-hexafluoropropylene copolymer, polychlorotrifluoroethylene, polyvinylidene difluoride, polyester, polycarbonate, polyurethane, polyimide, etc.

The first electrode 112 is made from metal oxides and their fluorine-doped derivatives such as transparent indium oxides, tin oxides, fluorine-doped tin oxide (FTO) or complex metal oxides including indium tin oxide (ITO), indium zinc oxide (IZO), etc.

The second electrode 114 can be made from metal oxides, metals (silver, aluminum, gold), conductive polymer, carbon-based conductors, metal compounds, or conductive films formed by combinations of the above materials.

In a preferred embodiment, the active layer 120 of the organic optoelectronic device 10 includes at least one n-type organic semiconductor compound such as the organic semiconductor compounds of the present invention mentioned above and at least one p-type organic semiconductor compound mentioned above.

In a preferred embodiment, the n-type organic semiconductor compound of the organic optoelectronic device 10 is preferred selected from the group consisting compound 1 to compound 11 shown in the above table one.

Figure 1C:
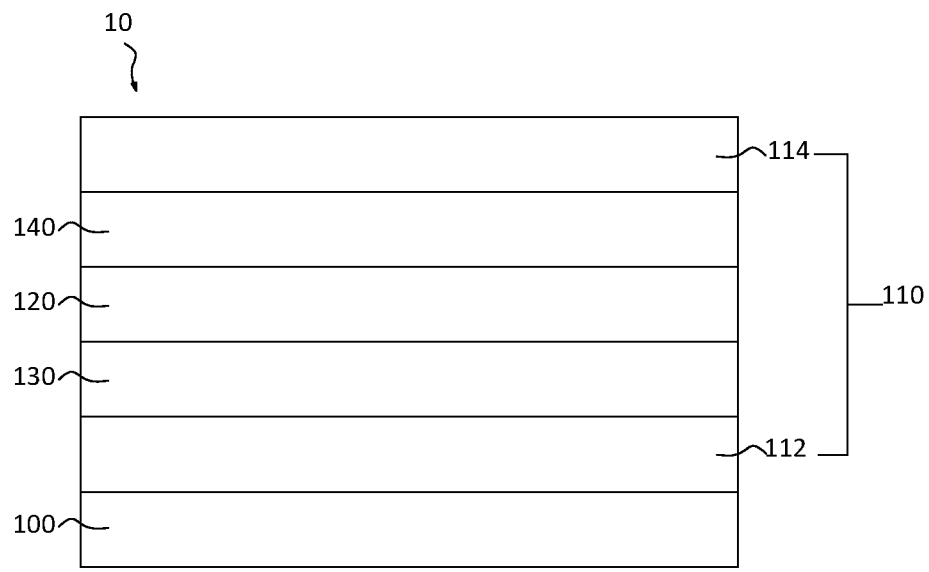

In a third embodiment shown in FIG. 1C, the respective components of the organic optoelectronic device 10 are arranged at the same order as the above first embodiment but the organic optoelectronic device 10 further includes a first carrier transport layer 130 disposed between the first electrode 112 and the active layer 120, and a second carrier transport layer 140 arranged between the second electrode 114 and the active layer 120.

Figure 1D:
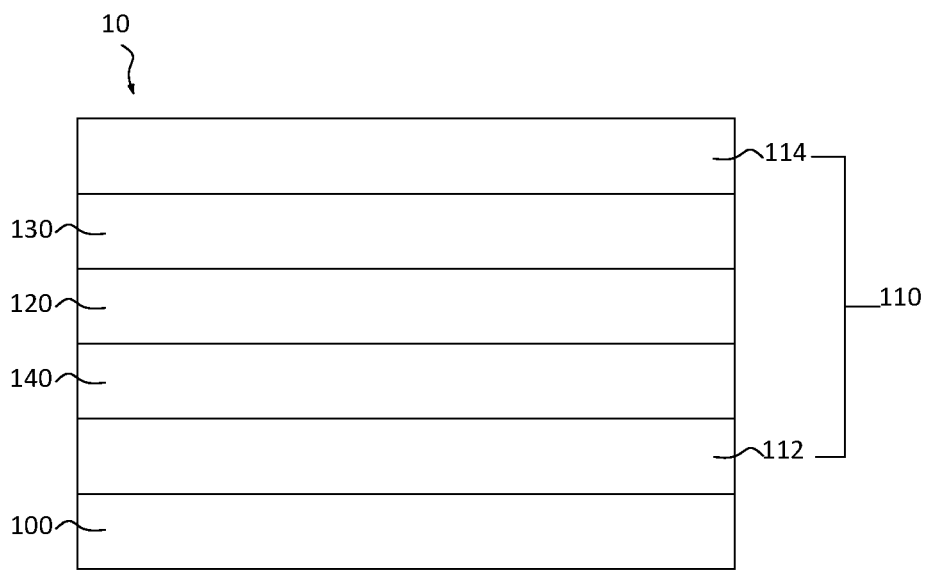

In a fourth embodiment, please refer to FIG. 1D. The respective components of the organic optoelectronic device 10 of this embodiment are arranged the same as those of the first embodiment. Yet the organic optoelectronic device 10 further includes a first carrier transporting layer 130 arranged between the second electrode 114 and the active layer 120, and a second carrier transporting layer 140 disposed between the first electrode 112 and the active layer 120.

Figure 1E:
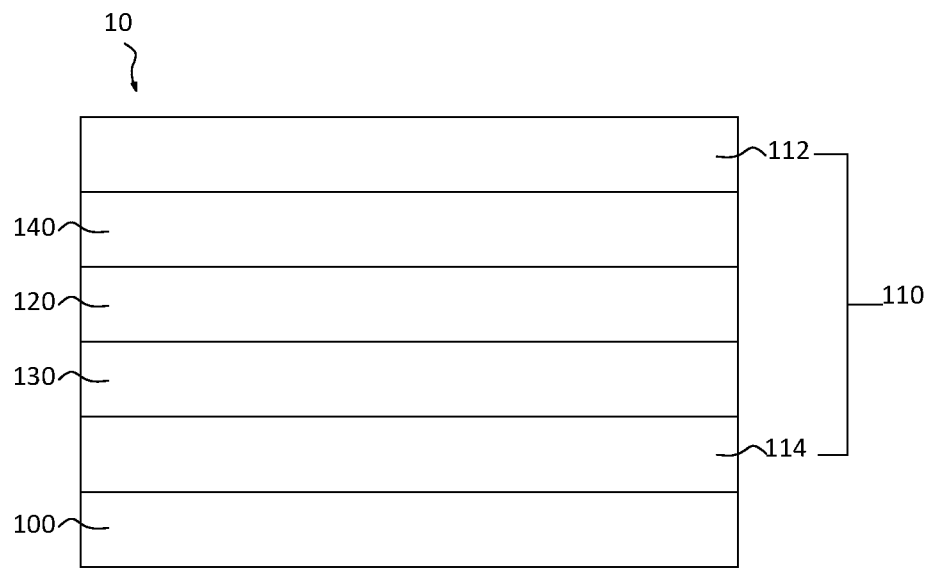

In a fifth embodiment shown in FIG. 1E, the respective components of the organic optoelectronic device 10 of this embodiment are arranged the same as those of the second embodiment but the organic optoelectronic device 10 further includes a first carrier transporting layer 130 arranged between the second electrode 114 and the active layer 120, and a second carrier transporting layer 140 disposed between the first electrode 112 and the active layer 120.

Figure 1F:
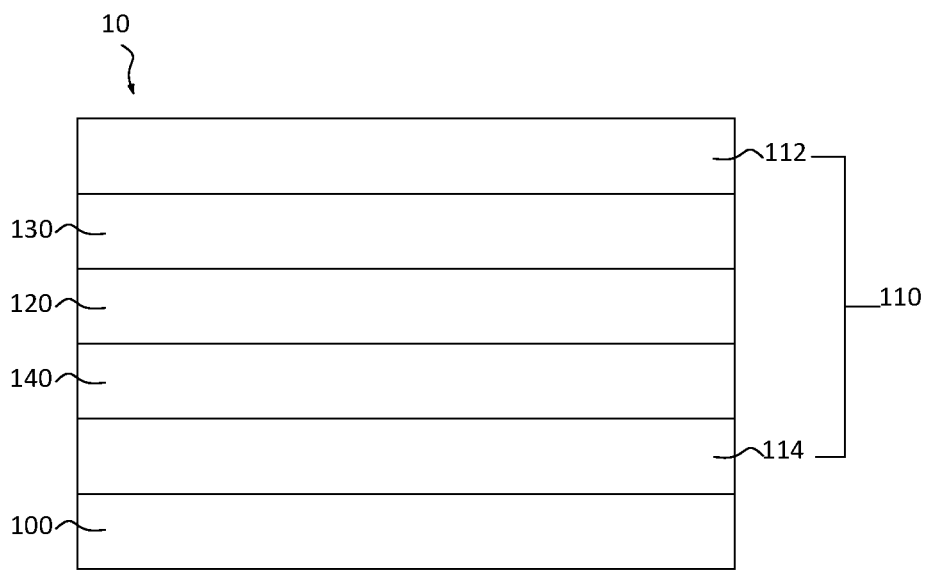

In a sixth embodiment shown in FIG. 1F, arrangement of the respective components of the organic optoelectronic device 10 is the same as that of the second embodiment. The organic optoelectronic device 10 further includes a first carrier transporting layer 130 and a second carrier transporting layer 140. The first carrier transporting layer 130 is arranged between the first electrode 112 and the active layer 120 while the second carrier transporting layer 140 is disposed between the second electrode 114 and the active layer 120.

In the third to sixth embodiments mentioned above, material for the first carrier transporting layer 130 is selected from the followings: conjugated polymer electrolytes such as PEDOT:PSS, polymeric acid such as polyacrylate, conjugated polymers such as Poly[bis(4-phenyl)(2,4,6-triMethylphenyl)aMine] (PTAA), insulating polymer such as Nafion film, Polyethylenimine and Polystyrene sulfonates, polymer doped with metal oxides including MoOx, NiOx, WOx, SnOx, organic small molecule compounds such as N,N'-diphenyl-N,N'-bis-(1-naphthyl) (1,1'-biphenyl)-4,4' diamine (NPB), N,N'-diphenyl-N,N'-(3-aminomethyl phenyl)-1,1'-biphenyl-4,4'-diamine (TPD), or combinations thereof.

In the third to sixth embodiments mentioned above, material for the second carrier transporting layer is selected from the followings, conjugated polymer electrolytes such as polyethylenimine, conjugated polymer such as poly[3-(6-trimethylammoniumhexyl) thiophene], poly[9,9-bis(2-ethylhexyl)fluorene]-b-poly[3-(6-trimethylanmmoniumhexyl)thiophene], or poly[(9,9-bis(3'-(N,N-dimethylamino)propyl)-2,7-fluorene)-alt-2,7-(9,9-dioctylfluorene)], organic small molecule compound such as Tris(8-hydroxyquinoline)aluminum(III) (Alq$_3$), 4,7-diphenyl-1,10-phenanthroline, metal oxides such as ZnOx, aluminum-doped zinc oxide (AZO), TiOx and their nanoparticles, salts such as LiF, NaF, CsF, and CsCO$_3$, and amines such as primary amines, secondary amines, and tertiary amines.

In order to learn performance improvement of the organic optoelectronic device caused by the present organic semiconductor mixture, test properties and performance of the organic optoelectronic device. The followings are test results.

spectrum for measurement of thermal stability

Use Hitachi UV-Visible/NIR Spectrophotometer UH5700 to measure absorption spectrum of samples. A sample solution is prepared by using compound 1:D1, compound 2:D1, compound 3:D1, and compound 8:D1=1.2:1 in chloroform containing 0.5% 1-chloronaphthalene with total dissolved solids of 11 mg/mL while compound 4:D1 and compound 9:D1=1.2:1 are prepared in chloroform with total dissolved solids of 11 mg/mL. Compound 5:D2 and compound 10:D2 with a ratio of 1.2:1 are prepared in chloroform with total dissolved solids of 20 mg/mL while compound 6:D3, compound 7:D3, and compound 11:D3 with a ratio of 1.2:1 are prepared in o-xylene with total dissolved solids of 20 mg/mL After being prepared, the above sample is coated on the substrate made of glass by spin coating to form a thin film with a thickness of about 100 nm. Then bake and dry at 100° C. for 1 minute and measure absorption spectrum of the solid thin film.

Take a heating plate and increase the temperature up to 40° C. Bake the thin film for 5 minutes, take out and cool down the thin film, and measure absorption spectrum. Then increase the temperature to the next temperature (60° C.) and bake for 5 minutes. Then take out and cool down the thin film, and measure absorption spectrum again. Repeat the above steps until the absorption spectrum has a significant change at certain temperature (or the highest temperature 220° C.). Next compare the amount of change in spectra of the thin films of the respective mixtures.

preparation and test of organic optoelectronic device

Use glass with sheet resistance and patterned ITO coating as a substrate and treat by ultrasonic vibration in neutral detergent, deionized water, acetone, and isopropanol in turn. The substrate is washed for 15 minutes in each step. The washed substrate is further cleaned by UV-O$_3$ treatment for 15 minutes. Then coat ZnO on the ITO substrate by spin coating. Bake in the air at 150° C. for 20 minutes. Next prepare an active layer solution (weight ratio of p-type material to n-type material=1:1.2) in a selected solvent (total dissolved solids and the solvent used are shown in the following table). In order to dissolve the polymer completely, the active layer solution is stirred on a heating plate at 100° C. for at least 3 hours. Then place the solution at room temperature and perform coating after cool down. Later the thin film is annealed for 5 minutes at the temperature selected (as shown in the following table). Then place the thin film into an evaporator. Deposit a thin film of molybdenum trioxide (8 nm) used as the carrier transport layer and silver think film (100 nm) used as external electrode under vacuum of $3 \times 10^{-6}$ Torr. Then measure J-V properties of the organic optoelectronic device in the air at morn temperature using a solar simulator (100 mW cm$^{-2}$ xenon lamp with AM1.5G filter) under light intensity of 1000 W/m$^2$ AM1.5G. Standard silicon diode with KG5 filter is used as reference cell for calibration of light intensity and calibrated by third party before use. Use Keithley™ 2400 source meter to record the J-V properties. The cell area is 4 mm$^2$ and the area is defined by a metal mask aligned with the organic optoelectronic device. The structure of the organic optoelectronic device is glass/ITO/ZnO/ATL/MoO$_3$/Ag and formulation of the active layer and the annealing temperature of the organic optoelectronic device are shown in the table 1.

TABLE 1 formulation of the active layer and annealing temperature of the organic optoelectronic devices

| n-type material | p-type material | total dissolved solids | solvent used | Annealing temperature (□) |
|---|---|---|---|---|
| compound 1 compound 2 compound 3 compound 8 | D1 | 11 mg/ml | chloroform + 0.5% 1-chloronaphthalene | 120 |
| compound 4 compound 9 | | | chloroform | 100 |
| compound 5 compound 10 | D2 | 20 mg/mL | chloroform | 80 |
| compound 6 compound 7 compound 11 | D3 | 20 mg/mL | o-xylene | 80 | measurement of thermal stability of organic optoelectronic device preparation and test of organic optoelectronic device Use glass with sheet resistance and patterned ITO coating as a substrate and treat by ultrasonic vibration in neutral detergent, deionized water, acetone, and isopropanol in turn. The substrate is washed for 15 minutes in each step. The washed substrate is further cleaned by UV-ozone cleaner for 15 minutes. Then coat ZnO on the ITO substrate by spin coating. Bake in the air at 15° C. for 20 minutes. Next prepare an active layer solution (weight ratio of p-type material to n-type material=1:1.2) in a selected solvent (total dissolved solids and the solvent used are shown in the following table). In order to dissolve the polymer completely, the active layer solution is stirred on a heating plate at 100° C. for at least 3 hours. Then place the solution at room temperature and perform coating after cool down. Later the thin film is annealed for 5 minutes (as shown in the following list). Bake test specimen (sample) before evaporation (annealing and bake temperature are shown in the following stable). Then place the thin film into an evaporator after completing baking. Deposit a thin film of molybdenum trioxide (8 nm) used as the carrier transport layer and silver think film (100 nm) used as external electrode under vacuum of $3 \times 10^{-6}$ Torr. Then measure J-V properties of the organic optoelectronic device in the air at room temperature using a solar simulator (100 mW cm$^{-2}$ xenon lamp with AM1.5G filter) under light intensity of 1000 W/m$^2$ AM1.5G. Standard silicon diode with KG5 filter is used as reference cell for calibration of light intensity and calibrated by third party before use. Use Keithley™ 2400 source meter to record the J-V properties. The cell area is 4 mm$^2$ and the area is defined by a metal mask aligned with the organic optoelectronic device. The structure of the organic optoelectronic device is glass/ITO/ZnO/ATI/MoO$_3$/Ag and formulation of the active layer, annealing temperature, and forging temperature of the organic optoelectronic device are shown in the table 2.

TABLE 2 formulation of the active layer, annealing temperature, and forging temperature of organic optoelectronic device

| n-type material | p-type material | total dissolved solids | solvent used | annealing temperature (° C.) | baking temperature (° C.) |
|---|---|---|---|---|---|
| compound 1 compound 2 compound 3 compound 8 | D1 | 11 mg/mL | chloroform + 0.5% 1-chloronaphthalene | 120 | 180 |
| compound 4 compound 9 | | | chloroform | 100 | 140 |
| compound 5 compound 10 | D2 | 20 mg/mL | chloroform | 80 | 160 |
| compound 6 compound 7 compound 11 | D3 | 20 mg/mL | o-xylene | 80 | 120 160 |

The thin film of the active layer is processed by different baking temperature for discussion of material stability. The baking temperature is ranging from room temperature to 200° C.

Figure 2A:
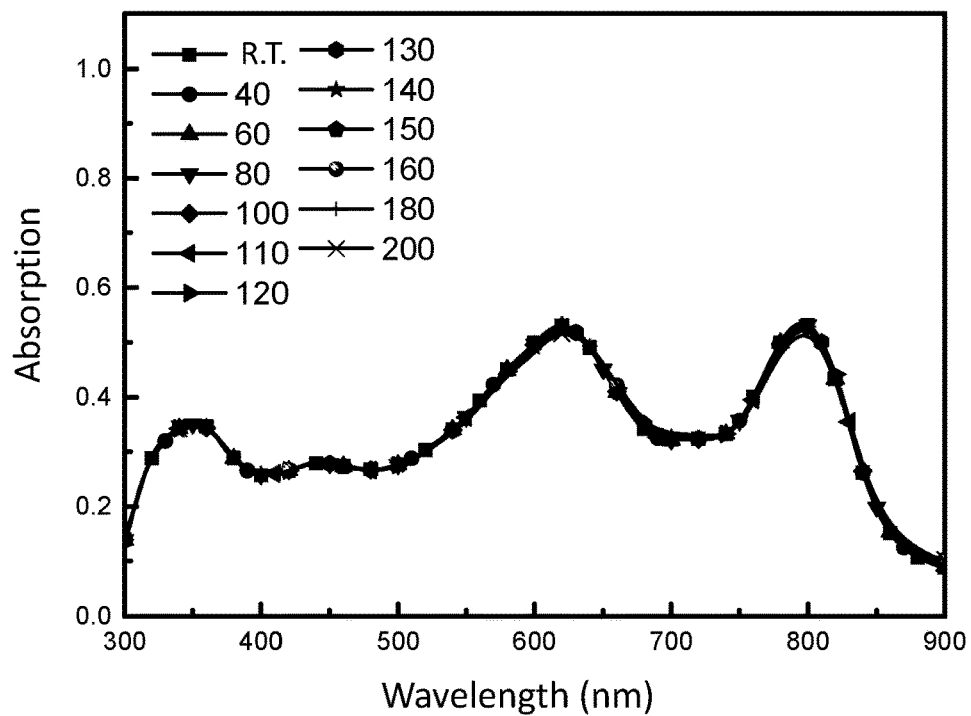
FIG. 2A-2D are spectra showing test results of different embodiments of an organic optoelectronic device according to the present invention.
Figure 2B:
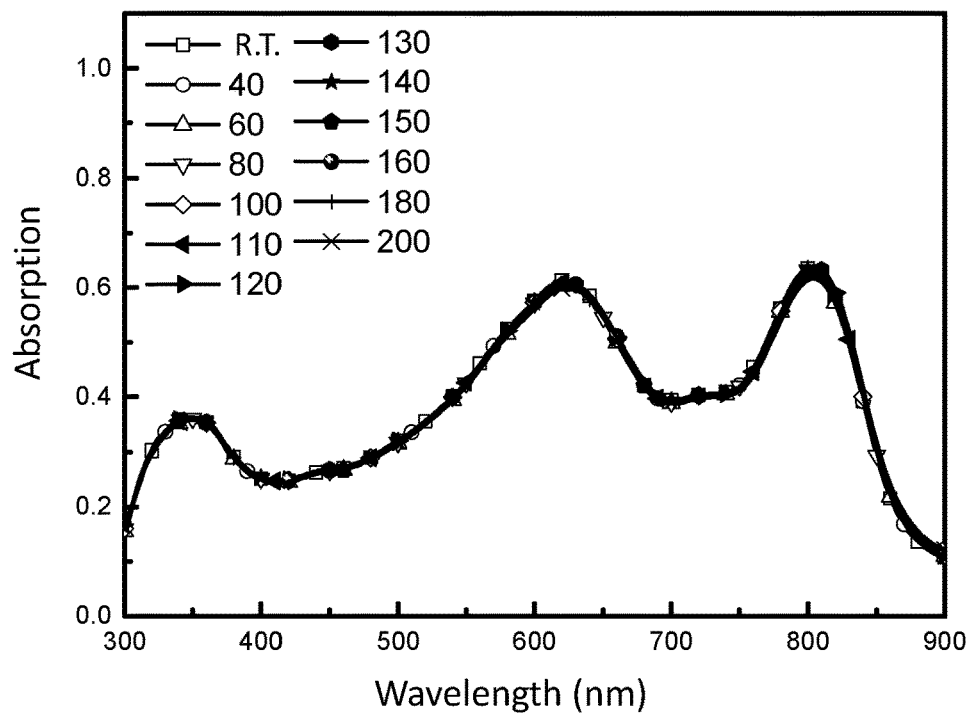
Figure 2C:
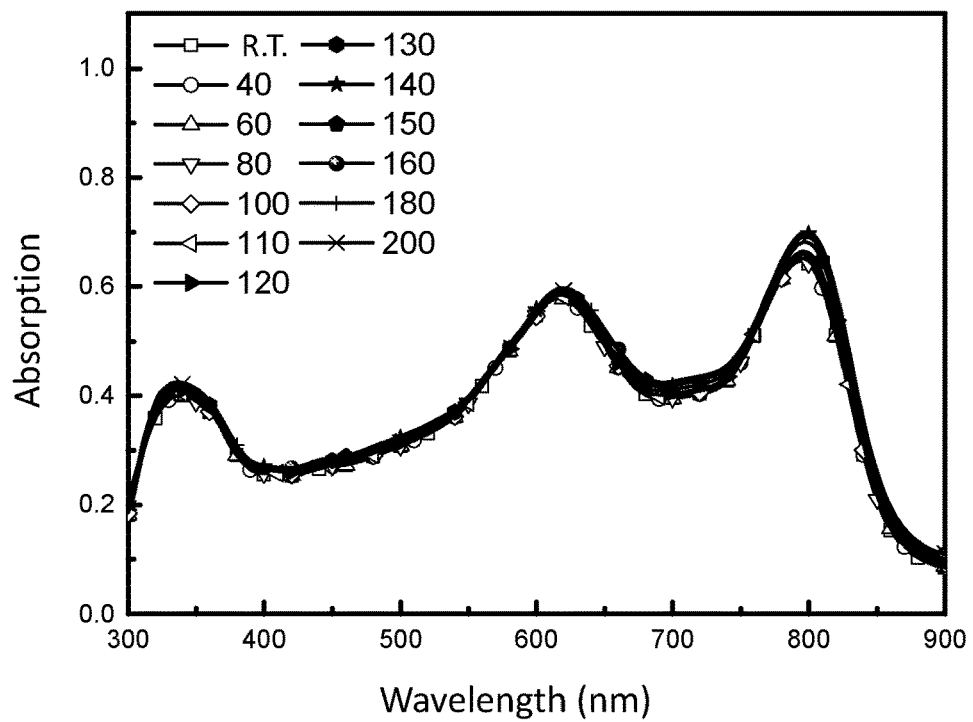

The test results show that spectra of the mixture of compound 1/D and the mixture of compound 2/D2 have no changes in patterns along with the increasing temperature (as shown in FIG. 2A and FIG. 2B). This means the thin film of both the mixtures has better thermal stability. Although spectrum of the mixture of compound 3/D1 has some changes at 130° C., the spectrum patterns over 140° C. keep the same, without continuous changes (as shown in FIG. 2C).

Figure 2D:
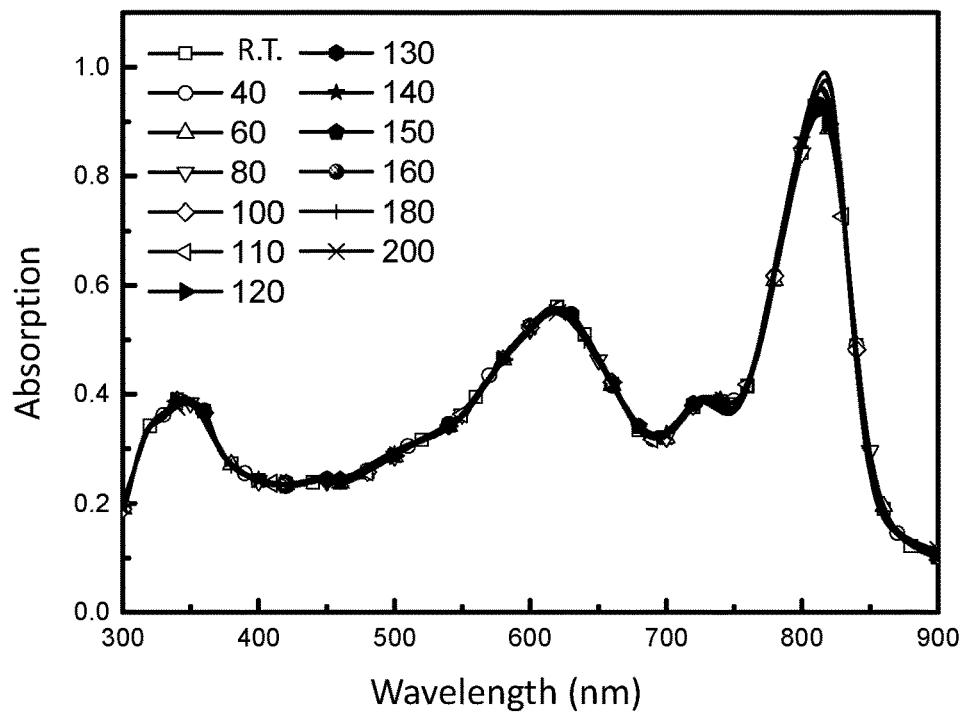

Among results of comparative examples, the mixture of compound 8/D1 has a slight change in the spectrum pattern contiguously between 120° C. and 200° C. (as shown in FIG. 2D). This means the thin film of the mixture of the compound 8/D1 continues to have changes during heating process and thus the thermal stability of the thin film of the mixture of the compound 8/D1 is less than thermal stability of the mixture of the compound/D1, the mixture of compound 2/D1, and the mixture of compound 3/D1. During preparation, the annealing temperature is 120° C. for 5 minutes while the baking temperature is 180° C. for 30 minutes.

TABLE 3 performance test and film surface state of organic optoelectronic device

| n-type material | p-type material | annealing 120° C. 5 min | baking: 180° C. 30 min | $V_{oc}$ (V) | $J_{sc}$ (mA/cm$^2$) | FF (%) | PCE (%) | $PCE_{avg}$ (%) | PCE/ $PCE_{without\ forging}$ | film surfaces condition smooth | Particle/ foggy |
|---|---|---|---|---|---|---|---|---|---|---|---|
| compound 8 | D1 | V | X | 0.91 | 21.08 | 60.88 | 11.65 | 11.32 | — | V | |
| | | V | V | 0.87 | 4.76 | 30.58 | 1.28 | 1.03 | 9.1% | | V |
| compound 1 | | V | X | 0.96 | 20.87 | 60.40 | 12.13 | 11.80 | — | V | |
| | | V | V | 0.94 | 20.28 | 64.29 | 12.33 | 12.10 | 102.5% | V | |
| compound 2 | | V | X | 0.96 | 18.08 | 58.71 | 10.15 | 9.97 | — | V | |
| | | V | V | 0.95 | 16.76 | 63.21 | 10.03 | 9.86 | 98.9% | V | |
| compound 3 | | V | X | 0.94 | 10.87 | 53.97 | 5.50 | 5.41 | — | V | |
| | | V | V | 0.92 | 9.97 | 61.20 | 5.60 | 5.48 | 101.3% | V | |

According to test results, the comparative example of the compound 8/D1 has an initial efficiency up to 11.32% while being treated by only annealing without baking in the beginning. But the efficiency of the organic optoelectronic device with baking is reduced from 11.32% to 1.03%. This shows that the thin film of the mixture used as the active layer of the organic optoelectronic device has phase changes after being heated and the phase changes lead to a reduction in efficiency of the organic optoelectronic device. By contrast, the embodiments of the compound 1/D1, the compound 2/D1, and the compound 3/D1 keep the initial efficiency of the organic optoelectronic device up to 95% after baking at 180° C. for 30 minutes no matter the initial efficiency of the organic optoelectronic device is high or low. Thereby the mixture of the compound 1/D1, the mixture of the compound 2/D1, and the mixture of the compound 3/D1 have better thermal stability compared with the mixture of the compound 8/D1.

Moreover, the thin film of the active layer is processed by different baking temperature for discussion of material stability. The spectrum is measured from room temperature to 160° C. The results show that the comparative example (mixture of compound 9/D1) has obvious change in the spectrum pattern (as shown in FIG. 3A) after being heated at 140□ for 5 minutes while the spectrum of the mixture of compound 4/D1 only has a small magnitude of change in the pattern after being heated at 160□ for 5 minutes (as shown in FIG. 3B). This means film thermal stability of the mixture of the compound 9/D1 is poor compared with that of the mixture of the compound 4/D1, also refer to table 4 to learn test results.

TABLE 4 performance test and film surface state of organic optoelectronic device

| n-type material | p-type material | annealing 100□ 5 min | baking 140□ 30 min | $V_{oc}$ (V) | Jsc (mA/cm$^2$) | FF (%) | PCE (%) | PCE$_{avg.}$ (%) | PCE/ PCE$_{without\ forging}$ | film surface state smooth | Particle/ foggy |
|---|---|---|---|---|---|---|---|---|---|---|---|
| compound 9 | D1 | V | X | 0.89 | 20.65 | 66.27 | 12.20 | 12.07 | — | V | |
|  |  | V | V | 0.89 | 8.94 | 50.11 | 3.98 | 3.58 | 30% | | V |
| compound 4 |  | V | X | 0.96 | 18.43 | 53.53 | 9.53 | 9.33 | — | V | |
|  |  | V | V | 0.95 | 18.62 | 53.32 | 9.45 | 9.13 | 98% | V | |

Take a look at an appearance of the organic optoelectronic device made from the mixture being baked at 140° C. for 30 min. After baking, a film of the embodiment of the mixture of compound 4/D1 has smooth and intact appearance. Also observe the comparative example, a film surface of the mixture of compound 9/D1 used as the active layer after baking is foggy and the electrode is also foggy after baking. These all indicate that surface of the film being baked is different from that of the film without being baked.

According to the above results, it is learned that the comparative example of compound 9/D1 treated by annealing without baking has an initial efficiency of 12.07% while the efficiency is dropped from 12.07% to 3.58% after baking. The results show that the blend film used as the active layer of the organic optoelectronic device has phase change after being heated and the phase change further causes a reduction in efficiency of the organic optoelectronic device. By contrast, an initial efficiency of the embodiment of compound 4/D1 treated by annealing without baking is 9.33%. After being baked at 140° C. for 30 min, the initial efficiency of the organic optoelectronic device is maintained at 98% of the initial efficiency. The results show that the mixture of compound 4/D has better thermal stability than the mixture of the compound 9/D1.

Among the test results, the mixture of compound 10/D2 used as the comparative example has obvious and continuous change in the spectrum after being heated at 100° C. for 5 min (as shown in FIG. 4A) while the spectrum of the mixture of compound 5D2 don't have obvious change after being heated up to 160° C. for 5 min (as shown in FIG. 4B). This means the thermal stability of the film of the mixture of the comparative example is lower than that of the mixture of compound 5/D2. The results are shown in Table 5.

According to the above results, the comparative example of the mixture of compound 10/D2 has an initial efficiency of 8.58% while being treated only by annealing without baking in the beginning but the efficiency is dropped from 8.58% to 7.33% after baking. The results show that the blend film used as the active layer of the organic optoelectronic device has phase change after being heated and the phase change further causes a reduction in efficiency of the organic optoelectronic device. By contrast, an initial efficiency of the embodiment of compound 5/D2 treated by annealing without baking is 5.49%. After being forged at 160° C. for 30 min, the initial efficiency of the organic optoelectronic device is increased up to 122% of the initial efficiency. The results show that the mixture of compound 5/D2 not only has higher thermal stability than the mixture of the compound 10/D2, but also more suitable for high-temperature process during manufacturing of the organic optoelectronic device.

The thin film of the active layer is processed by different baking temperature for discussion of material stability. The spectrum is measured from room temperature to 160°. The results show that the comparative example of the mixture of compound 11/D3 has obvious and continuous change in the spectrum (as shown in FIG. 5A) from being heated at 100° C. to 160° C. while the spectra of the embodiments of compound 6/D3 and compound 7/D3 have no changes in the patterns along with the increasing temperature (as shown in FIG. 5B and FIG. 5C). This means both embodiments have better thermal stability. The results shown in table 6 indicate that the blend film of the compound 11/D3 keeps changing during the heating process and the thermal stability of the mixture of compound 11/D3 film is poor than the embodiments of the mixture of compound 6/D3 and the mixture compound 7/D3.

TABLE 5 performance test and film surface state of organic optoelectronic device

| n-type material | p-type material | annealing 80° C. 5 min | baking 160° C. 30 min | $V_{oc}$ (V) | $J_{sc}$ (mA/cm$^2$) | FF (%) | PCE (%) | PCE$_{avg.}$ (%) | PCE/ PCE$_{without\ forging}$ | film surface state smooth | Particle/ foggy |
|---|---|---|---|---|---|---|---|---|---|---|---|
| compound10 | D2 | V | X | 0.64 | 23.17 | 58.03 | 8.68 | 8.58 | — | V | |
|  |  | V | V | 0.65 | 18.56 | 63.85 | 7.68 | 7.33 | 85% | V | |
| compound 5 |  | V | X | 0.70 | 16.38 | 48.52 | 5.53 | 5.49 | — | V | |
|  |  | V | V | 0.70 | 18.02 | 53.67 | 6.78 | 6.68 | 122% | V | |

TABLE 6 performance test and film surface state of organic optoelectronic device

| N-type material | P-type material | annealing: 80° C. 5 min | baking: 120° C. 30 min | forging: 160° C. 30 min | $V_{oc}$ (V) | $J_{sc}$ (mA/cm$^2$) | FF (%) | PCE (%) | PCE$_{avg.}$ (%) | PCE/ PCE$_{without\,forging}$ | film surface state smooth | particle/ foggy |
|---|---|---|---|---|---|---|---|---|---|---|---|---|
| compound11 | D3 | V | X | X | 0.90 | 16.11 | 69.08 | 9.98 | 9.86 | — | V | |
| | | V | V | X | 0.89 | 12.27 | 60.27 | 6.60 | 6.53 | 66% | V | |
| | | V | X | V | 0.88 | 9.17 | 50.35 | 4.08 | 4.04 | 41% | V | |
| compound 6 | | V | X | X | 0.96 | 14.00 | 62.22 | 8.33 | 8.23 | — | V | |
| | | V | V | X | 0.94 | 13.80 | 65.00 | 8.48 | 8.33 | 101% | V | |
| | | V | X | V | 0.95 | 9..28 | 50.61 | 4.48 | 4.39 | 53% | V | |
| compound 7 | | V | X | X | 0.96 | 14.31 | 64.69 | 8.80 | 8.68 | — | V | |
| | | V | V | X | 0.95 | 15.13 | 65.84 | 9.48 | 9.28 | 107% | V | |
| | | V | X | V | 0.94 | 14.62 | 67.59 | 9.28 | 9.05 | 104% | V | |

According to the above results, the comparative example of the mixture of compound 11/D3 has an initial efficiency of 9.86% while being treated only by annealing without baking in the beginning but the efficiency is decreased from 9.86% to 6.53% after baking at 120° C. for 30 min. The efficiency of the comparative example of the mixture of compound 11/D3 being baked at 160° C. for 30 min is further dropped to 4.04%. The results show that the blend film used as the active layer of the organic optoelectronic device has phase change after being heated and the phase change further causes a reduction in efficiency of the organic optoelectronic device. The higher the baking temperature, the larger the reduction of the efficiency. By contrast, an initial efficiency of the embodiment of the mixture of compound 6/D3 treated by annealing without baking is 8.23%. After being baked at 120° C. for 30 min, the efficiency of the organic optoelectronic device has no obvious reduction, maintained at 101% of the initial efficiency. Yet after baking at 160° C. for 30 min, the efficiency of the embodiment of the mixture compound 6/D3 is dropped to 53% of the efficiency of the organic optoelectronic device without being baked. Compared with the comparative example of the mixture of compound 11/D3, the embodiment of the mixture of compound 6/D3 still has better thermal stability.

The embodiment of the mixture of compound 7/D3 treated only by annealing without baking has an initial efficiency of 8.68%. No matter being baked at 120° C. for 30 min or being baked at 160° C. for 30 min, the efficiency of the organic optoelectronic device is not reduced and even increased to 107% of the initial efficiency. The results show that the embodiment of the mixture of compound 7/D3 not only has higher thermal stability compared with the comparative example of the mixture of compound 11/D3, but also appears more suitable to be applied to high temperature process during manufacturing of the organic optoelectronic device.

In summary, the organic semiconductor mixture and the organic optoelectronic device containing the same according to the present invention have higher thermal stability and become more suitable for high temperature manufacturing process compared with the comparative examples.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalent.

What is claimed is:

1. An organic semiconductor mixture comprising a n-type organic semiconductor compound and a p-type organic semiconductor compound;

wherein the p-type organic semiconductor compound is a conjugated polymer which includes at least one acceptor unit and at least one donor unit while the n-type organic semiconductor compound is represented by formula I:

formula I

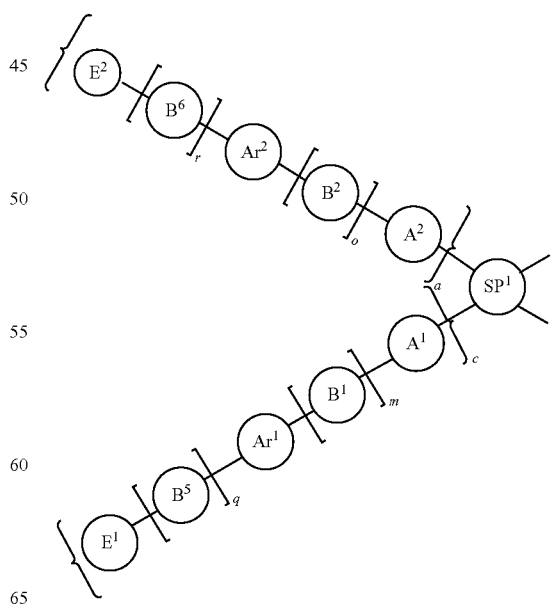

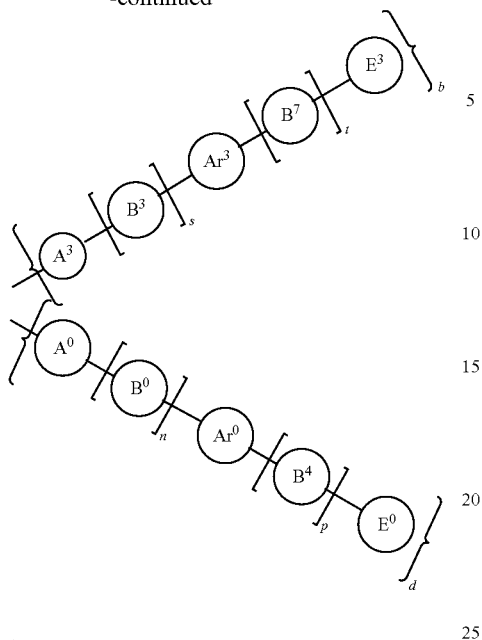

wherein SP¹ is selected from the group consisting of a vinyl group, a phenyl ring, an electron donating group, a substituted or unsubstituted monocyclic heteroaryl group containing 5 to 20 ring atoms, and a substituted or unsubstituted polycyclic heteroaryl group containing 5 to 20 ring atoms;

$Ar^0$-$Ar^3$ are substituted fused polycyclic heteroaryl groups containing 5-35 ring atoms;

$A^0$-$A^3$ are monocyclic or polycyclic heteroaryl groups containing 5-20 ring atoms and at least one electron-withdrawing group;

$B^0$-$B^7$ are selected from the group consisting of a vinyl group, a phenyl ring, an electron donating group, a substituted or unsubstituted monocyclic heteroaryl group containing 5 to 20 ring atoms, and a substituted or unsubstituted polycyclic heteroaryl group containing 5 to 20 ring atoms;

$E^0$-$E^3$ are monocyclic or polycyclic heteroaryl groups containing 5-20 ring atoms and at least one electron-withdrawing group, defined as different from the SP¹ group;

a, b, c, and d are 0 or 1 and a+b+c+d≥2; and m, n, o, p, q, r, s, and t are selected from the group consisting of 0, 1, and 2.

2. The organic semiconductor mixture as claimed in claim 1, wherein the SP¹ of the n-type organic semiconductor compound is selected from the group consisting of:

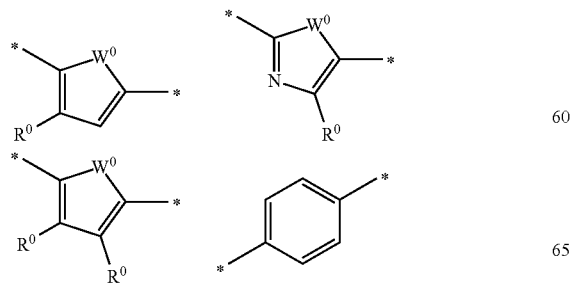

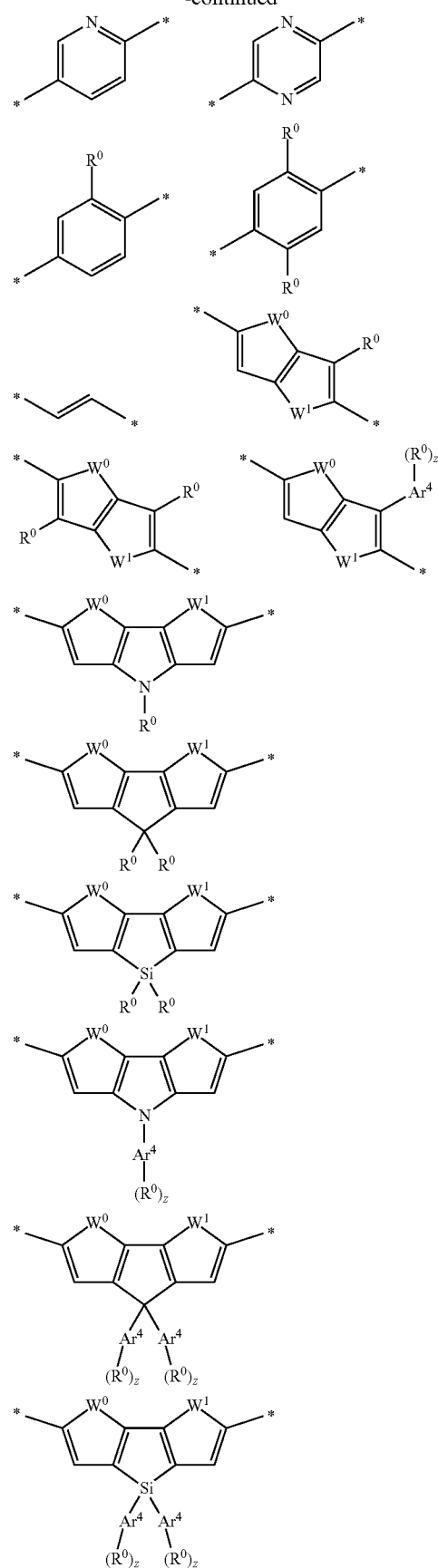

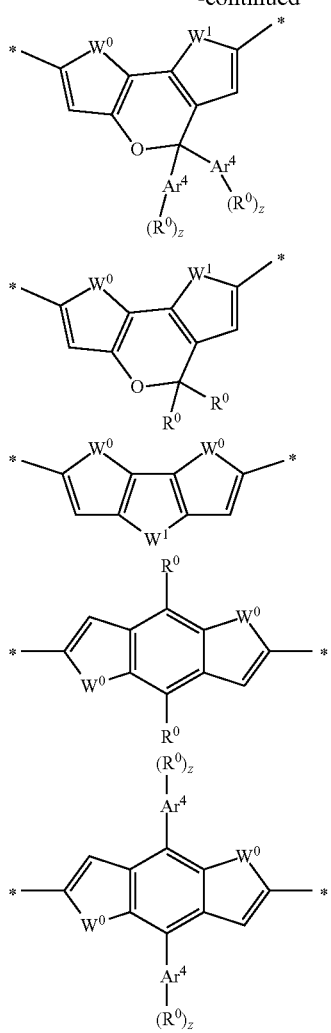

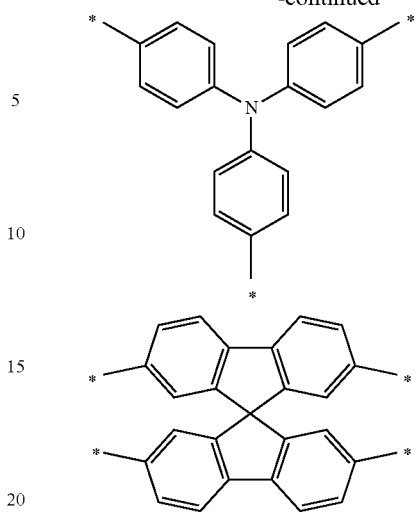

wherein $W^0$ and $W^1$ are selected from the group consisting of oxygen (O), sulfur (S), selenium (Se), and tellurium (Te);

z is an integer selected from 0 to 5;

$Ar^4$ is aromatic group or heteroaryl group containing 5 to 20 ring atoms, monocyclic, polycyclic, or fused ring, unsubstituted or substituted with at least one halogen atom; and $R^0$ is selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group.

3. The organic semiconductor mixture as claimed in claim 1, wherein the $Ar^0$, the $Ar^1$, the $Ar^2$, and the $Ar^3$ of the n-type organic semiconductor compound are selected from the group consisting of:

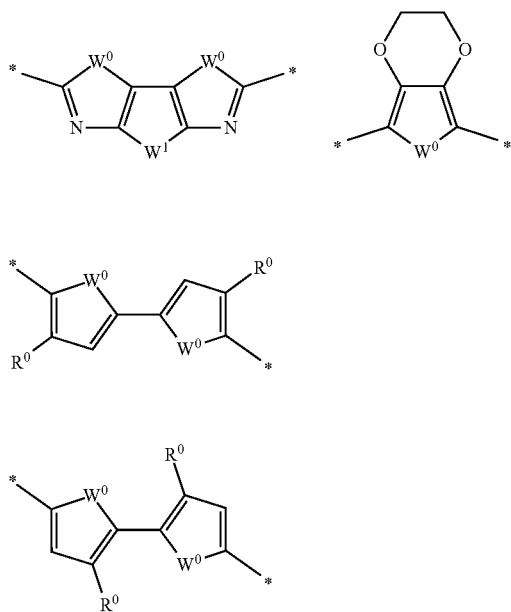

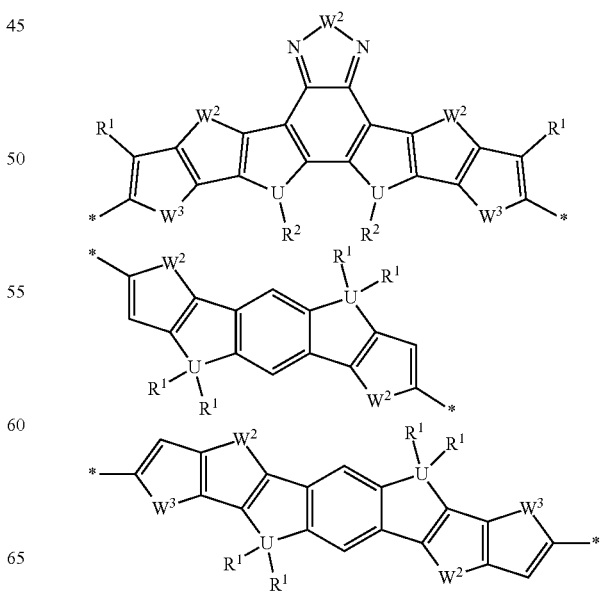

-continued

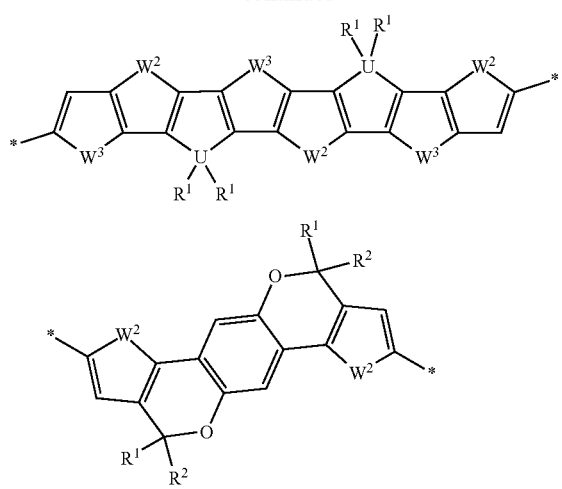

wherein W² and W³ are selected from the group consisting of oxygen (O), sulfur (S), selenium (Se), and tellurium (Te);

U is selected from the group consisting of nitrogen (N), carbon (C) and silicon (Si); and R¹ and R² are selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, C3-C30 keto-substituted alky, C1-C30 phenyl-ring-substituted alkyl, and C1-C30 heteroaryl-substituted alkyl group.

4. The organic semiconductor mixture as claimed in claim 1, wherein the $A^0$, the $A^1$, the $A^2$, and the $A^3$ of the n-type organic semiconductor compound are selected from the group consisting of:

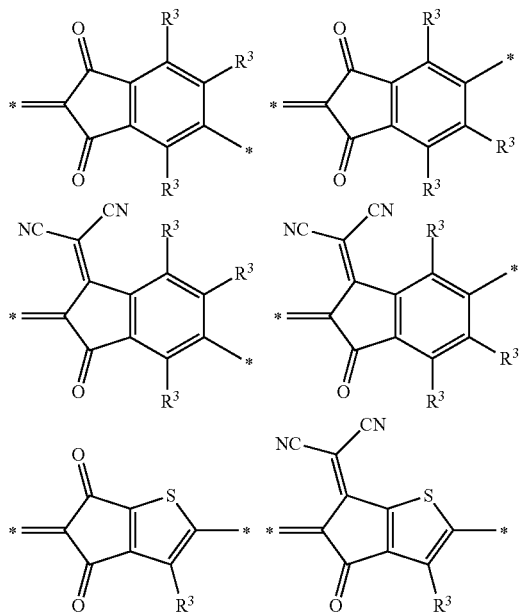

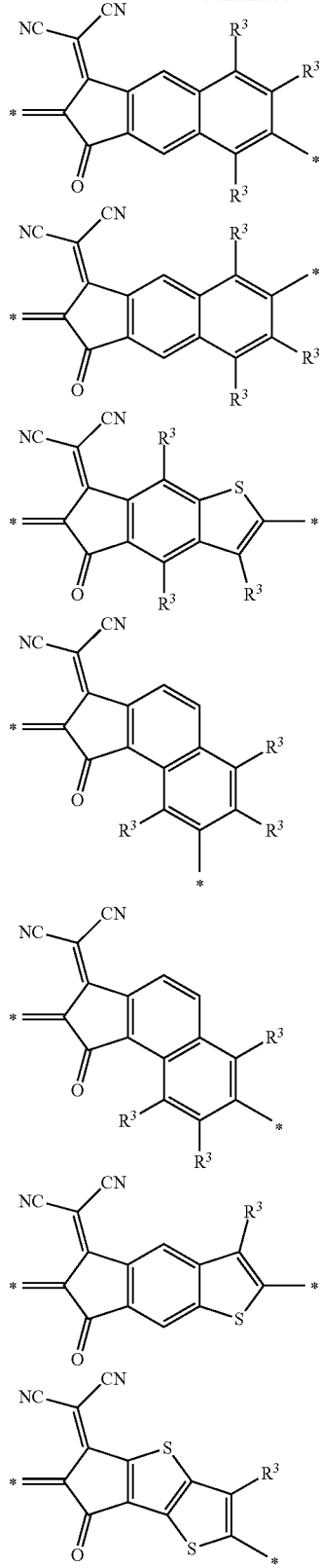

wherein R³ is selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group.
5. The organic semiconductor mixture as claimed in claim 1, wherein the $B^0$-$B^7$ of the n-type organic semiconductor compound are selected from the group consisting of:
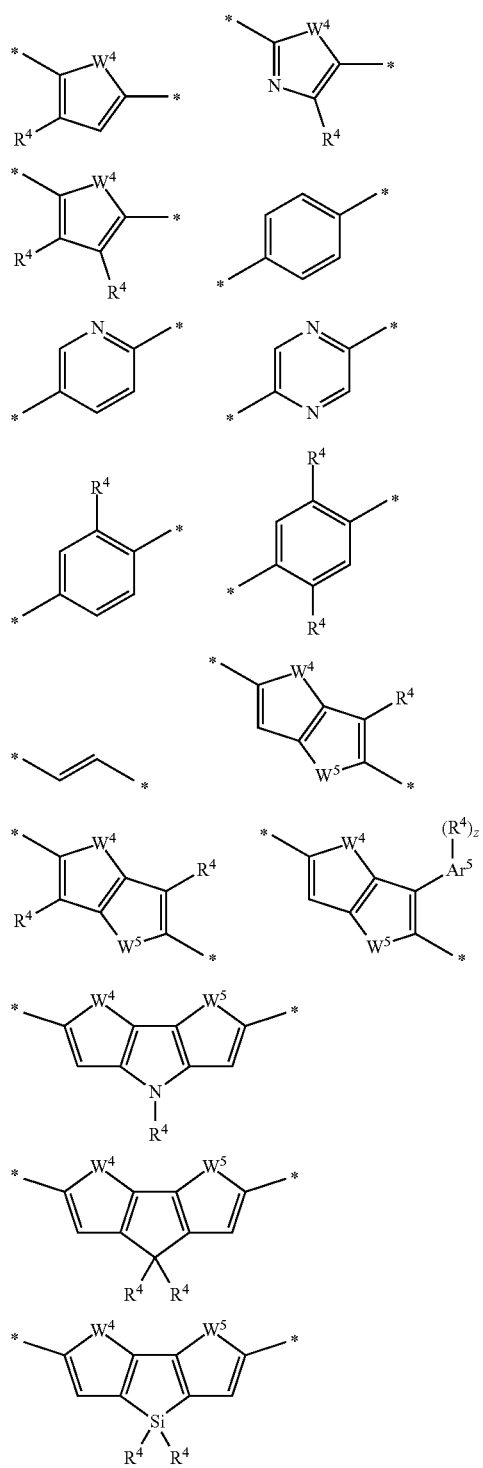
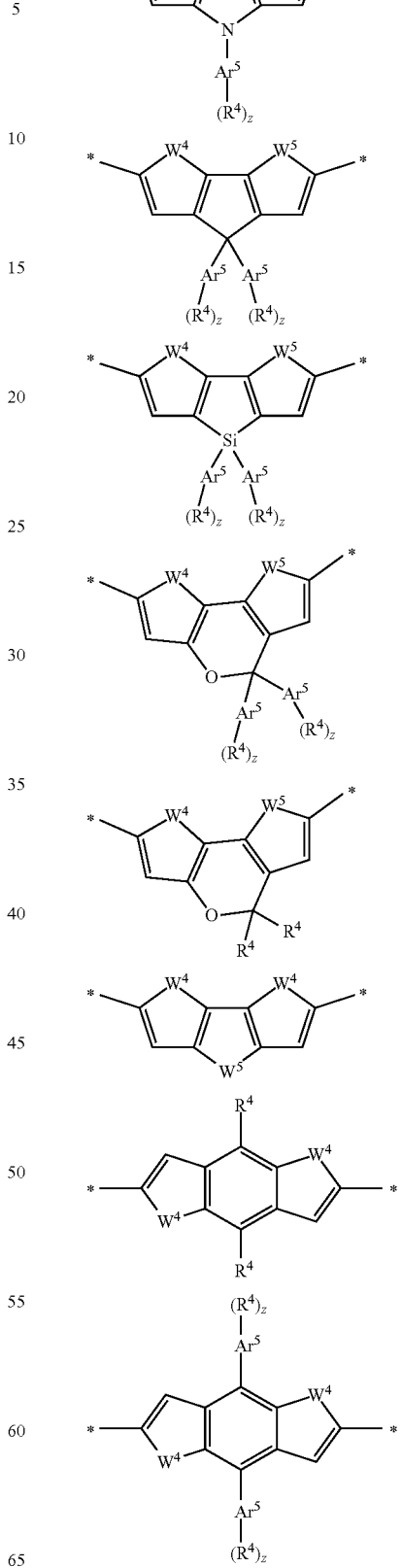

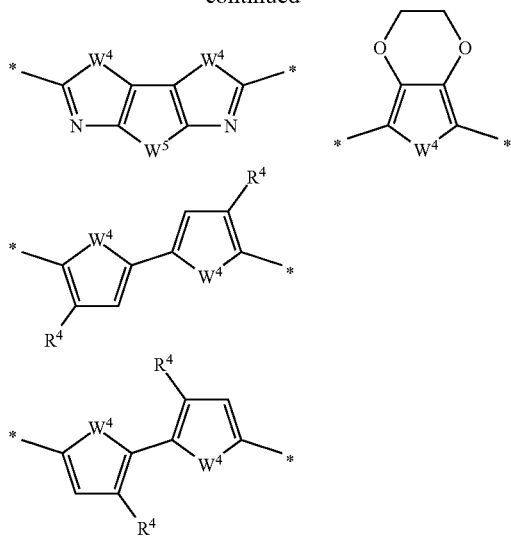

wherein W⁴ and W⁵ are selected from the group consisting of oxygen (O), sulfur (S), selenium (Se), and tellurium (Te);

z is an integer selected from 0 to 5;

Ar⁵ is aromatic group or heteroaryl group containing 5 to 20 ring atoms, monocyclic, polycyclic, or fused ring, unsubstituted or substituted with at least one halogen atom; and R⁴ is selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group.

6. The organic semiconductor mixture as claimed in claim 1, wherein the $E^0$-$E^3$ of the n-type organic semiconductor compound are selected from the group consisting of:

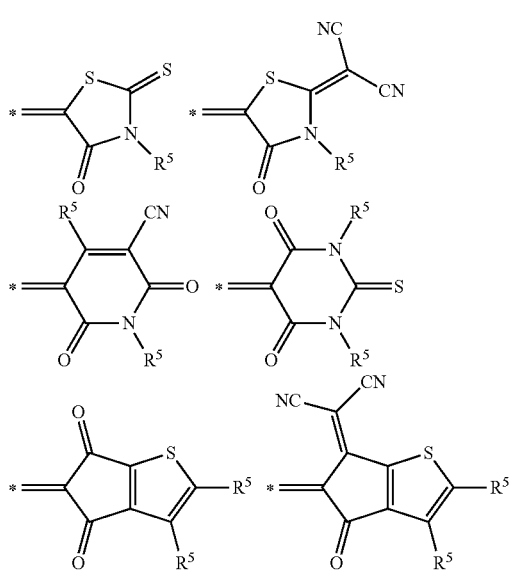

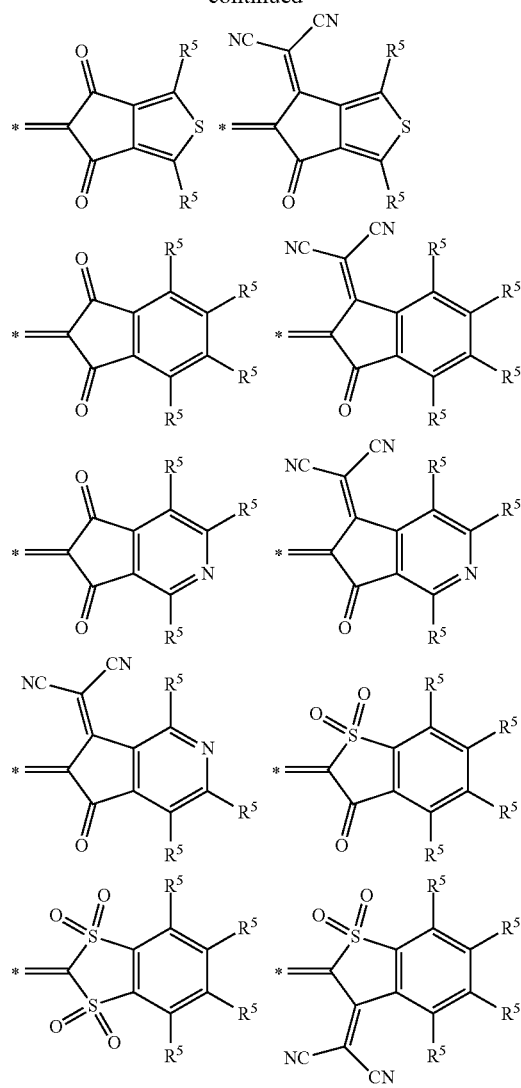

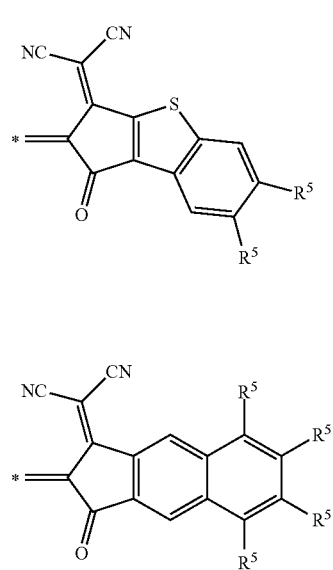

-continued

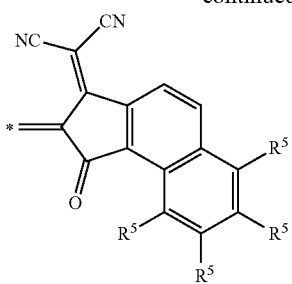

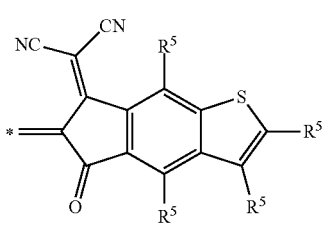

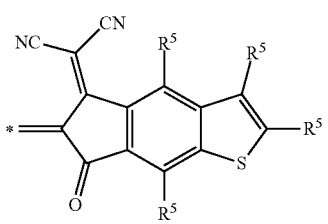

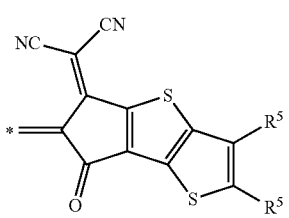

-continued

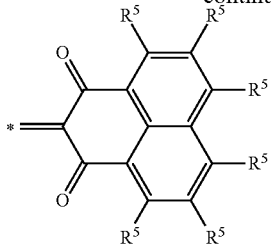

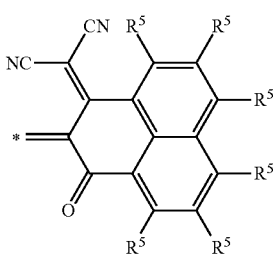

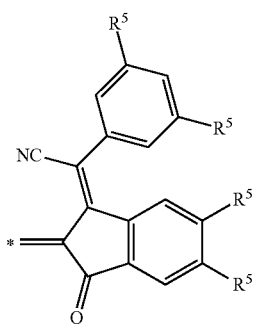

wherein $R^5$ is selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group.

7. The organic semiconductor mixture as claimed in claim 1, wherein the p-type organic semiconductor compound is represented by formula II formula II

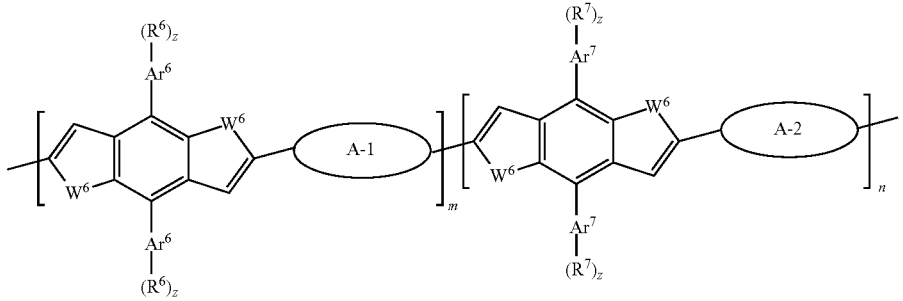

wherein A-1 and A-2 are substituted or unsubstituted polycyclic heteroaryl groups containing 5 to 35 ring atoms and also electron withdrawing groups;

$W^6$ is elected from the group consisting of oxygen (O), sulfur (S), and selenium (Se);

z is an integer selected from 0 to 5;

$Ar^6$ and $Ar^7$ are aromatic groups or heteroaryl groups containing 5 to 20 ring atoms, monocyclic, polycyclic, or fused ring, unsubstituted or substituted with at least one halogen atom;

$R^6$ and $R^7$ are selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group; and $m+n=1$, $0<m\leq 1$, $0\leq n<1$.

8. The organic semiconductor mixture as claimed in claim 7, wherein the A-1 group of the p-type organic semiconductor compound is selected from the group consisting of:

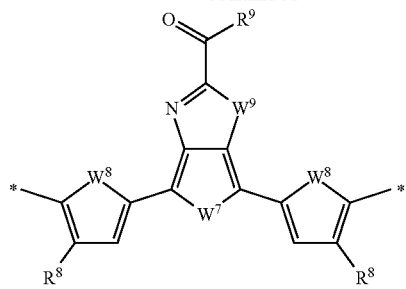

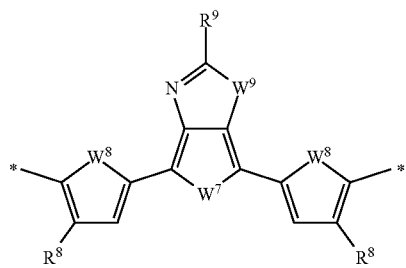

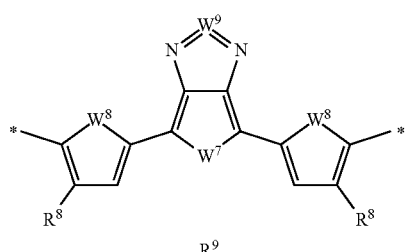

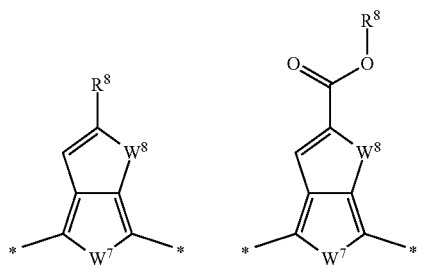

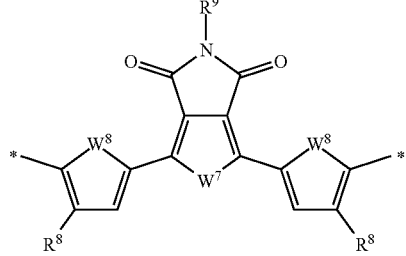

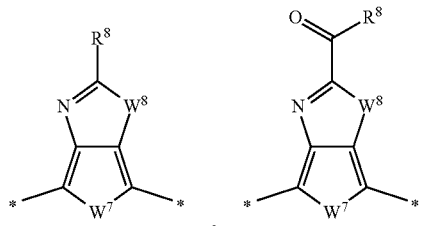

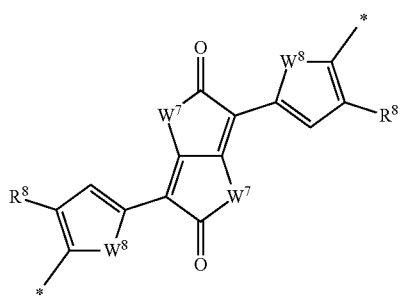

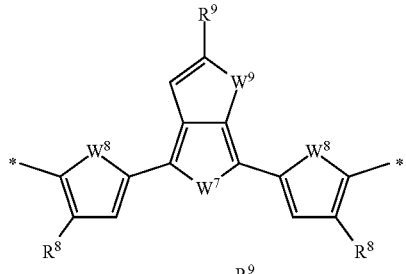

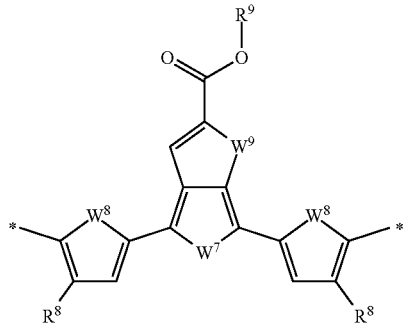

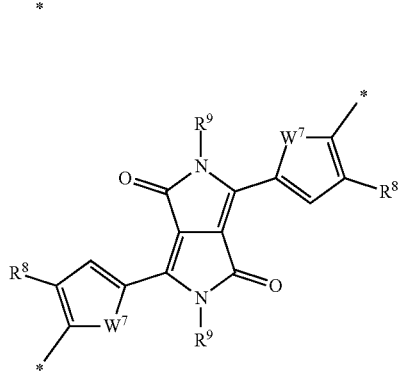

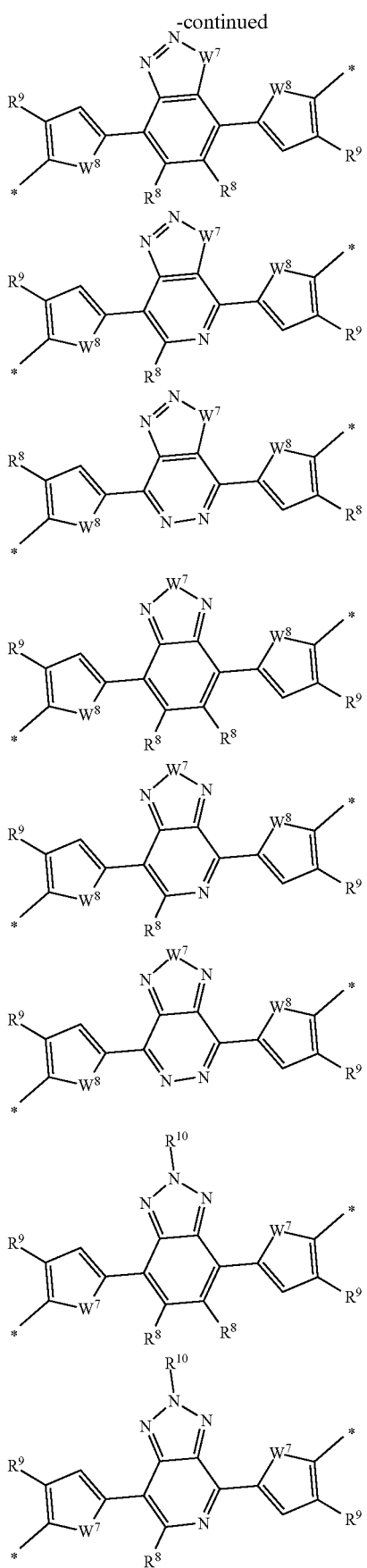
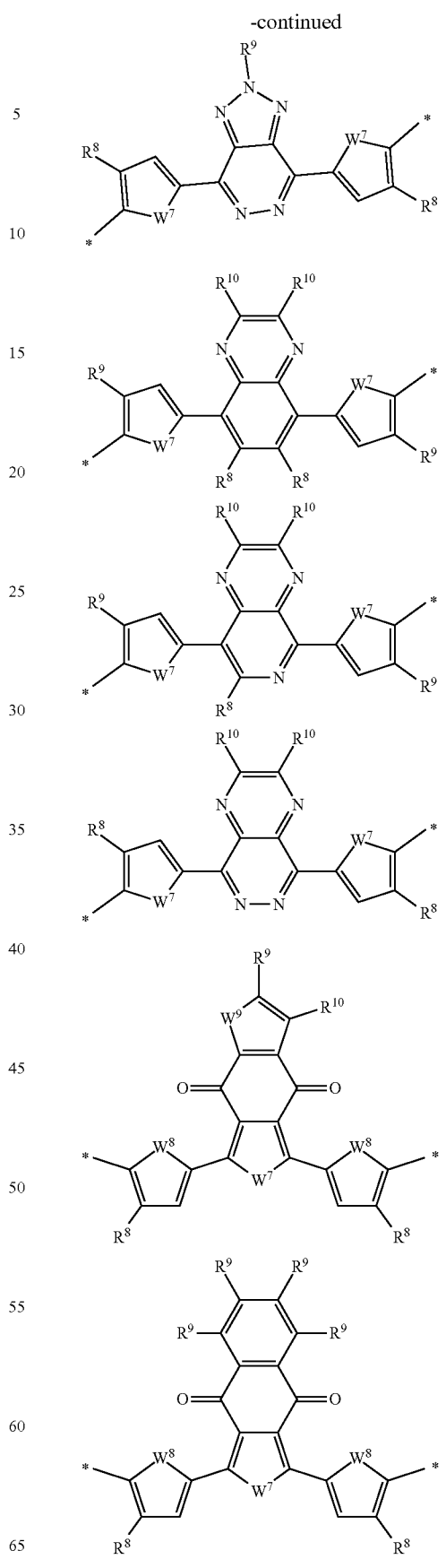

wherein $W^7$, $W^8$, and $W^9$ are selected from the group consisting of oxygen (O), sulfur (S), selenium (Se), and tellurium (Te); and $R^8$, $R^9$, and $R^{10}$ are respectively selected from the group consisting of free hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group.

9. The organic semiconductor mixture as claimed in claim 7, wherein the A-2 group of the p-type organic semiconductor compound is selected from the group consisting of:

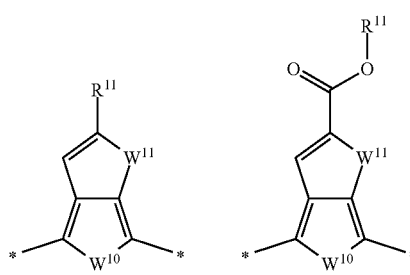

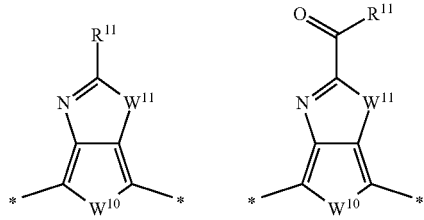

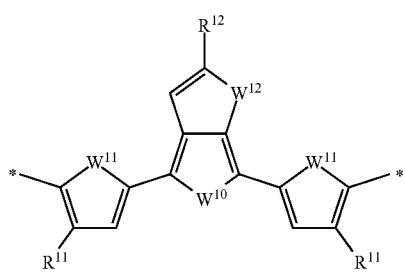

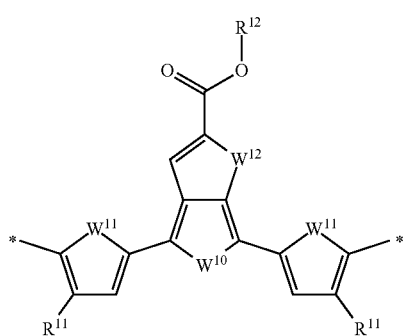

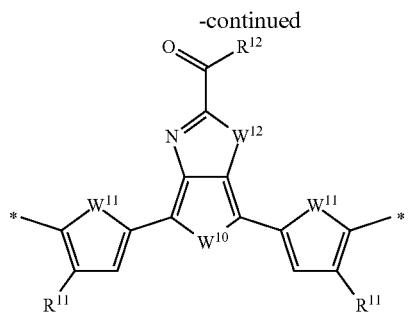

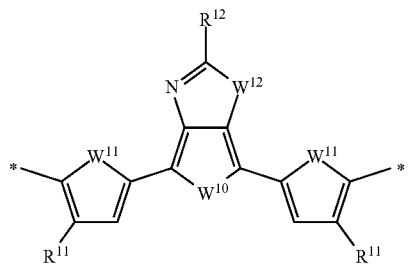

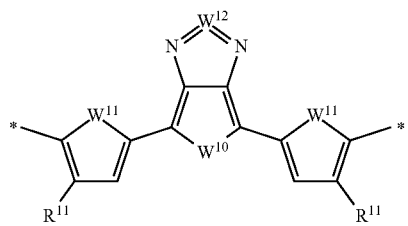

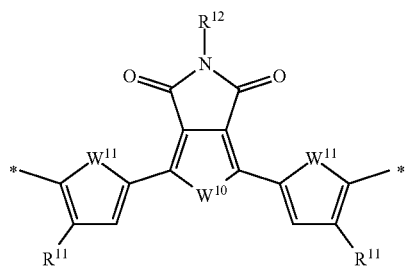

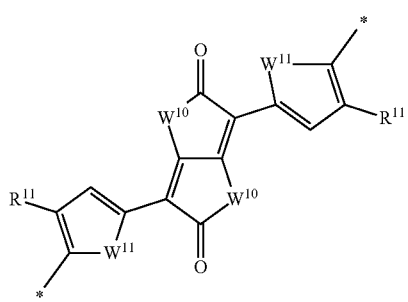

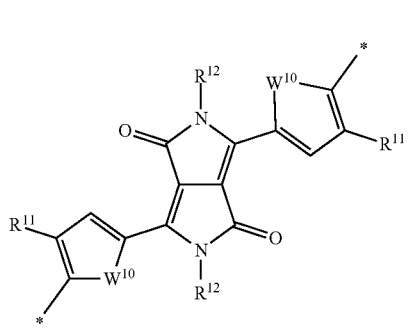

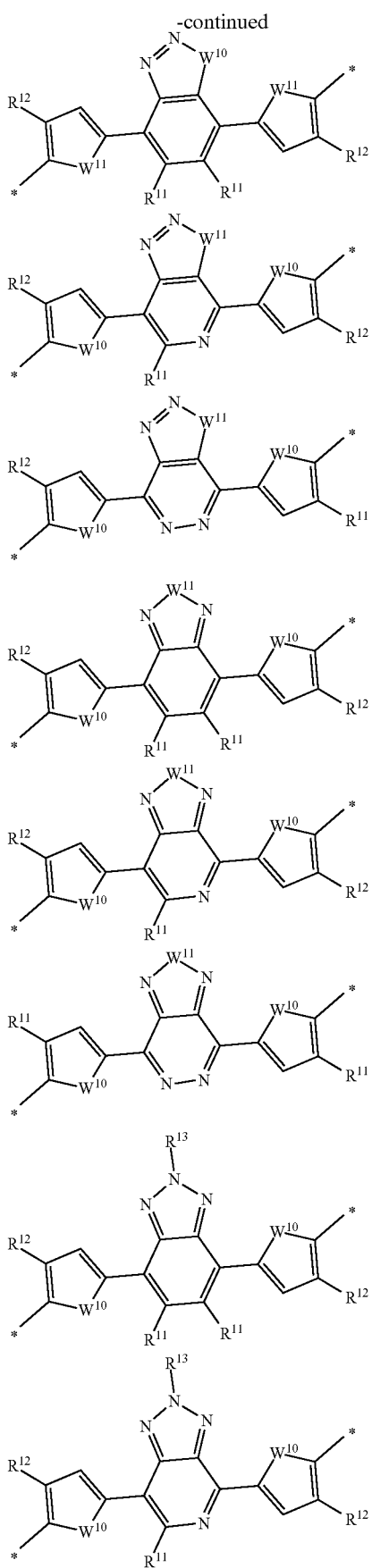
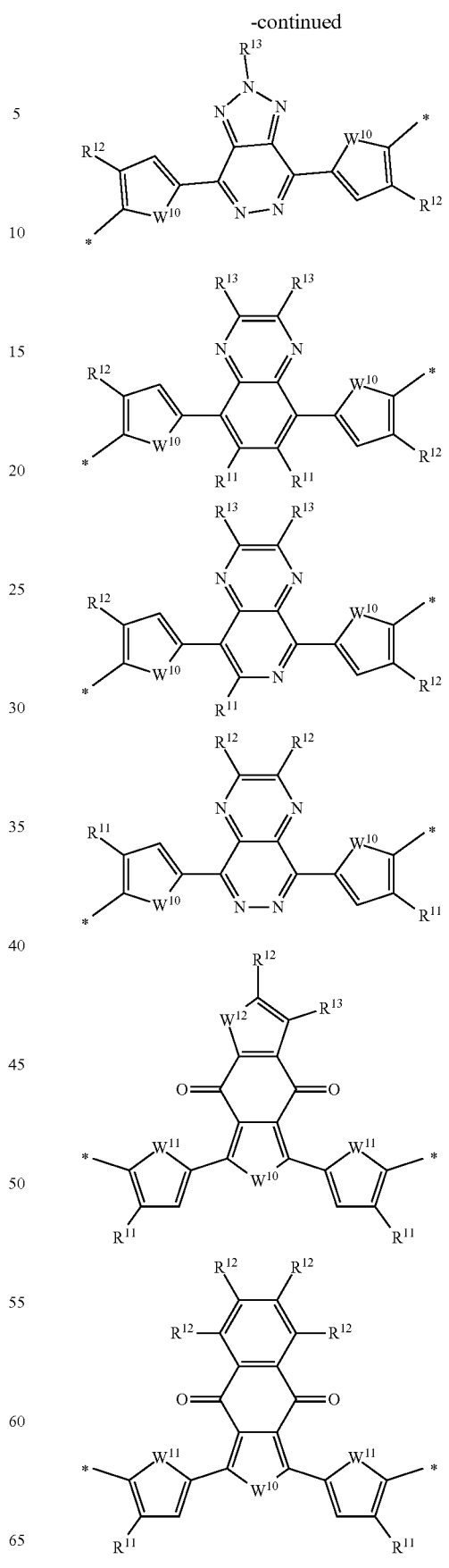

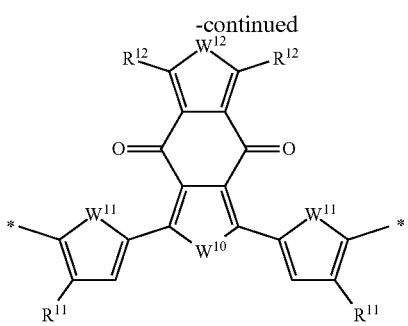

wherein $W^{10}$, $W^{11}$, and $W^{12}$ are selected from the group consisting of oxygen (O), sulfur (S), selenium (Se), and tellurium (Te); and $R^{11}$, $R^{12}$, and $R^{13}$ are respectively selected from the group consisting of free hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group.

10. The organic semiconductor mixture as claimed in claim 1, wherein the p-type organic semiconductor compound is selected from the group consisting of:

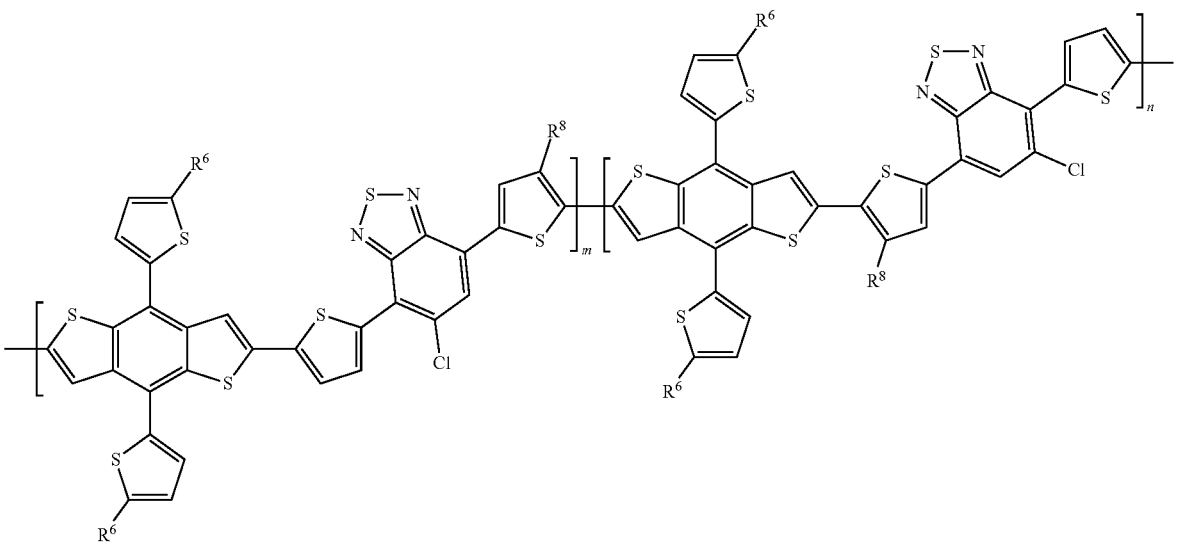

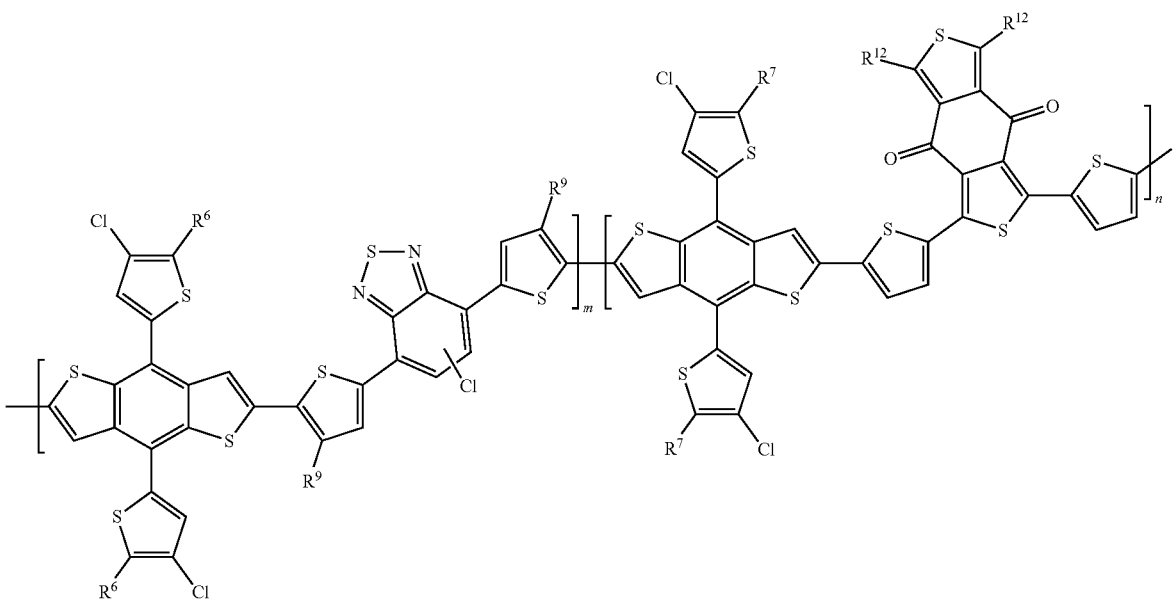

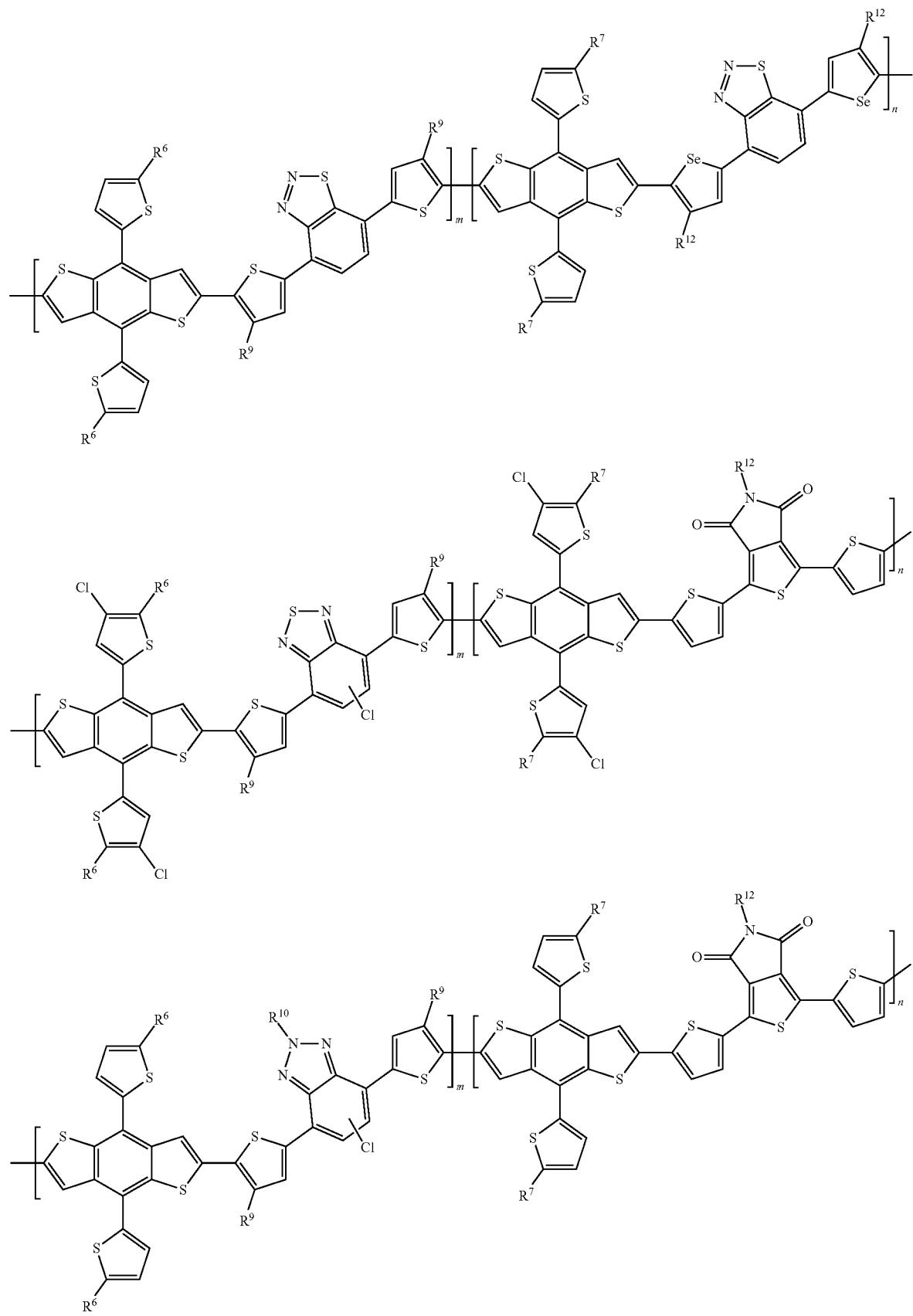

123
124
-continued
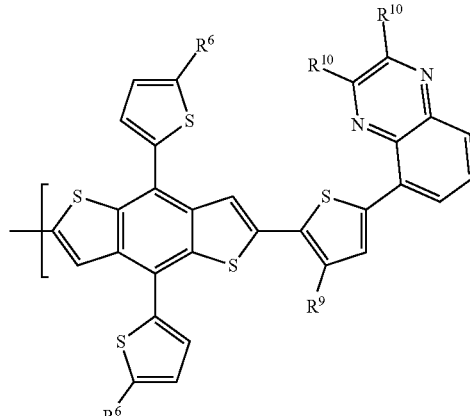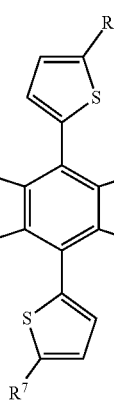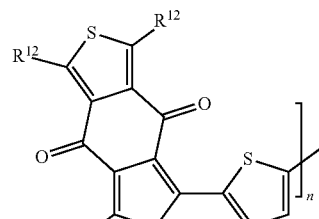
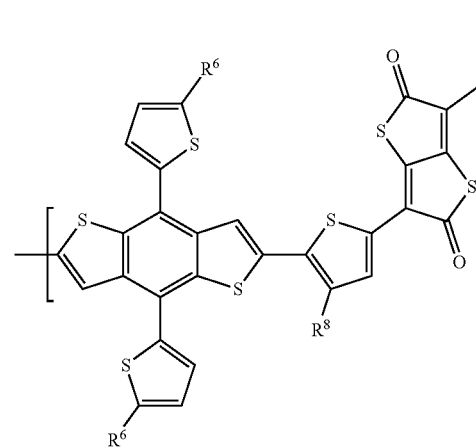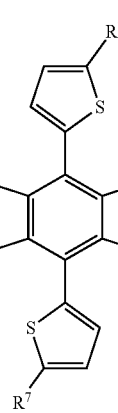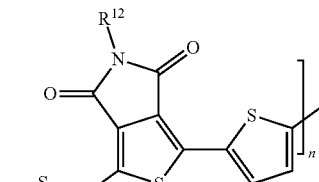

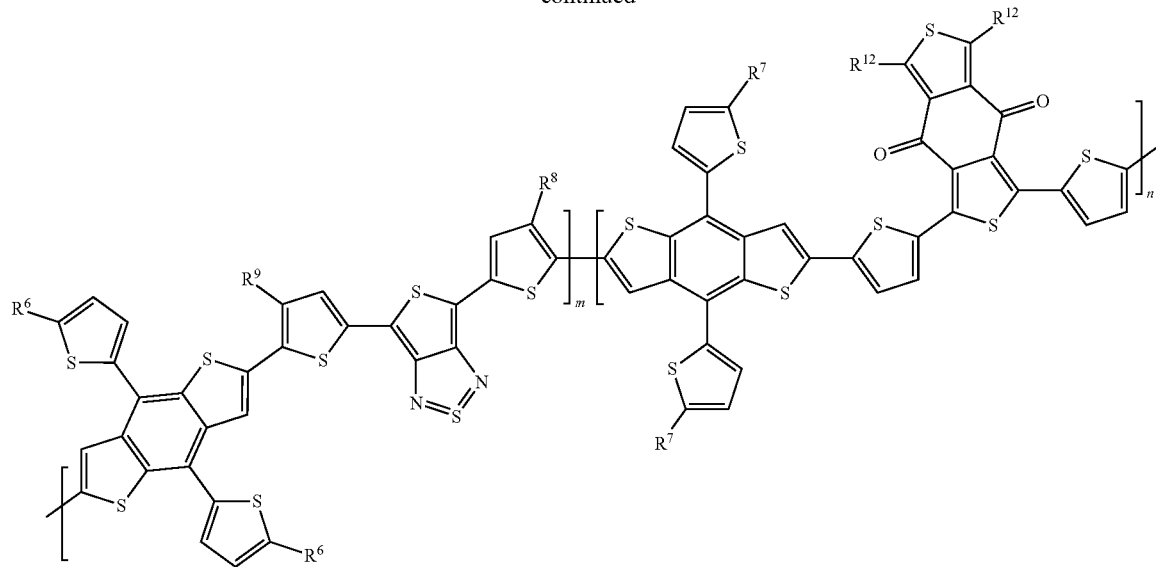

wherein $R^6$-$R^2$ are respectively selected from the group consisting of free hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl group; and $m+n=1$, $0<m\leq 1$, and $0\leq n<1$.

11. An organic optoelectronic device comprising:
a substrate,
an electrode module disposed on the substrate and provided with a first electrode and a second electrode, and
an active layer arranged between the first electrode and the second electrode and made from material containing at least one organic compound mixture as claimed in claim 1;
wherein at least one of the first electrode and the second electrode is transparent or semi-transparent.

12. The organic optoelectronic device as claimed in claim 11, wherein the first electrode, the active layer and the second electrode are disposed on the substrate in turn from bottom to top.

13. The organic optoelectronic device as claimed in claim 11, wherein the second electrode, the active layer and the first electrode are disposed on the substrate in turn from bottom to top.

14. The organic optoelectronic device as claimed in claim 11, wherein the organic optoelectronic device further includes a first carrier transport layer disposed between the first electrode and the active layer, and a second carrier transport layer arranged between the second electrode and the active layer.

15. The organic optoelectronic device as claimed in claim 11, wherein the organic optoelectronic device further includes a first carrier transport layer disposed between the second electrode and the active layer, and a second carrier transport layer arranged between the first electrode and the active layer.

* * * * *